US007105563B2

(12) United States Patent
Arnaiz et al.

(10) Patent No.: US 7,105,563 B2
(45) Date of Patent: Sep. 12, 2006

(54) INDOLINONE DERIVATIVES AND THEIR USE IN TREATING DISEASE-STATES SUCH AS CANCER

(75) Inventors: Damian Arnaiz, El Sobrante, CA (US); Judi Bryant, Mill Valley, CA (US); Yuo-Ling Chou, Lafayette, CA (US); Richard Feldman, El Cerrito, CA (US); Paul Hrvatin, Concord, CA (US); Imadul Islam, Hercules, CA (US); Monica Kochanny, Benicia, CA (US); Wheeseong Lee, Orinda, CA (US); Mark Polokoff, Walnut Creek, CA (US); Hongyi Yu, San Pablo, CA (US); Shendong Yuan, Richmond, CA (US)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 10/972,023

(22) Filed: Oct. 22, 2004

(65) Prior Publication Data

US 2005/0090541 A1 Apr. 28, 2005

Related U.S. Application Data

(60) Provisional application No. 60/514,081, filed on Oct. 24, 2003.

(51) Int. Cl.
*A61K 31/404* (2006.01)
*C07D 209/34* (2006.01)
(52) U.S. Cl. ...................... 514/414; 548/468
(58) Field of Classification Search ............... 548/468; 514/414
See application file for complete search history.

(56) References Cited

U.S. PATENT DOCUMENTS

| 5,792,783 | A | * | 8/1998 | Tang et al. | 514/397 |
|---|---|---|---|---|---|
| 5,854,206 | A | * | 12/1998 | Twardzik et al. | 514/12 |
| 5,880,141 | A | | 3/1999 | Tang et al. | |
| 5,883,116 | A | | 3/1999 | Tang et al. | |
| 2004/0204407 | A1 | * | 10/2004 | Tang et al. | 514/227.5 |
| 2004/0266843 | A1 | * | 12/2004 | Howlett et al. | 514/365 |

FOREIGN PATENT DOCUMENTS

| WO | WO96/40116 A | 12/1996 |
|---|---|---|
| WO | WO99/61422 | 12/1999 |
| WO | WO00/35906 | 6/2000 |
| WO | WO00/35909 | 6/2000 |
| WO | WO00/35920 | 6/2000 |
| WO | WO00/35921 | 6/2000 |
| WO | WO00/56709 | 9/2000 |
| WO | WO01/49287 A | 7/2001 |
| WO | WO01/83450 | 11/2001 |
| WO | WO02/66463 | 8/2002 |
| WO | WO03/022815 | 3/2003 |
| WO | WO03/31438 | 4/2003 |
| WO | WO03/051838 A | 6/2003 |
| WO | WO03/057690 A | 7/2003 |
| WO | WO03/064397 A | 8/2003 |
| WO | WO2004/048343 A | 6/2004 |
| WO | WO2004/111008 A | 12/2004 |

OTHER PUBLICATIONS

Tang et al., STN International (2005), HCAPLUS Database, Accession No. 129:175549, Reg. No. 91822-51-4).*
Howlett et al., STN International (2005), HCAPLUS Database, Columbus, OH, Accession No. 2005:2190.*
Vanhaesebroeck, B. and D. R. Alessi, "The P13K-PDK1 connection: more than just a road to PKB," *Biochem J.* (2000), vol. 346 (pt 3), pp. 561-576.
Besson, A. et al., "PTEN/MMAC1/TEP1 in signal transduction and tumorigenesis," *Eur. J. Biochem.* (1999), vol. 263, No. 3, pp. 605-611.
Myers, M.P. et al., "The lipid phosphate activity of PTEN is critical for its tumor suppressor function," *Proc. Natl. Acad. Sci. USA* (1998), vol. 95, No. 23, pp. 13513-13518.
Stambolic, V. et al., "Negative regulation of PKB/Akt-dependent cell survival by the tumor suppressor PTEN," *Cell* (1998), vol. 95, No. 1, pp. 29-39.
Testa, J.R. and A. Bellacosa, "AKT plays a central role in tumorigenesis," *Proc. Natl. Acad. Sci. USA* (2001), vol. 98, No. 20, pp. 10983-10985.
Vivanco, I. And C. L. Sawyers, "The phosphatidylinositol 3-Kinase AKT pathway in human cancer," *Nat'l Rev. Cancer* (2002), vol. 2, No. 7, pp. 489-501.

(Continued)

*Primary Examiner*—Kamal A. Saeed
*Assistant Examiner*—Andrew B. Freistein
(74) *Attorney, Agent, or Firm*—Jacqueline S. Larso; Ronald S. Hermenau; Berlex Inc.

(57) ABSTRACT

Indolinone derivatives, such as compounds of the formula (I):

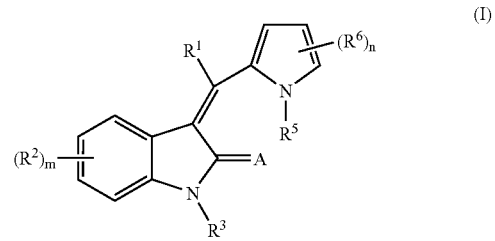

wherein A, m, n, $R^1$, $R^2$, $R^3$, $R^5$ and $R^6$ are described herein, are disclosed herein as being useful in treating mammal having disease-states alleviated by the inhibition of PDK-1 activity.

15 Claims, No Drawings

OTHER PUBLICATIONS

Datta, S. R. et al., "Cellular survival: a play in three Akts," *Genes Dev.* (1999), vol. 13, No. 22, pp. 2905-2927.

Holland, E. C. et al., "Combined activation of Ras and Akt in neural progenitors induces glioblastoma formation in mice," *Nat. Genet.* (2000), vol. 25, No. 1, pp. 55-57.

Dimmeler, S. and A. M. Zeiher, "Akt takes center stage in angiogenesis signaling," *Circ. Res.* (2000), vol. 86, No. 1, pp. 4-5.

Shiojima, I. and K. Walsh, "Role of Akt signaling in vascular homeostasis and angiogenesis," *Circ. Res.* (2002), vol. 90, No. 12, pp. 1243-1250.

Inoki, K. et al., "TSC2 is phosphorylated and inhibited by Akt and suppresses mTOR signaling," *Nat. Cell. Biol.* (2002), vol. 4, No. 9, pp. 648-657.

Potter, C. J. et al., "Akt regulates growth by directly phosphorylating Tsc2," *Nat. Cell. Biol.* (2002), vol. 4, No. 9, pp. 658-665.

Alessi, D. R. et al., "3-Phosphoinositide-dependent protein kinase 1 (PDK1) phosphorylates and activates the p70 S6 kinase in vivo and in vitro," *Curr. Biol.* (1998), vol. 8, No. 2, pp. 69-81.

Page, C. et al., "Overexpression of Akt/AKT can modulate chemothreapy-induced apoptosis," *Anticancer Res.* (2000), vol. 20, No. 1A, pp. 407-416.

Brognard, J. et al., "Akt/protein kinase B is constitutively active in non-small cell lung cancer cells and promotes cellular survival and resistance to chemotherapy and radiation," *Cancer Res.* (2001), vol. 61, No. 10, pp. 3986-3997.

Cantrell, D., "Protein kinase B (Akt) regulation and function in T lymphocytes," *Semin. Immunol.* (2002), vol. 14, No. 1, pp. 19-26.

Kato, M. et al., "Pyrrole Butyric Acid Derivatives as Inhibitors of Steroid 5α-Reductase," *Chem. Pharm. Bull.* (1997), vol. 45, No. 11, p. 1767.

Loader, C. et al., "Pyrrole chemistry. XXIII. The Cyanation of substituted pyrroles with chlorosulfonyl isocyanate (CSI). New synthesis of pyrrole-3-carbonitriles," *Can. J. Chem.* (1981), vol. 59, p. 2673.

Sonnet, P. E., "Synthesis of β-Substituted Pyrroles via 1-(Pyrrol-2-ylmethylene)pyrrolidinium Salts," *J. Org. Chem.*, (1971), vol. 36, p. 1005.

Miyayra, N. and Suzuki, A., "Palladium-Catalyzed Cross-Coupling Reactions of Organoboron Compounds," *Chem. Rev.* (1995), vol. 95, p. 2457.

Archibald, J. L. et al., "Benzamidopiperidines.2. Heterocyclic Compounds Related to Indoramin," *J. Med. Chem.* (1974), vol. 17, pp. 736-739.

Alezzi, D. R. et al., "Characterization of a 3-phosphoinositide-dependent protein kinase which phosphorylates and activates protein kinase B," *Curr. Biol.* (1997), vol. 7, pp. 261-269.

* cited by examiner

INDOLINONE DERIVATIVES AND THEIR USE IN TREATING DISEASE-STATES SUCH AS CANCER

This application claims priority to U.S. Provisional Application Ser. No. 60/514,081 filed Oct. 24, 2003 the entirety of which is incorporated herein by reference.

FIELD OF THE INVENTION

This invention is directed to indolinone derivatives which are useful in treating disease-states alleviated by the inhibition of the activity of the serine/threonine kinase known as phosphoinositide-dependent kinase-1 (PDK-1). This invention is also directed to pharmaceutical compositions containing the derivatives and methods of using such compounds and compositions in treating such disease-states as cancer.

BACKGROUND OF THE INVENTION

Phosphoinositide-dependent kinase-1 (PDK-1) is a serine/threonine (Ser/Thr) kinase that functions to phosphorylate and activate other Ser/Thr kinases in the AGC kinase family (see, e.g., Vanhaesebroeck, B. and D. R. Alessi, "The PI3K-PDK1 connection: more than just a road to PKB," Biochem. J. (2000), Vol. 346 (Pt 3), pp. 561–76). The best-characterized substrate of PDK-1 is the intracellular Ser/Thr kinase known as AKT, whose expression and/or activity is elevated in many cancers. Kinase activity of serum and glucocordicoid regulated kinase (SGK), which is structurally related to AKT, can also be phosphorylated and activated by PDK-1. Once activated in tumors, AKT promotes increased tumor cell survival, drug resistance, growth and angiogenesis. Three highly related isoforms of AKT, termed AKT1, AKT2 and AKT3 are known in humans. Activation of AKT is dependent on the activity of phosphatidylinsoitol-3 kinase (PI-3 kinase), whose activity is activated by many signaling molecules elevated in cancer cells, including growth factor receptors (e.g., epidermal growth factor (EGF) receptor, ErbB2 and IGF1-receptor) and oncogenes (e.g, Ras, BCR-abl, and Src). Other potential substrates of PDK-1 include p70 S6 kinase, p90 S6 kinase, protein kinase C, cAMP-dependent protein kinase (PKA), PRK1, Protein kinase G and serum and glucocorticoid regulated kinase (SGK).

PDK-1-mediated phosphorylation of AKT, which is largely present in an inactive form in unstimulated cells, converts the enzyme to a catalytically active form. This occurs through the phosphorylation of the activation loop domain of AKT, e.g., at threonine-309 in AKT2 and theonine-308 in AKT1. Phosphorylation of a homologous domain in many kinases is known to regulate their kinase activity. One stimulus for PDK-1-mediated phosphorylation of AKT is the association PI-3 kinase products, $(3,4,5)PIP_3$ or $(3,4)PIP_2$, with the pleckstrin homology (PH) domain of AKT. Although AKT displays low, basal levels of activation in normal, unstimulated cells, AKT often becomes constitutively activated in tumor cells. This occurs through the up-regulation of a variety of different signaling molecules or the presence of oncogenenic mutations commonly found in cancer cells that can promote the activation of AKT, such as PI-3 kinase, growth factor receptors (e.g., EGFR family members), Ras, Src, and BCR-ABL activation. Loss of the tumor suppressor PTEN is another means of greatly increasing AKT activity in cancer cells (Besson, A. et al., "PTEN/MMAC1/TEP1 in signal transduction and tumorigenesis," Eur. J. Biochem. (1999), Vol. 263, No. 3, pp. 605–611). PTEN mutation or down regulation of PTEN protein is found in a large number of tumors and cancer cell lines. PTEN is a phosphatase that removes the D-3 phosphate from the products of PI-3 kinase such as phosphatidylinositol 3,4,5-trisphosphate and phosphatidylinositol 3,4-bisphosphate (Myers, M. P. et al., "The lipid phosphatase activity of PTEN is critical for its tumor supressor function," Proc. Natl. Acad. Sci. USA (1998), Vol. 95, No. 23, pp. 13513–13518; Stambolic, V. et al., "Negative regulation of PKB/Akt-dependent cell survival by the tumor suppressor PTEN," Cell (1998), Vol. 95, No. 1, pp. 29–39). Loss of PTEN, therefore, has the effect of increasing products of PI-3 kinase and promoting constitutive activation of AKT. Cancers with highly up-regulated levels of AKT may be especially sensitive to the effects of PDK-1/AKT pathway inhibitors.

Downstream substrates of PDK-1 and/or AKT are associated with a number of cell responses including proliferation, metabolism and cell survival (Testa, J. R. and A. Bellacosa, "AKT plays a central role in tumorigenesis," Proc. Natl. Acad. Sci. USA (2001), Vol. 98, No. 20, pp. 10983–5; Vivanco, I. and C. L. Sawyers, "The phosphatidylinositol 3-Kinase AKT pathway in human cancer," Nat. Rev. Cancer (2002), Vol. 2, No. 7, pp. 489–501). Examples of signaling molecules downstream from PDK-1 or AKT involved in these pathways include BAD, p70 S6 kinase, p21 (Waf-1/Cip-1), Forkhead transcription factors, p27 (kip-1), GSK-3-alpha/beta, TSC2 (tuberin), and ecNOS. The survival function of AKT is particularly well-characterized cellular activity of AKT (Datta, S. R. et al., "Cellular survival: a play in three Akts," Genes Dev. (1999), Vol. 13, No. 22, pp. 2905–27). AKT functions to suppress cell death, i.e., apoptosis, induced by a variety of agents, including UV radiation, chemotherateutic drugs, TFG-beta, withdrawal of survival factors, overexpression of oncogenes such as c-myc and detachment of cells from the extracellular matrix.

The ability to escape apoptosis is a critical characteristic of tumor cells allowing their uncontrolled growth and invasive behavior. One trigger for apoptosis is the perturbation of the normal growth regulation resulting from oncogenic mutations or inappropriate expression signaling molecules coupled to cell proliferation. Apoptotic pathways, therefore, provide a key means of protection from the development and progression of cancer. Cancer cells, however, can escape apoptotic death by selecting for activation of signaling molecules such as AKT that turn off apoptotic signals. Some oncogenes, such as Ras, which is activated in as many as 60% of human tumors, simultaneously promote uncontrolled growth and the activation of AKT. Inhibition of AKT in NIH 3T3 cells prevents transformation of these cells through transfection with activated Ras. Furthermore, a number of studies have shown that combining expression of an oncogene with an activated form of AKT greatly facilitates formation of tumors in vivo (e.g., Holland, E. C. et al., "Combined activation of Ras and Akt in neural progenitors induces glioblastoma formation in mice," Nat. Genet.

(2000), Vol. 25, No. 1, pp. 55–7). Inhibitors of PDK-1, by blocking activation of AKT, are therefore a means of promoting apoptosis in tumors cells, especially, but not necessarily limited to those over-expressing AKT activity.

Inhibitors of the PDK-1/AKT pathway are also expected to block cancer progression through inhibition of tumor-stimulated angiogenesis (Dimmeler, S. and A. M. Zeiher, "Akt takes center stage in angiogenesis signaling," *Circ. Res.* (2000), Vol. 86, No. 1, pp. 4–5; and Shiojima, I. and K. Walsh, "Role of Akt signaling in vascular homeostasis and angiogenesis," *Circ. Res.* (2002), Vol. 90, No. 12, pp. 1243–50). AKT has been shown to regulate a number of responses critical for the process of angiogeneisis, including endothelial cell migration, proliferation and survival during new vessel formation, ecNOS regulation, response of endothelial cells to growth factors (including IGF-1, agniopoetin-1 and VEGF) and the regulation of hypoxia-inducible factor-1 (HIF-1)-alpha levels.

Inhibition of the cell cycle and growth of tumor cells is yet another expected effect of compounds that block PDK-1 and/or AKT. Inhibition of PDK-1 and/or AKT activity has been shown to regulate growth of cancer cells in a number of studies. These effects may occur through PDK-1 or AKT-mediated regulation of a number of different signaling pathways important in growth regulation. For example, AKT has been shown to block nuclear localization and/or expression of the cyclin-dependent kinase inhibitors, p21 (Waf-1/Cip-1) and p27 (kip-1). Inhibitors blocking these effects would be expected to reduce the activity of cyclin-dependent kinases, blocking progression through the cell cycle and reducing tumor cell growth. AKT was found to inhibit Myt1, thereby acting as an initiator of mitosis in oocytes from the starfish Asterina pectinfera. Furthermore, PDK-1 and/or AKT regulate the expression of proteins important for cell growth through its regulation of mTOR, p70 S6 kinase and eukaryotic initiation factor 4E binding protein 1 (4E-BP1). While the mechanism of this regulation is not firmly established, it has been shown that AKT phosphorylations reduces expression of TSC2, thereby relieving TSC-2 mediated suppression of mTOR activity. This, in turn, promotes the activation p70 S6 kinase activity and the phosphorylation and inhibition of 4E-BP1 (Inoki, K. et al., "TSC2 is phosphorylated and inhibited by Akt and suppresses mTOR signalling," *Nat. Cell. Biol.* (2002), Vol. 12, p. 12; and Potter, C. J. et al., "Akt regulates growth by directly phosphorylating Tsc2," *Nat. Cell. Biol.* (2002), Vol. 12, p. 12). Both these effects result in increased synthesis of mRNAs encoding proteins important for cell growth. Loss of TSC2 function is associated with the disease tuberous sclerosis, which results in differentiated benign growths (harmatomas) in a wide variety of organs. PDK-1 also has been shown to have a direct role in the phosphorylation and activation p70 S6 kinase (Alessi, D. R. et al., "3-Phosphoinositide-dependent protein kinase 1 (PDK1) phosphorylates and activates the p70 S6 kinase in vivo and in vitro," *Curr. Biol.* (1998), Vol. 8, No. 2, pp. 69–81).

Compounds which block PDK-1 mediated activation of AKT or PDK-1 directly may therefore be useful therapeutic agents in treating a variety of disease-states, such as cancer.

SUMMARY OF THE INVENTION

This invention is directed to indolinone derivatives that are useful in treating mammals, particularly humans, having a disease-state which is alleviated by the inhibition of PDK-1 activity.

Accordingly, in one aspect, this invention is directed to compounds of formula (I):

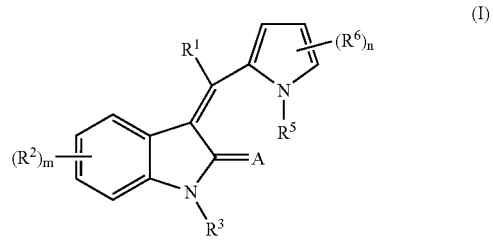

wherein:
m is 0 to 4;
n is 0 to 3;
A is oxygen or sulfur;
$R^1$ is hydrogen, alkyl, —C(O)O$R^7$, or —C(O)N($R^7$)$_2$; or
$R^1$ is aryl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—C(O)O$R^7$, —$R^8$—C(O)N($R^7$)$_2$, —$R^8$—N($R^7$)C(O)N($R^7$)$_2$, —$R^8$—N($R^7$)C(O)—$R^9$—N($R^7$)$_2$ and —$R^8$—N($R^7$)C(O)O$R^7$); or
$R^1$ is aralkyl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—C(O)O$R^7$, —$R^8$—C(O)N($R^7$)$_2$, —$R^8$—N($R^7$)C(O)N($R^7$)$_2$, —$R^8$—N($R^7$)C(O)—$R^9$—N($R^7$)$_2$ and —$R^8$—N($R^7$)C(O)O$R^7$); or
$R^1$ is heterocyclyl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—N($R^7$)C(O)N($R^7$)$_2$, —$R^8$—N($R^7$)C(O)—$R^9$—N($R^7$)$_2$ and —$R^8$—N($R^7$)C(O)O$R^7$); or
$R^1$ is heterocyclylalkyl (optionally substituted by one or more substituents selected from the group consisting of alkyl, aryl, aralkyl, halo, haloalkyl, cyano, nitro, —$R^8$—O$R^7$, —$R^8$—C(O)O$R^7$, —$R^8$—C(O)N($R^7$)$_2$, —$R^8$—N($R^7$)$_2$, —$R^8$—N($R^7$)C(O)N($R^7$)$_2$, —$R^8$—N($R^7$)C(O)—R—N($R^7$)$_2$ and —$R^8$—N($R^7$)C(O)O$R^7$);

each $R^2$ is independently selected from the group consisting of alkyl, alkenyl, alkynyl, halo, haloalkyl, haloalkenyl, cyano, —$R^8$—O$R^7$, —$R^8$—N($R^7$)$_2$, —$R^8$—C(O)O$R^7$, —$R^8$—C(O)N($R^7$)$_2$, —$R^8$—S(O)$_t$N($R^7$)$_2$ (where t is 1 or 2), —$R^8$—N($R^7$)S(O)$_t$$R^7$ (where t is 1 or 2), —$R^8$—N($R^7$)S(O)$_t$N($R^7$)$_2$ (where t is 1 or 2), —$R^8$—N($R^7$)S(O)$_t$N($R^7$)C(O)O$R^7$ (where t is 1 or 2), —$R^8$—N($R^7$)C(O)$R^7$, —$R^8$—N($R^7$)—$R^8$—C(O)O$R^7$, —$R^8$—N($R^7$)C(O)N($R^7$)$_2$, —$R^8$—N($R^7$)C(O)—$R^9$—N($R^7$)$_2$, —$R^8$—N($R^7$)—$R^9$—C(O)N($R^7$)$_2$, —$R^8$—N($R^7$)C(O)—$R^8$—N($R^7$)—$R^8$—C(O)O$R^7$, —$R^8$—N($R^7$)C(O)—$R^8$—N($R^7$)—$R^8$—C(O)—$R^8$—N($R^7$)$_2$, —N($R^7$)C(=N$R^7$)N($R^7$)$_2$, —C(=N$R^7$)—N($R^7$)$_2$, —$R^8$—N=C($R^7$)$_2$, heterocyclyl (optionally substituted by one or more substituents selected from the group consisting of alkyl, aryl, aralkyl, halo, haloalkyl, cyano, nitro, —$R^8$—O$R^7$, —$R^8$—C(O)O$R^7$, —$R^8$—C(O)N($R^7$)$_2$, —$R^8$—N($R^7$)$_2$, —$R^8$—N($R^7$)C(O)—$R^8$—N($R^7$)$_2$ and —$R^8$—N($R^7$)C(O)O$R^7$); and optionally substituted cyclic ureido groups;

$R^3$ is hydrogen, alkyl or aralkyl;
$R^5$ is hydrogen, alkyl, aryl, aralkyl, —C(O)$R^{11}$ or —S(O)$_2$$R^{11}$;
each $R^6$ is independently selected from the group consisting of alkyl, alkenyl, alkynyl, halo, haloalkyl, cyano, nitro, optionally substituted aryl, optionally substituted aralkyl, optionally substituted heterocyclyl, —R$^9$—OR$^7$, —R$^8$—C(O)OR$^7$, —R$^8$—C(O)N(R$^7$)$_2$, —R$^8$—C(O)—R$^9$—N(R$^7$)$_2$, —R$^8$—C(O)R$^7$, —R$^8$—N(R$^7$)$_2$, —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)C(O)—R$^{10}$—N(R$^7$)$_2$, —R$^8$—N(R$^7$)C(O)—R$^8$—N(R$^7$)C(O)—R$^8$—N(R$^7$)$_2$, —R$^8$—C(O)—R$^9$—C(O)OR$^7$, —R$^8$—C(O)—R$^9$—C(O)N(R$^7$)$_2$, —R$^8$—N(R$^7$)C(O)—R$^8$—N(R$^7$)—R$^8$—C(O)OR$^7$, —R$^8$—N(R$^7$)C(O)—R$^8$—N(R$^7$)—R$^8$—C(O)N(R$^7$)$_2$, —R$^8$—N(R$^7$)C(O)—R$^9$—C(O)OR$^7$, —R$^8$—N(R$^7$)C(O)—R$^9$—C(O)N(R$^7$)$_2$, —R$^8$—S(O)$_t$—N(R$^7$)$_2$ (where t is 1 or 2), —R$^8$—N(R$^7$)S(O)$_t$—R$^8$—N(R$^7$)$_2$ (where t is 1 or 2), and —R$^8$—N(R$^7$)S(O)$_t$—R$^7$ (where t is 1 or 2);

each R$^7$ is independently hydrogen, optionally substituted alkyl, haloalkyl, optionally substituted aryl, optionally substituted aralkyl, optionally substituted heterocyclyl, or optionally substituted heterocyclylalkyl;

each R$^8$ is a bond or a straight or branched alkylene chain;

each R$^9$ is a straight or branched alkylene chain;

R$^{10}$ is an amino acid residue other than a straight or branched alkylene chain; and each R$^{11}$ is optionally substituted alkyl, haloalkyl, optionally substituted aryl, optionally substituted aralkyl, optionally substituted heterocyclyl, or optionally substituted heterocyclylalkyl;

as a single stereoisomer, a mixture of stereoisomers, a solvate or a polymorph; or a pharmaceutically acceptable salt thereof;

with the following provisos:

(1) when m is 1, n is 1, A is oxygen, R$^1$, R$^3$ and R$^5$ are each hydrogen and R$^6$ is 3-methoxy, R$^2$ can not be 4-bromo, 4-iodo, 5-bromo;

(2) when m is 1, n is 0, A is oxygen, R$^1$, R$^3$ and R$^5$ are each hydrogen, R$^2$ can not be 5-bromo, 5-iodo or 4-bromo;

(3) when R$^6$ is 3-methoxy, R$^2$ can not be optionally substituted ethenyl or ethynyl;

(4) when m is 2, n is 1, A is oxygen, R$^1$, R$^3$ and R$^5$ are each hydrogen and R$^6$ is methoxy, one R$^2$ can not be 4-bromo when the other R$^2$ is 5-nitro;

(5) when m is 0, n is 2, A is oxygen, R$^3$ and R$^5$ are each hydrogen, and one R$^6$ is 3-methyl and the other R$^6$ is 5-methyl, R$^1$ can not be hydrogen, —C(O)OR$^7$ or —C(O)N(R$^7$)$_2$;

(6) when m is 0, n is 0, A is oxygen, and R$^1$ and R$^3$ are each hydrogen, R$^5$ can not be hydrogen;

(7) when m is 1, n is 0, A is oxygen, and R$^1$, R$^3$ and R$^5$ are each hydrogen, R$^2$ can not be 4-methyl, 4-bromo, 4-thien-2-yl, or 2,6-dimethoxypyrimidin-4-yl;

(8) when m is 1, n is 1, A is oxygen, R$^1$, R$^3$ and R$^5$ are each hydrogen, and R$^6$ is 3-methoxy, R$^2$ can not be 4-indol-5-yl, 4-indol-6-yl or 4-indol-4-yl;

(9) when m is 1, n is 1, R$^1$, R$^3$ and R$^5$ are each hydrogen, R$^6$ is 3-methoxy, and one R$^2$ is 4-indol-6-yl, the other R$^2$ can not be 5-nitro, 5-amino or 5-(thien-2-ylacetamido);

(10) when m is 2, n is 0 or 1, A is oxygen, R$^1$, R$^3$ and R$^5$ are each hydrogen, and R$^6$ is 3-methoxy, one R$^2$ can not be 4-amino when the other R$^2$ is 5-amino;

(11) when m is 2, n is 0 or 1, A is oxygen, R$^1$, R$^3$ and R$^5$ are each hydrogen, and R$^6$ is 3-methoxy, one R$^2$ can not be 5-nitro when the other R$^2$ is 4-fluoro or 4-azido;

(12) when m is 0, n is 3, A is oxygen, R$^1$, R$^3$ and R$^5$ are each hydrogen, and one R$^6$ is 3-methyl and the second R$^6$ is 5-methyl, the third R$^6$ can not be 4-(2-carboxyethyl), 4-(3-morpholin-4-ylpropyl) or 4-(3-dimethylaminopropyl);

(13) when m is 1, n is 2, A is oxygen, R$^1$, R$^3$ and R$^5$ are each hydrogen, and one R$^6$ is 3-methyl and the other R$^6$ is 4-(2-carboxyethyl) or 4-[2-(3,5-dimethoxybenzyloxycarbonyl)ethyl], R$^2$ can not be 5-chloro, 6-methoxy, 5-bromo, 5-iodo, 4-methyl, 5-methyl, 6-chloro, 5-methoxycarbonyl, 5-carboxy, 5-aminosulfonyl, 5-methylaminosulfonyl, 5-(2-carboxyethyl), 5-ethyl, 5-methoxy, 6-hydroxy, 6-bromo or 6-bromo;

(14) when m is 1, n is 3 A is oxygen, R$^1$, R$^3$ and R$^5$ are each hydrogen, and one R$^6$ is 3-methyl and the second R$^6$ is 5-methyl and the third R$^6$ is 4-(2-carboxyethyl), 4-(3-dimethylaminopropyl) or 4-(3-morpholin-4-ylpropyl), R$^2$ can not be 5-chloro, 5-bromo, 5-iodo, 4-methyl, 5-methyl, 6-hydroxy, 6-methoxy, 6-morpholin-4-yl, 6-chloro, 5-methoxy, 4-(2-hydroxyethyl), 5-aminosulfonyul, 5-(1-methylethylaminosulfonyl), 5-(morpholin-4-yulsulfonyl) or 5-(dimethylaminocarbonyl);

(15) when m is 0, n is 2, A is oxygen, R$^1$, R$^3$ and R$^5$ are each hydrogen, and one R$^6$ is 3-methoxy, the other R$^6$ can not be 5-methyl or 4-(2-carboxyethyl);

(16) when m is 2, n is 2, A is oxygen, R$^1$, R$^3$ and R$^5$ are each hydrogen, one R$^6$ is 4-(l2-carboxyethyl) and the second R$^6$ is 3-methyl, the two R$^2$'s can not be 5,6-dimethoxy or 4-methyl-5-chloro;

(17) when m is 2, n is 3, A is oxygen, R$^1$, R$^3$ and R$^5$ are each hydrogen, one R$^6$ is 3-methyl and the second R$^6$ is 5-methyl and the third R$^6$ is 4-(2-carboxyethyl), the R$^2$'s can not be 4-methyl and 5-chloro;

(18) when m is 0, n is 0, A is oxygen, R$^1$ and R$^5$ are each hydrogen, R$^5$ can not be hydrogen, methyl, 4-chlorophenyl or 3,5-dichlorophenyl;

(19) when m is 0, n is 1, A is oxygen, R$^1$, R$^3$ and R$^5$ are each hydrogen, R$^2$ can not be 3-methyl or 5-ethyl;

(20) when m is 0, n is 2, A is oxygen, R$^1$, R$^3$ and R$^5$ are each hydrogen, the R$^2$'s together can not be 3,4-dimethyl, 3,5-dimethyl, 3-methyl-4-[2-carboxyethyl], 3-methyl-4-[2-methoxycarbonylethyl] or 4-methyl-3-ethoxycarbonyl;

(21) when m is 0, n is 3, A is oxygen, R$^1$, R$^3$ and R$^5$ are each hydrogen, the R$^2$'s together can not be 4-[ethoxycarbonyl]-3,5-dimethyl, 5-methyl-3,4-dibromo, 5-formyl-3,4-dimethyl, 3-ethyl-4,5-dimethyl, 5-ethoxycarbonyl-4-[2-ethoxycarbonylethyl]-3-[ethoxycarbonylmethyl], 5-carboxy-3-ethyl-4-methyl, 4-methyl-3,5-dichloro, 5-chloro-3-methoxycarbonyl-4-[methoxycarbonylmethyl], 3-acetyl-5-ethoxycarbonyl-4-methyl, 5-ethoxycarbonyl-3-(2-ethoxycarboxylethyl)-4-(ethoxycarbonylmethyl), 4-ethyl-3,5-dimethyl, 4-prop-3-enyl-3,5-dimethyl;

(22) when m is 1, n is 0, A is oxygen, R$^1$, R$^3$ and R$^5$ are each hydrogen, R$^2$ can not be 5-chloro or 5-nitro;

(23) when m is 1, n is 1, A is oxygen, R$^1$, R$^3$ and R$^5$ are each hydrogen, R$^6$ is 3-methyl, R$^2$ can not be 5-nitro or 5-chloro;

(24) when m is 1, n is 2, A is oxygen, R$^1$, R$^3$ and R$^5$ are each hydrogen, and the R$^6$'s are 3,5-dimethyl, R$^2$ can not be 5-nitro or 5-chloro;

(25) when m is 2, n is 0 or 1, A is oxygen, R$^1$, R$^3$ and R$^5$ are each hydrogen, R$^6$ is 3-methoxy, and one R$^2$ is 4-amino, the other R$^2$ can not be 5-amino;

(26) when m is 2, n is 0 or 1, A is oxygen, R$^1$, R$^3$ and R$^5$ are each hydrogen, R$^6$ is 3-methoxy, and one R$^2$ is 5-nitro, the other R$^2$ can not be 4-fluoro or 4-azido;

(27) when m is 1, n is 3, A is oxygen, R$^1$, R$^3$ and R$^5$ are each hydrogen, one R$^6$ is 3-methyl, the second R$^6$ is 5-methyl and the third R$^6$ is 4-(3-dimethylaminopropyl) or 4-(2-carboxyethyl), R$^2$ can not be 6-(pyridin-3-yl), 6-(thien-2-yl), 4-(2-hydroxyethyl), or 4-(2-(3-(1-methylethyl)phenoxy)ethyl];

(28) when m is 0, n is 2, A is oxygen, $R^3$ and $R^5$ are each hydrogen, and one $R^6$ is 3-methyl and the second $R^6$ is 5-methyl, $R^1$ can not be 4-methoxyphenyl or 3,4-dimethoxyphenyl;

(29) when m is 2, n is 1, A is oxygen, $R^1$, $R^3$ and $R^5$ are each hydrogen, and one $R^2$ is 4-amino and the second $R^2$ is 5-amino, $R^6$ can not be 3-methoxy;

(30) when m is 2, n is 1, A is oxygen, $R^1$, $R^3$ and $R^5$ are each hydrogen, and one $R^2$ is 4-fluoro or 4-azido and the second $R^2$ is 5-nitro, $R^6$ can not be 3-methoxy;

(31) when m is 0 or 1, n is 3, A is oxygen, $R^1$, $R^3$ and $R^5$ are each hydrogen, and one $R^6$ is 5-methyl and the second $R^6$ is 3-methyl or 3-phenyl (optionally substituted by fluoro, chloro or cyano) and the third $R^6$ is —C(O)OH or —C(O)N($R^7$)$_2$ where one $R^7$ is hydrogen or methyl and the other $R^7$ is alkyl optionally substituted by hydroxy, diethylamino and/or an optionally substituted N-heterocyclyl, $R^2$ can not be halo, trifluoromethoxy, —C(O)$R^7$ (where $R^7$ is morpholinyl) or —C(O)N($R^7$)$_2$ (where each $R^7$ is independently hydrogen, hydroxyalkyl, alkyl or phenyl) at the 5-position; and

(32) m is 1, when n is 3, A is oxygen, $R^1$, $R^3$ and $R^5$ are each hydrogen, and one $R^6$ is 3-methyl and the second $R^6$ is 5-methyl and the third $R^6$ is —C(O)$R^7$ in the 4-position (where $R^7$ is optionally substituted N-heterocyclyl)$R^6$ can not be —C(O)$R^7$ in the 4-position where $R^7$ is optionally subsituted N-heterocyclyl, $R^2$ can not be halo or 3-pyridinyl.

In another aspect this invention is directed to compounds of formula (II):

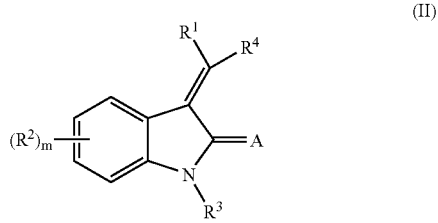

(II)

wherein:
m is 0 to 4;
A is oxygen or sulfur;
$R^1$ is hydrogen, alkyl, haloalkyl, —C(O)O$R^7$, or —C(O)N($R^7$)$_2$;
or $R^1$ is aryl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—C(O)O$R^7$, —$R^8$—C(O)N($R^7$)$_2$, —$R^8$—N($R^7$)C(O)—$R^8$—N($R^7$)$_2$ and —$R^8$—N($R^7$)C(O)O$R^7$); or $R^1$ is aralkyl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—C(O)O$R^7$, —$R^8$—C(O)N($R^7$)$_2$, —$R^8$—N($R^7$)C(O)—$R^8$—N($R^7$)$_2$ and —$R^8$—N($R^7$)C(O)O$R^7$); or $R^1$ is heterocyclyl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—C(O)O$R^7$, —$R^8$—C(O)N($R^7$)$_2$, —$R^8$—N($R^7$)C(O)—$R^8$—N($R^7$)$_2$ and —$R^8$—N($R^7$)C(O)O$R^7$); or $R^1$ is heterocyclylalkyl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—C(O)O$R^7$, —$R^8$—C(O)N($R^7$)$_2$, —$R^8$—N($R^7$)C(O)—$R^8$—N($R^7$)$_2$ and —$R^8$—N($R^7$)C(O)O$R^7$);

each $R^2$ is independently selected from the group consisting of alkyl, alkenyl, alkynyl, halo, haloalkyl, haloalkenyl, cyano, —$R^8$—O$R^7$, —$R^8$—N($R^7$)$_2$, —$R^8$—C(O)O$R^7$, —$R^8$—C(O)N($R^7$)$_2$, —$R^8$—S(O)$_t$N($R^7$)$_2$ (where t is 1 or 2), —$R^8$—N($R^7$)S(O)$_t$$R^7$ (where t is 1 or 2), —$R^8$—N($R^7$)S(O)$_t$N($R^7$)$_2$ (where t is 1 or 2), —$R^8$—N($R^7$)S(O)$_t$N($R^7$)C(O)O$R^7$ (where t is 1 or 2), —$R^8$—N($R^7$)C(O)$R^7$, —$R^8$—N($R^7$)—$R^8$—C(O)O$R^7$, —$R^8$—N($R^7$)C(O)—$R^8$—N($R^7$)$_2$, —$R^8$—N($R^7$)C(O)—$R^8$—N($R^7$)—$R^8$—C(O)O$R^7$, —$R^8$—N($R^7$)C(O)—$R^8$—N($R^7$)—$R^8$—C(O)—$R^8$—N($R^7$)$_2$, —N($R^7$)C(=N$R^7$)N($R^7$)$_2$, —C(=N$R^7$)—N($R^7$)$_2$, —$R^8$—N=C($R^7$)$_2$, heterocyclyl (optionally substituted by one or more substituents selected from the group consisting of alkyl, aryl, aralkyl, halo, haloalkyl, cyano, nitro, —$R^8$—O$R^7$, —$R^8$—C(O)O$R^7$, —$R^8$—C(O)N($R^7$)$_2$, —$R^8$—N($R^7$)$_2$, —$R^8$—N($R^7$)C(O)—$R^8$—N($R^7$)$_2$ and —$R^8$—N($R^7$)C(O)O$R^7$); and optionally substituted cyclic ureido groups;

$R^3$ is hydrogen, alkyl or aralkyl;

$R^4$ is naphthyl (optionally substituted by one or more substituents selected from the group consisting of alkyl, aryl, aralkyl, halo, haloalkyl, cyano, nitro, —$R^8$—O$R^7$, —$R^8$—N($R^7$)$_2$, —$R^8$—C(O)O$R^7$, —$R^8$—C(O)N($R^7$)$_2$, —$R^8$—N($R^7$)C(O)—$R^8$—N($R^7$)$_2$ and —$R^8$—N($R^7$)C(O)O$R^7$); or $R^4$ is heterocyclyl (optionally substituted by one or more substituents selected from the group consisting of alkyl, aryl, aralkyl, halo, haloalkyl, cyano, nitro, —$R^8$—O$R^7$, —$R^8$—OC(O)$R^7$, —$R^8$—N($R^7$)$_2$, —$R^8$—C(O)O$R^7$, —$R^8$—C(O)N($R^7$)$_2$, —$R^8$—N($R^7$)C(O)—$R^8$—N($R^7$)$_2$ and —$R^8$—N($R^7$)C(O)O$R^7$);

each $R^7$ is independently selected from the group consisting of hydrogen, alkyl, —$R^9$—O$R^7$, haloalkyl, aryl, aralkyl, heterocyclyl, heterocyclylalkyl; and each $R^8$ is a bond or a straight or branched alkylene chain; and each $R^9$ is a straight or branched alkylene chain;

as a single stereoisomer, a mixture of stereoisomers, or as a racemic mixture of stereoisomers; or as a solvate or polymorph; or as a pharmaceutically acceptable salt thereof; with the following provisos:

(1) when m is 2, A is oxygen, $R^1$ and $R^3$ are each hydrogen, one $R^2$ is 5-nitro and the other $R^2$ is 4-bromo, $R^4$ can not be 5-methylimidazol-4-yl;

(2) when m is 2, A i oxygen, $R^1$ and $R^3$ are each hydrogen, one $R^2$ is 5-fluoro and the other $R^2$ is 4-iodo or 4-(1,3-benzodioxol-5-yl), $R^4$ can not be 5-methylimidazol-4-yl;

(3) when m is 1, A is oxygen, $R^1$ and $R^3$ are each hydrogen, and $R^2$ is 4-(2-hydroxyethyl), $R^4$ can not be pyridin-2-yl, 6-methylpyridin-2-yl, indol-5-yl, or 3-hydroxy-6-methylpyridin-2-yl;

(4) when m is 1, A is oxygen, $R^1$ and $R^3$ are each hydrogen, and $R^2$ is 5-bromo or 5-ethynyl, $R^4$ can not be 5-methylimidazol-4-yl;

(5) when m is 0, A is oxygen, and $R^1$ and $R^3$ are each hydrogen, $R^4$ can not be pyridin-4-yl, 4-methylthien-2-yl, 5-methylthiothien-2-yl, 5-methylthieny-2-yl, 3-methylthien-2-yl, furan-2-yl, thien-2-yl, 5-[3,5-di(trifluoromethyl)phenyl]furan-2-yl, 5-iodofuran-2-yl, 4-ethoxycarbonyl-5-methylfuran-2-yl, 3-bromothien-2-yl, 5-chlorothien-2-yl, 4,5-dimethylfuran-2-yl, 5-nitrothien-2-yl, 5-carboxythien-2-yl, 5-bromothien-2-yl, 4-bromothien-2-yl, 5-sulfonylfuran-2-yl, furan-2-yl, 5-methylfuran-2-yl, 5-ethylfuran-2-yl, 5-nitrofuran-2-yl, 5-bromofuran-2-yl, 5-ethylthien-2-yl, 5-methylimidazol-2-yl, 5-methylthiazol-2-yl, 5-methylpyrazol-3-yl, imidazol-4-yl, 4-chloropyrazol-3-yl, 2-(4-chlorobenzyl)-4-bromopyrazol-3-yl, 4-chloro-1-methylpyrazol-3-yl, oxazolyl, thiazolyl, pyrazolyl, isoxazolyl, isothiazolyl, triazolyl, thiadiazolyl, 5-phenyl-1,2,4-oxadiazol-3-yl, 3-phenyl-1,2,4-oxadiazol-5-yl, 3-phenyl-1,2,5-oxadiazol-4-yl, 3-methylthien-2-yl, 5-methylimidazolyl-2-yl, bicyclo[2.2.1]hept-5-en-2-yl; indol-3-yl; pyridin-4-yl, or pyridin-2-yl;

(6) when m is 1, A is oxygen, $R^1$ and $R^3$ are each hydrogen and $R^2$ is 5-chloro or 5-nitro, $R^4$ can not be indol-3-yl, thien-2-yl, 3-methylthien-2-yl, 5-methylthien-2-yl, 5-ethylthien-2-yl, 5-methylthiothieny-2-yl or imidazol-2-yl;

(7) when m is 2, A is oxygen, $R^1$ and $R^3$ are each hydrogen, and $R^4$ is 5-methylimidazol-4-yl, two $R^2$ groups together can not be 4-fluoro-5-nitro, 4-azido-5-nitro, 4-amino-5-nitro or 4,5-diamino;

(8) when m is 1, A is oxygen, $R^1$ and $R^3$ are each hydrogen, and $R^2$ is —S(O)$_2$N($R^7$)H (where $R^7$ is hydrogen, alkyl or hydroxyalkyl, $R^4$ can not be optionaly substituted 4,5,6,7-tetrahydroindol-2-yl; and (9) when m is 0, A is oxygen, $R^1$ and $R^3$ are each hydrogen, $R^4$ can not be 4-dimethylaminonaphthyl.

In another aspect, this invention is directed to methods of treating mammals, particularly humans, having a disease-state alleviated by the inhibition of PDK-1 activity, wherein the method comprises administering to the mammal a compounds of formula (I) or formula (II) as described above, including those compounds described in the provisos.

In another aspect, this invention is directed to pharmaceutical compositions comprising a pharmaceutically acceptable excipient and a compound of formula (I) or formula (II) as described above.

DETAILED DESCRIPTION OF THE INVENTION

Definitions

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

As used in the specification and appended claims, unless specified to the contrary, the following terms have the meaning indicated.

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like. Unless stated otherwise specifically in the specification, the alkyl radical may be optionally substituted by one or more substituents selected from the group consisting of cyano, nitro, —OR$^7$, —N($R^7$)$_2$, —C(O)R$^7$, —C(O)OR$^7$, —C(O)N($R^7$)$_2$, —N($R^7$)C(O)OR$^7$, —N($R^7$)C(O)R$^7$, —S(O)$_p$R$^7$ (where p is 0 to 2), and —S(O)$_p$N($R^7$)$_2$ (where p is 0 to 2) where each $R^7$ is as defined above in the Summary of the Invention. Unless stated otherwise specifically in the specification, it is understood that for radicals, as defined below, that contain a substituted alkyl group that the substitution can occur on any carbon of the alkyl group.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by one or more substituents selected from the group consisting of cyano, nitro, —OR$^7$, —N($R^7$)$_2$, —C(O)R$^7$, —C(O)OR$^7$, —C(O)N($R^7$)$_2$, —N($R^7$)C(O)OR$^7$, —N($R^7$)C(O)R$^7$, —S(O)$_p$R$^7$ (where p is 0 to 2), and —S(O)$_p$N($R^7$)$_2$ (where p is 0 to 2) where each $R^7$ is as defined above in the Summary of the Invention. Unless stated otherwise specifically in the specification, it is understood that for radicals, as defined below, that contain a substituted alkenyl group that the substitution can occur on any carbon of the alkenyl group.

"Alkynyl" refers to to a straight or branched hydrocarbon chain radical consisting solely of carbon and hydrogen atoms, containing at least one triple bond, having from two to eight carbon atoms, and which is attached to the rest of the molecule by a single bond or a double bond, e.g., ethynyl, prop-1-ynyl, but-1-ynyl, pent-1-ynyl, penta-1,4-diynyl, and the like. Unless stated otherwise specifically in the specification, the alkenyl radical may be optionally substituted by one or more substituents selected from the group consisting of cyano, nitro, —OR$^7$, —N($R^7$)$_2$, —C(O)R$^7$, —C(O)OR$^7$, —C(O)N($R^7$)$_2$, —N($R^7$)C(O)OR$^7$, —N($R^7$)C(O)R$^7$, —S(O)$_p$R$^7$ (where p is 0 to 2), and —S(O)$_p$N($R^7$)$_2$ (where p is 0 to 2) where each $R^7$ is as defined above in the Summary of the Invention. Unless stated otherwise specifically in the specification, it is understood that for radicals, as defined below, that contain a substituted alkenyl group that the substitution can occur on any carbon of the alkynyl group.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, alkynyl, halo, haloalkyl, haloalkenyl, cyano, nitro, aryl, aralkyl, aralkenyl, cycloalkyl, cycloalkylalkyl, cycloalkylalkenyl, heterocyclyl, heterocyclylalkyl, —R$^8$—OR$^7$, —R$^8$—O—R$^9$—C(O)OR$^7$, —R$^8$—N($R^7$)$_2$, —R$^8$—C(O)R$^7$, —R$^8$—C(O)OR$^7$, —R$^8$—C(O)N($R^7$)$_2$, —R$^8$—N($R^7$)C(O)OR$^7$, —R$^8$—N($R^7$)C(O)R$^7$, —R$^8$—S(O)$_p$R$^7$ (where p is 0 to 2), —R$^8$—S(O)$_p$N($R^7$)$_2$ (where p is 0 to 2), —R$^8$—N($R^7$)C(O)—R$^8$—N($R^7$)—R$^8$—C(O)OR$^7$, and —R$^8$—N($R^7$)C(O)—R$^8$—N($R^7$)$_2$ where each $R^7$, $R^8$ and $R^9$ is as defined above in the Summary of the Invention.

"Aralkyl" refers to a radical of the formula —R$_a$R$_b$ where R$_a$ is an alkyl radical as defined above and R$_b$ is one or more aryl radicals as defined above, e.g., benzyl, diphenylmethyl and the like. The alkyl radical and the aryl radical(s) may be optionally substituted as described above.

"Aralkenyl" refers to a radical of the formula —R$_c$R$_b$ where R$_c$ is an alkenyl radical as defined above and R$_b$ is one or more aryl radicals as defined above, e.g., 3-phenylprop-1-enyl, and the like. The alkenyl radical and the aryl radical(s) and the alkenyl radical may be optionally substituted as described above.

"Alkylene" or "alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of halo, cyano, nitro, aryl, cycloalkyl, heterocyclyl, cyano, nitro, —OR$^7$, —N($R^7$)$_2$, —C(O)R$^7$, —C(O)OR$^7$, —C(O)N($R^7$)$_2$, —N($R^7$)C(O)OR$^7$, —N($R^7$)C(O)R$^7$, —S(O)$_p$R$^7$ (where p is 0 to 2), and —S(O)$_p$ N($R^7$)$_2$ (where p is 0 to 2) where each $R^7$ is as defined above in the Summary of the Invention. The alkylene chain may be attached to the rest of the molecule through any two carbons within the chain.

"Alkenylene" or "alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like. The alkenylene chain may be optionally substituted by one or more substituents selected from the group consisting of halo, cyano, nitro, aryl, cycloalkyl, heterocyclyl, cyano, nitro, —$OR^7$, —$N(R^7)_2$, —$C(O)R^7$, —$C(O)OR^7$, —$C(O)N(R^7)_2$, —$N(R^7)C(O)OR^7$, —$N(R^7)C(O)R^7$, —$S(O)_pR^7$ (where p is 0 to 2), and —$S(O)_p N(R^7)_2$ (where p is 0 to 2) where each $R^7$ is as defined above in the Summary of the Invention. The alkenylene chain may be attached to the rest of the molecule through any two carbons within the chain.

"Amino acid residue" refers to the $R^{10}$ alkylene linking group between the nitrogen atom and the carboxy atom in a —$C(O)$—$R^{10}$—$N(R^7)_2$ or a —$N(R^7)$—$R^{10}$—$C(O)OR^7$ group that is substituted by the various "side chains" of known amino acids. For example, amino acid residues of α-amino acids include the α-carbon (to which the carboxy group and the nitrogen atom is attached) and the side chain. Thus, the amino acid residue of alanine is —$C(CH_3)$—; the amino acid residue of serine is —$C(CH_2OH)$—, and so forth. The term "amino acids" is intended to include α-amino acids, β-amino acids, γ-amino acids, and so forth, and all optical isomers thereof.

"Acetamido" refers to the radical —$N(H)C(O)CH_3$.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, alkenyl, alkynyl, halo, haloalkyl, haloalkenyl, cyano, nitro, aryl, aralkyl, aralkenyl, cycloalkyl, cycloalkylalkyl, cycloalkylalkenyl, heterocyclyl, heterocyclylalkyl, —$R^8$—$OR^7$, —$R^8$—O—$R^9$—$C(O)OR^7$, —$R^8$—$N(R^7)_2$, —$R^8$—$C(O)R^7$, —$R^8$—C(O)$OR^7$, —$R^8$—$C(O)N(R^7)_2$, —$R^8$—$N(R^7)C(O)OR^7$, —$R^8$—$N(R^7)C(O)R^7$, —$R^8$—$S(O)_pR^7$ (where p is 0 to 2), —$R^8$—$S(O)_pN(R^7)_2$ (where p is 0 to 2), and —$R^8$—$N(R^7)C(O)$—$R^8$—$N(R^7)_2$ where each $R^7$, $R^8$ and $R^9$ is as defined above in the Summary of the Invention.

"Cycloalkylalkyl" refers to a radical of the formula —$R_aR_d$ where $R_a$ is an alkyl radical as defined above and $R_d$ is a cycloalkyl radical as defined above. The alkyl radical and the cycloalkyl radical may be optionally substituted as defined above.

"Cycloalkylalkenyl" refers to a radical of the formula —$R_fR_d$ where $R_f$ is an alkenyl radical as defined above and $R_d$ is a cycloalkyl radical as defined above. The alkenyl radical and the cycloalkyl radical may be optionally substituted as defined above.

"Cyclic ureido groups" refers to optionally substituted heterocyclyl radicals as defined below which contain a ureido group, i.e. —N(H)—C(O)—N(H)—, within the ring, such as imidazolidinone, hydantoin, parabanic acid, trimethyleneurea, dihydrouracil, barbituric acid, alloxan, diazapan-2-one, diazapan-2,7-dione, diazapan-2,6-dione, and diazapan-2,5,7-trione, and the like. The cylic ureido group is attached to the rest of the molecule through a nitrogen atom in the ureido group. Other cyclic ureido groups include those radicals of the formula —$N(R^{7a})R_g$ where $R^{7a}$ is hydrogen or alkyl and $R_g$ is an optionally substituted heterocyclyl radical as defined below selected from the following formulae:

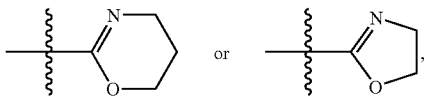

i.e., dihydrooxazine or dihydrooxazole, respectively.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above, e.g., 2-bromoethenyl, 3-bromoprop-1-enyl, and the like.

"Haloalkoxy" refers to a radical of the formula —$OR_c$ where $R_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. Examples of such heterocyclyl radicals include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl; carbazolyl, cinnolinyl, dioxolanyl, dibenzofuranyl, decahydroisoquinolyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, alkenyl, alkynyl, halo, haloalkyl, haloalkenyl, cyano, nitro, aryl, aralkyl, aralkenyl, cycloalkyl, cycloalkylalkyl, cycloalkylalkenyl, heterocyclyl, heterocyclylalkyl, —$R^8$—$OR^7$, —$R^8$—O—$R^9$—$C(O)OR^7$, —$R^8$—$N(R^7)_2$, —$R^8$—$C(O)R^7$, —$R^8$—$C(O)OR^7$, —$R^8$—$C(O)N(R^7)_2$, —$R^8$—$N(R^7)C(O)OR^7$, —$R^8$—$N(R^7)C(O)R^7$, —$R^8$—$S(O)_pR^7$ (where p is 0 to 2), —$R^8$—$S(O)_pN(R^7)_2$ (where p is 0 to 2), and —$R^8$—$N(R^7)C(O)$—$R^8$—$N(R^7)_2$ where each $R^7$, $R^8$ and $R^9$ is as defined above in the Summary of the Invention. Preferred heterocyclyl radicals are N-heterocyclyl radicals, i.e., heterocyclyl radicals as defined that contain at least one nitrogen atom. Examples of such preferred N-heterocyclyl radicals include pyrrolyl, pyrrolidinyl, imidazolyl, imidazolinyl, pyridinyl, piperidinyl, oxazolyl, oxazolidinyl, pyrazinyl, piperazinyl, morpholinyl, and pyrimidinyl.

"Heterocyclylalkyl" refers to a radical of the formula —$R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above. Preferred heterocyclylalkyl radicals are those heterocyclylalkyl radicals as defined above where $R_e$ is a preferred N-heterocyclyl radical as defined above.

"Hydroxyalkyl" refers to a radical of the formula —$R_aOH$ where $R_a$ is an alkyl radical as defined above and the hydroxy group can be on any carbon of the alkyl group.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7–9, 21–24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Therapeutically effective amount" refers to that amount of a compound of formula (I) or formula (II) which, when administered to a mammal, preferably a human, is sufficient to effect treatment, as defined below, for a disease-state alleviated by the inhibition of PDK-1 acitivity, such as cancer. The amount of a compound of formula (I) or formula (II) which constitutes a "therapeutically effective amount" will vary depending on the compound, the condition and its severity, and the age of the mammal to be treated, but can be determined routinely by one of ordinary skill in the art having regard to his own knowledge and to this disclosure.

"Treating" or "treatment" as used herein covers the treatment of disease-states alleviated by the inhibition of PDK-1 activity, such as cancer, as disclosed herein, in a mammal, preferably a human, and includes:

(i) preventing the disease-state from occurring in a mammal, in particular, when such mammal is predisposed to the disease-state but has not yet been diagnosed as having it;

(ii) inhibiting the disease-state, i.e., arresting its development; or (iii) relieving the disease-state, i.e., causing regression of the condition.

The compounds of formula (I) or formula (II), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)- isomers may be prepared using chiral synthons or chiral reagents, or resolved using conventional techniques, such as reverse phase HPLC. When the formulae described herein contain olefinic double bonds or other centers of geometric asymmetry, unless specified otherwise, it is intended that the formulae include both E and Z geometric isomers, as well as all tautomeric forms. In addition, all compound names herein, unless specified otherwise, are intended to include all single enantiomers, diastereomers, and mixtures thereof, as well as racemic and non-racemic mixtures.

The nomenclature used herein for the compounds of formula (I) or formula (II) is a modified form of the I.U.P.A.C. nomenclature system wherein the compounds are named herein as derivatives of the indolinone central moiety.

For example, a compound of formula (I) wherein m is 1, n is 1, A is oxygen, $R^1$ is —$CH_3$, $R^2$ is —N(H)C(O)$NH_2$, $R^3$ and $R^5$ are each hydrogen and $R^6$ is —$CH_2$N(H)C(O)—$CH_2$—C(O)OH, i.e., the compound of the following formula:

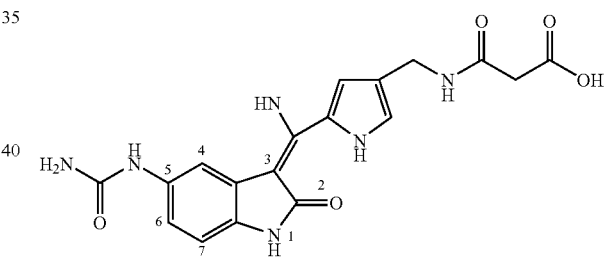

is named herein as 5-ureido-3-[1-(4-(carboxyacetamido)methylpyrrol-2-yl)ethylidene]indolin-2-one.

Utility of the Compounds of the Invention

The compounds of the invention block the activity of PDK-1 directly or block the PDK-1 mediated activation of AKT and are therefore useful in treating a variety of disease-states associated with either PDK-1 or AKT activity. In particular, the compounds of the invention are useful in treating cancer by inhibiting processes critical for tumor progression, including cell proliferation, survival, and tumor angiogenesis (Testa, J. R. and A. Bellacosa, "AKT plays a central role in tumorigenesis," *Proc. Nat. Acad. Sci. USA* 2001), Vol. 98, No. 20, pp. 10983–5; and Vivanco, I. and C. L. Sawyers, "The phosphatidylinositol 3-Kinase AKT pathway in human cancer," *Nat. Rev. Cancer* (2002), Vol. 2, No. 7, pp. 489–501).

Furthermore, the compounds of the invention are expected to sensitize tumors to the effects of other chemotherapeutic agents and radiation (Page, C. et al., "Overexpression of Akt/AKT can modulate chemotherapy-induced apoptosis," *Anticancer Res.* (2000), Vol. 20, No. 1A, pp. 407–16; and Brognard, J. et al., "Akt/protein kinase B is constitutively active in non-small cell lung cancer cells and promotes cellular survival and resistance to chemotherapy and radiation," *Cancer Res.* (2001), Vol. 61, No. 10, pp. 3986–97).

In addition, the compounds of the invention, as inhibitors of AKT activation, are useful in the treatment of tuberous sclerosis and are useful as modulators of the immune response (see, e.g., Cantrell, D., "Protein kinase B (Akt) regulation and function in T lymphocytes," *Semin. Immunol.* (2002), Vol. 14, No. 1, pp. 19–26) and for the treatment of autoimmune diseases such as rheumatoid arthritis and multiple sclerosis.

Testing of the Compounds of the Invention

The compounds of the invention may be tested by known in vitro and in vivo assays, or by the assays described herein, in order to determine their ability to inhibit the activity of PDK-1.

The compounds of the invention, for example, potently block an assay in which PDK-1 mediates the activation of AKT, whose activity is measured in the assay. The compounds, therefore, are either blocking the assay by inhibiting the PDK-1 enzyme activity, the AKT enzyme activity, or the activation of AKT by PDK-1. In addition, as described in detail below, the compounds of the invention block colony formation and/or growth of PC-3 prostate and MDA-468 breast cancer cells in soft agar, which is an in vitro measure of potential anti-tumor activity.

Administration of the Compounds and Pharmaceutical Compositions of the Invention Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington's Pharmaceutical Sciences,* 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disorder or condition associated with PDK-1 activity in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

Whether in solid, liquid or gaseous form, the pharmaceutical composition of the present invention may contain one or more known pharmacological agents used in the treatment of disease-states alleviated by the inhibition of PDK-1 activity, such as cancer.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

Preferred Embodiments of the Invention

Of the compounds of formula (I) set forth above in the Summary of the Invention, a preferred group of compounds are those compounds wherein:

m is 1 to 4;

n is 0 to 3;

A is oxygen;

$R^1$ is hydrogen or alkyl; or $R^1$ is aryl (optionally substituted by one or more substituents selected from the group consisting of —$R^8$—$OR^7$, —$R^8$—$N(R^7)_2$, —$R^8$—$C(O)N(R^7)_2$, —$R^8$—$N(R^7)C(O)N(R^7)_2$, —$R^8$—$N(R^7)C(O)$—$R^9$—$N(R^7)_2$ and —$R^8$—$N(R^7)C(O)OR^7$); or $R^1$ is heterocyclyl (optionally substituted by one or more substituents selected from the group consisting of alkyl, —$R^8$—$OR^7$, —$R^8$—$N(R^7)_2$, —$R^8$—$N(R^7)C(O)N(R^7)_2$ and —$R^8$—$N(R^7)C(O)$—$R^9$—$N(R^7)_2$); or $R^1$ is heterocyclylalkyl (optionally substituted by one or more substituents selected from the group consisting of alkyl and —$R^8$—$OR^7$);

each $R^2$ is independently selected from the group consisting of heterocyclyl, —$R^8$—$S(O)_tN(R^7)_2$ (where t is 1 or 2), —$R^8$—$N(R^7)_2$, —$R^8$—$N(R^7)S(O)_tN(R^7)_2$ (where t is 1 or 2), —$R^8$—$N(R^7)S(O)_tN(R^7)C(O)OR^7$ (where t is 1 or 2), —$R^8$—$N(R^7)C(O)R^7$, —$R^8$—$N(R^7)$—$R^8$—$C(O)OR^7$, —$R^8$—$N(R^7)C(O)N(R^7)_2$, —$R^8$—$N(R^7)C(O)$—$R^9$—$N(R^7)_2$, —$R^8$—$N(R^7)$—$R^9C(O)N(R^7)_2$, —$R^8$—$N(R^7)C(O)$—$R^8$—$N(R^7)$—$R^8$—$C(O)OR^7$, —$R^8$—$N(R^7)C(O)$—$R^8$—$N(R^7)$—$R^8$—$C(O)$—$R^8$—$N(R^7)_2$, —$N(R^7)C(=NR^7)N(R^7)_2$, and —$R^8$—$N=C(R^7)_2$;

$R^3$ is hydrogen;

$R^5$ is hydrogen or alkyl;

each $R^6$ is independently selected from the group consisting of halo, alkyl, —$R^8$—$C(O)R^7$, —$R^8$—$N(R^7)_2$, —$R^8$—$C(O)OR^7$, —$R^8$—$C(O)N(R^7)_2$, —$R^8$—$N(R^7)$—$R^8$—$C(O)OR^7$, —$R^8$—$N(R^7)C(O)R^7$, —$R^8$—$C(O)$—$R^9$—$C(O)OR^7$, —$R^8$—$N(R^7)C(O)N(R^7)_2$, —$R^8$—$N(R^7)C(O)$—$R^9$—$N(R^7)_2$, —$R^8$—$N(R^7)C(O)$—$R^9$—$C(O)OR^7$, —$R^8$—$N(R^7)C(O)$—$R^8$—$N(R^7)$—$R^8$—$C(O)OR^7$, heterocyclyl (optionally substituted by one or more substituents selected from the group consisting of alkyl, halo, haloalkyl, cyano, nitro, —$R^8$—$OR^7$, —$R^8$—O—$R^9$—C(O)$OR^7$, —$R^8$—N($R^7$)$_2$, —$R^8$—C(O)$R^7$, —$R^8$—C(O)$OR^7$, —$R^8$—C(O)N($R^7$)$_2$, —$R^8$—N($R^7$)C(O)$OR^7$, —$R^8$—N($R^7$)C(O)$R^7$, —$R^8$—S(O)$_p$$R^7$ (where p is 0 to 2), —$R^8$—S(O)$_p$N($R^7$)$_2$ (where p is 0 to 2), and —$R^8$—N($R^7$)C(O)—$R^8$—N($R^7$)$_2$) and aryl (optionally substituted by one or more substituents selected from the group consisting of alkyl, —$R^8$—$OR^7$, —$R^8$—O—$R^9$—C(O)$OR^7$, —$R^8$—C(O)$R^7$, —$R^8$—C(O)$OR^7$, —$R^8$—C(O)N($R^7$)$_2$, —$R^8$—N($R^7$)C(O)$R^7$, —$R^8$—N($R^7$)C(O)$OR^7$, —$R^8$—N($R^7$)$_2$, —$R^8$—N($R^7$)C(O)—$R^8$—N($R^7$)—$R^8$—C(O)$OR^7$, and —$R^8$—S(O)$_t$$R^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

Of this preferred group of compounds, a preferred subgroup of compounds is that subgroup of compounds wherein:

m is 1;

n is 0 or 3;

A is oxygen;

$R^1$ is hydrogen or alkyl;

$R^2$ is —$R^8$—S(O)$_t$N($R^7$)$_2$ (where t is 1 or 2), —$R^8$—N($R^7$)C(O)$R^7$, —$R^8$—N($R^7$)—$R^8$—C(O)$OR^7$, —$R^8$—N($R^7$)C(O)N($R^7$)$_2$, —$R^8$—N($R^7$)—$R^9$—C(O)N($R^7$)$_2$, or —$R^8$—N($R^7$)C(O)—$R^9$—N($R^7$)$_2$;

$R^3$ is hydrogen;

$R^5$ is hydrogen or alkyl;

$R^6$ is independently selected from the group consisting of halo, alkyl, —$R^8$—C(O)$R^7$, —$R^8$—N($R^7$)$_2$, —$R^8$—C(O)$OR^7$, —$R^8$—C(O)N($R^7$)$_2$, —$R^8$—N($R^7$)—$R^8$—C(O)$OR^7$, —$R^8$—N($R^7$)C(O)$R^7$, —$R^8$—C(O)—$R^9$—C(O)$OR^7$, —$R^8$—N($R^7$)C(O)N($R^7$)$_2$, —$R^8$—N($R^7$)C(O)—$R^9$—N($R^7$)$_2$, —$R^8$—N($R^7$)C(O)—$R^9$—C(O)$OR^7$, —$R^8$—N($R^7$)C(O)—$R^8$—N($R^7$)—$R^8$—C(O)$OR^7$, heterocyclyl (optionally substituted by one or more substituents selected from the group consisting of alkyl, halo, haloalkyl, cyano, nitro, —$R^8$—$OR^7$, —$R^8$—O—$R^9$—C(O)$OR^7$, —$R^8$—N($R^7$)$_2$, —$R^8$—C(O)$R^7$, —$R^8$—C(O)$OR^7$, —$R^8$—C(O)N($R^7$)$_2$, —$R^8$—N($R^7$)C(O)$OR^7$, —$R^8$—N($R^7$)C(O)$R^7$, —$R^8$—S(O)$_p$ $R^7$ (where p is 0 to 2), —$R^8$—S(O)$_p$N($R^7$)$_2$ (where p is 0 to 2), and —$R^8$—N($R^7$)C(O)—$R^8$—N($R^7$)$_2$) and aryl (optionally substituted by one or more substituents selected from the group consisting of —$R^8$—$OR^7$, —$R^8$—$R^9$—C(O)$OR^7$, —$R^8$—C(O)$OR^7$, —$R^8$—C(O)N($R^7$)$_2$, —$R^8$—N($R^7$)C(O)$R^7$, —$R^8$—N($R^7$)C(O)$OR^7$, —$R^8$—N($R^7$)$_2$, —$R^8$—N($R^7$)C(O)—$R^8$—N($R^7$)—$R^8$—C(O)$OR^7$, and —$R^8$—S(O)$_t$$R^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

Of this preferred subgroup of compounds, a preferred class of compounds is that class of compounds wherein:

m is 1;

n is 0, 1, 2 or 3;

A is oxygen;

$R^1$ is hydrogen or alkyl;

$R^2$ is —$R^8$—S(O)$_t$N($R^7$)$_2$ (where t is 1 or 2), —$R^8$—N($R^7$)C(O)$R^7$, —$R^8$—N($R^7$)—$R^8$—C(O)$OR^7$, —$R^8$—N($R^7$)C(O)N($R^7$)$_2$, —$R^8$—N($R^7$)—$R^9$—C(O)N($R^7$)$_2$, or —$R^8$—N($R^7$)C(O)—$R^9$—N($R^7$)$_2$;

$R^3$ is hydrogen;

$R^5$ is hydrogen or alkyl;

each $R^5$ is independently selected from the group consisting of halo, alkyl, —$R^8$—C(O)$R^7$, —$R^8$—C(O)$OR^7$, —$R^8$—C(O)N($R^7$)$_2$, and —$R^8$—C(O)—$R^9$—C(O)$OR^7$;

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and $R^9$ is a straight or branched alkylene chain.

Of this preferred class of compounds, preferred compounds are those compounds selected from the group consisting of the following:

5-acetamido-3-[(pyrrol-2-yl)methylene]indolin-2-one;
5-ureido-3-[(pyrrol-2-yl)methylene]indolin-2-one;
5-trifluoroacetamido-3-[(pyrrol-2-yl)methylene]indolin-2-one;
4-acetamido-3-[(pyrrol-2-yl)methylene]indolin-2-one;
5-ureido-3-[1-(pyrrol-2-yl)ethylidene]indolin-2-one;
5-(pyrrolidin-1-yl)acetamido-3-[(pyrrol-2-yl)methylene]indolin-2-one;
5-(N'-ethylureido)-3-[1-(pyrrol-2-yl)ethylidene]indolin-2-one;
5-(N'-phenylureido)-3-[1-(pyrrol-2-yl)ethylidene]indolin-2-one;
5-acetamidomethyl-3-[1-(pyrrol-2-yl)ethylidene]indolin-2-one;
5-(pyridin-3-yl)carbonylamino-3-[1-(pyrrol-2-yl)ethylidene]indolin-2-one;
5-(1,1-dimethylethoxy)carbonylaminomethyl-3-[1-(pyrrol-2-yl)ethylidene]indolin-2-one;
5-(ureido)methyl-3-[1-(pyrrol-2-yl)ethylidene]indolin-2-one;
5-(pyridin-4-yl)carbonylamino-3-[1-(pyrrol-2-yl)ethylidene]indolin-2-one;
5-ureido-3-[1-(pyrrol-2-yl)propylidene]indolin-2-one;
5-aminoacetamido-3-[1-(pyrrol-2-yl)ethylidene]indolin-2-one;
5-ureido-3-[(4-bromopyrrol-2-yl)methylene]indolin-2-one;
5-ureido-3-[(4-(piperidin-1-ylmethyl)carbonylpyrrol-2-yl)methylene]indolin-2-one;
5-ethoxycarbonylmethylamino-3-[1-(pyrrol-2-yl)ethylidene]indolin-2-one;
5-aminocarbonylmethylamino-3-[1-(pyrrol-2-yl)ethylidene]indolin-2-one;
5-(N-ethylureido)-3-[1-(pyrrol-2-yl)ethylidene]indolin-2-one;
5-ureido-3-[(4-((4-methylpiperazin-1-yl)methylcarbonyl)pyrrol-2-yl)methylene]indolin-2-one;
5-ureido-3-[(4-(2-ethoxycarbonylethyl)carbonylpyrrol-2-yl)methylene]indolin-2-one;
5-ureido-3-[(4-(2-carboxyethyl)carbonylpyrrol-2-yl)methylene]indolin-2-one;
5-(4-aminopiperidin-1-ylcarbonylamino)-3-[1-(pyrrol-2-yl)ethylidene]indolin-2-one;
5-ureido-3-[(4-(piperazin-1-ylmethylcarbonyl)pyrrol-2-yl)methylene]indolin-2-one;
5-ureido-3-[(4-ethoxycarbonylpyrrol-2-yl)methylene]indolin-2-one;
5-ureido-3-[(4-carboxypyrrol-2-yl)methylene]indolin-2-one;

5-ureido-3-[(4-(2-morpholin-4-ylethyl)aminocarbonylpyrrol-2-yl)methylene]indolin-2-one;
5-ureido-3-[(4-(2-piperidin-1-ylethyl)aminocarbonylpyrrol-2-yl)methylene]indolin-2-one;
5-ureido-3-[(4-(pyridin-3-ylmethyl)aminocarbonylpyrrol-2-yl)methylene]indolin-2-one;
5-ureido-3-[(4-(3-piperidin-1-ylpropyl)aminocarbonylpyrrol-2-yl)methylene]indolin-2-one;
5-ureido-3-[(3-methyl-4-carboxypyrrol-2-yl)methylene]indolin-2-one;
5-acetamido-3-[1-(pyrrol-2-yl)ethylidene]indolin-2-one;
4-ethoxycarbonylmethylamino-3-[(pyrrol-2-yl)methylene]indolin-2-one;
5-ureido-3-[(4-(2-dimethylaminoethyl)aminocarbonylpyrrol-2-yl)methylene]indolin-2-one;
5-ureido-3-[(3-methyl-4-(2-piperidin-1-ylethyl)aminocarbonylpyrrol-2-yl)methylene]indolin-2-one;
5-ureido-3-[(4-(2-(imidazol-4-yl)ethyl)aminocarbonylpyrrol-2-yl)methylene]indolin-2-one;
5-ureido-3-[(4-(2-(pyridin-4-yl)ethyl)aminocarbonylpyrrol-2-yl)methylene]indolin-2-one;
5-ureido-3-[(4-((3R)-3-(dimethylamino)pyrrolidin-4-yl)carbonylpyrrol-2-yl)methylene]indolin-2-one;
5-ureido-3-[(4-((3S)-3-(dimethylamino)pyrrolidin-4-yl)carbonylpyrrol-2-yl)methylene]indolin-2-one;
5-ureido-3-[(4-(3-(pyrrolidin-1-yl)propyl)aminocarbonylpyrrol-2-yl)methylene]indolin-2-one;
5-ureido-3-[(4-(4-(pyrrolidin-1-yl)butyl)aminocarbonylpyrrol-2-yl)methylene]indolin-2-one;
5-ureido-3-[(4-(4-methylpiperazin-1-yl)carbonylpyrrol-2-yl)methylene]indolin-2-one;
5-aminosulfonyl-3-[(4-carboxy-3-methylpyrrol-2-yl)methylene]indolin-2-one;
5-ureido-3-[(4-(2-carboxyethyl)-3,5-dimethylpyrrol-2-yl)methylene]indolin-2-one;
5-aminosulfonyl-3-[(3-methyl-4-(3-(piperidin-1-yl)propyl)aminocarbonylpyrrol-2-yl)methylene]indolin-2-one;
5-ureido-3-[(4-(2-(4-methylpiperazin-1-yl)carbonylethyl)-3,5-dimethylpyrrol-2-yl)methylene]indolin-2-one;
5-ureido-3-[(4-(2-carboxyethyl)-3-methylpyrrol-2-yl)methylene]indolin-2-one;
5-ureido-3-[(4-(2-(pyridin-3-ylmethyl)aminocarbonylethyl)-3-methylpyrrol-2-yl)methylene]indolin-2-one;
5-ureido-3-[(4-(2-(pyridin-4-yl)aminocarbonylethyl)-3-methylpyrrol-2-yl)methylene]indolin-2-one;
5-ureido-3-[(4-(2-(2-piperidin-1-ylethyl)aminocarbonylethyl)-3-methylpyrrol-2-yl)methylene]indolin-2-one; and
5-ureido-3-[(4-(2-(4-methylpiperazin-1-yl)carbonylethyl)-3-methylpyrrol-2-yl)methylene]indolin-2-one.

Of the preferred group of compounds described above, another preferred subgroup of compounds is that subgroup of compounds wherein:

m is 1;
n is 0 or 1;
A is oxygen;
$R^1$ is hydrogen or alkyl;
$R^2$ is —$R^8N(R^7)_2$, —$R^8$—$N(R^7)C(O)R^7$, —$R^8$—$N(R^7)$—$R^8$—$C(O)OR^7$, —$R^8$—$N(R^7)C(O)N(R^7)_2$, —$R^8$—$N(R^7)$—$R^9$—$C(O)N(R^7)_2$, or —$R^8$—$N(R^7)C(O)$—$R^9$—$N(R^7)_2$;
$R^3$ is hydrogen;
$R^5$ is hydrogen or alkyl;
$R^6$ is independently selected from the group consisting of —$R^8$—$N(R^7)_2$, —$R^8$—$N(R^7)$—$R^8$—$C(O)OR^7$, —$R^8$—$N(R^7)C(O)R^7$, —$R^8$—$N(R^7)C(O)N(R^7)_2$, —$R^8$—$N(R^7)C(O)$—$R^9$—$N(R^7)_2$, —$R^8$—$N(R^7)C(O)$—$R^9$—$C(O)OR^7$, and —$R^8$—$N(R^7)C(O)$—$R^8$—$N(R^7)$—$R^8$—$C(O)OR^7$;

each $R^7$ is independently hydrogen, optionally substituted alkyl, haloalkyl, optionally substituted aryl, optionally substituted aralkyl, optionally substituted heterocyclyl, or optionally substituted heterocyclylalkyl;
each $R^8$ is a bond or a straight or branched alkylene chain; and
each $R^9$ is a straight or branched alkylene chain.

Of this preferred subgroup of compounds, preferred compounds are those compounds selected from the group consisting of the following:

5-ureido-3-[1-(4-(1,1-dimethylethoxycarbonylaminomethyl)pyrrol-2-yl)ethylidene]indolin-2-one;
5-ureido-3-[1-(4-(aminomethyl)pyrrol-2-yl)ethylidene]indolin-2-one;
5-ureido-3-[1-(4-(acetamidomethyl)pyrrol-2-yl)ethylidene]indolin-2-one;
5-ureido-3-[1-(4-(((1,1-dimethylethoxycarbonylamino)methyl)carbonylamino-methyl)pyrrol-2-yl)ethylidene]indolin-2-one;
5-ureido-3-[1-(4-(aminoacetamido)methylpyrrol-2-yl)ethylidene]indolin-2-one;
5-ureido-3-[1-(4-(pyridin-4-ylcarbonylamino)methylpyrrol-2-yl)ethylidene]indolin-2-one;
5-ureido-3-[1-(4-(hydroxyacetamido)methylpyrrol-2-yl)ethylidene]indolin-2-one;
5-ureido-3-[1-(4-(1-(1,1-dimethylethoxycarbonyl)piperidin-4-ylcarbonylamino)methylpyrrol-2-yl)ethylidene]indolin-2-one;
5-ureido-3-[1-(4-(piperidin-4-ylcarbonylamino)methylpyrrol-2-yl)ethylidene]indolin-2-one;
5-ureido-3-[1-(4-((1,1-dimethylethoxycarbonyl)-acetamido)methylpyrrol-2-yl)ethylidene]indolin-2-one;
5-ureido-3-[1-(4-(1-(1,1-dimethylethoxycarbonyl)pyrrolidin-2-ylcarbonylamino)methylpyrrol-2-yl)ethylidene]indolin-2-one;
5-ureido-3-[1-(4-((2-(1,1-dimethylethoxycarbonylamino)ethyl)carbonylamino)-methylpyrrol-2-yl)ethylidene]indolin-2-one;
5-ureido-3-[1-(4-(carboxyacetamido)methylpyrrol-2-yl)ethylidene]indolin-2-one;
5-ureido-3-[1-(4-(pyrrolidin-2-ylcarbonylamino)methylpyrrol-2-yl)ethylidene]indolin-2-one;
5-ureido-3-[1-(4-(pyridin-3-ylcarbonylamino)methylpyrrol-2-yl)ethylidene]indolin-2-one;
5-ureido-3-[1-(4-((2-aminoethyl)carbonylamino)methylpyrrol-2-yl)ethylidene]indolin-2-one;
5-ureido-3-[1-((4-((1,2-diaminoethyl)carbonylamino)methylpyrrol-2-yl)ethylidene]indolin-2-one;
5-ureido-3-[1-(4-((1-amino-2-methoxycarbonylethyl)carbonylamino)methylpyrrol-2-yl)ethylidene]indolin-2-one;
5-ureido-3-[1-(4-((3-amino-1-acetylaminoprop-1-yl)carbonylamino)methylpyrrol-2-yl)ethylidene]indolin-2-one;
5-ureido-3-[1-(4-(piperazin-2-ylcarbonylamino)methylpyrrol-2-yl)ethylidene]indolin-2-one;
5-ureido-3-[1-(4-(1-methylpiperidin-4-ylcarbonylamino)methylpyrrol-2-yl)ethylidene]indolin-2-one;
5-ureido-3-[1-(4-(2-(piperidin-1-yl)ethylcarbonylamino)methylpyrrol-2-yl)ethylidene]indolin-2-one;
5-ureido-3-[(4-((morpholin-4-ylmethyl)carbonylaminomethyl)pyrrol-2-yl)methylene]indolin-2-one;
5-ureido-3-[(4-((piperidin-1-yl)acetamido)methylpyrrol-2-yl)methylene]indolin-2-one;
5-acetamido-3-[1-(4-aminomethylpyrrol-2-yl)ethylidene]indolin-2-one;
5-amino-3-[1-(4-(2-aminoethylcarbamylmethyl)pyrrol-2-yl)ethylidene]indolin-2-one; and 5-acetamido-3-[1-(4-(2-aminoethylcarbamylmethyl)pyrrol-2-yl)ethylidene]indolin-2-one.

Of the preferred group of compounds described above, another preferred subgroup of compounds is that subgroup of compounds wherein:

m is 1;
n is 0 or 1;
A is oxygen;
$R^1$ is hydrogen or alkyl;
$R^2$ is $-R^8-N(R^7)C(O)R^7$, $-R^8-N(R^7)-R^8-C(O)OR^7$, $-R^8-N(R^7)_2$, $-R^8-C(O)R^7$, $-R^8-N(R^7)-R^9-C(O)N(R^7)_2$, or $-R^8-N(R^7)C(O)-R^9-N(R^7)_2$;
$R^3$ is hydrogen;
$R^5$ is hydrogen or alkyl;
$R^6$ is independently selected from the group consisting of heterocyclyl (optionally substituted by one or more substituents selected from the group consisting of alkyl, halo, haloalkyl, cyano, nitro, $-R^8-OR^7$, $-R^8-O-R^9-C(O)OR^7$, $-R^8-N(R^7)_2$, $-R^8-C(O)R^7$, $-R^8-C(O)OR^7$, $-R^8-C(O)N(R^7)_2$, $-R^8-N(R^7)C(O)OR^7$, $-R^8-N(R^7)C(O)R^7$, $-R^8-S(O)_pR^7$ (where p is 0 to 2), $-R^8-S(O)_pN(R^7)_2$ (where p is 0 to 2), and $-R^8-N(R^7)C(O)-R^8-N(R^7)_2$) and aryl (optionally substituted by one or more substituents selected from the group consisting of $-R^8-OR^7$, $-R^8-O-R^9-C(O)OR^7$, $-R^8-C(O)R^7$, $-R^8-C(O)OR^7$, $-R^8-C(O)N(R^7)_2$, $-R^8-N(R^7)C(O)R^7$, $-R^8-N(R^7)C(O)OR^7$, $-R^8-N(R^7)_2$, $-R^8-N(R^7)C(O)-R^8-N(R^7)-R^8-C(O)OR^7$, and $-R^8-S(O)_tR^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

Of this preferred subgroup of compounds, preferred compounds are those compounds selected from the group consisting of the following:

5-ureido-3-[(4-(3-methoxyphenyl)pyrrol-2-yl)methylene]indolin-2-one;
5-ureido-3-[(4-(4-methoxyphenyl)pyrrol-2-yl)methylene]indolin-2-one;
5-ureido-3-[(4-(3-hydroxyphenyl)pyrrol-2-yl)methylene]indolin-2-one;
5-ureido-3-[(4-(3-acetylaminophenyl)pyrrol-2-yl)methylene]indolin-2-one;
5-ureido-3-[(4-(3-carboxyphenyl)pyrrol-2-yl)methylene]indolin-2-one;
5-ureido-3-[(4-(pyridin-3-yl)pyrrol-2-yl)methylene]indolin-2-one;
5-ureido-3-[(4-(3-(2-morpholin-4-ylethoxy)phenyl)pyrrol-2-yl)methylene]indolin-2-one;
5-ureido-3-[(4-(3-methoxycarbonylmethoxyphenyl)pyrrol-2-yl)methylene]indolin-2-one;
5-ureido-3-[(4-(4-methoxycarbonylphenyl)pyrrol-2-yl)methylene]indolin-2-one;
5-ureido-3-[(4-(3-aminocarbonylphenyl)pyrrol-2-yl)methylene]indolin-2-one;
5-ureido-3-[(4-(3,4-dimethoxyphenyl)pyrrol-2-yl)methylene]indolin-2-one;
5-ureido-3-[(4-(4-carboxyphenyl)pyrrol-2-yl)methylene]indolin-2-one;
5-ureido-3-[(4-(3,4-dihydroxyphenyl)pyrrol-2-yl)methylene]indolin-2-one;
5-ureido-3-[(4-(4-(1,1-dimethylethoxycarbonylamino)methylphenyl)pyrrol-2-yl)methylene]indolin-2-one;
5-ureido-3-[(4-(3-aminomethylphenyl)pyrrol-2-yl)methylene]indolin-2-one;
5-ureido-3-[(4-(3-acetamidomethylphenyl)pyrrol-2-yl)methylene]indolin-2-one;
5-ureido-3-[(4-(3-(2-piperidin-1-ylethyl)aminocarbonylphenyl)pyrrol-2-yl)methylene]indolin-2-one;
5-ureido-3-[(4-(3-(1,1-dimethylethoxycarbonyl)aminoacetamidomethylphenyl)pyrrol-2-yl)methylene]indolin-2-one;
5-ureido-3-[(4-(4-methylsulfonylphenyl)pyrrol-2-yl)methylene]indolin-2-one;
5-ureido-3-[(4-(4-(2-piperidin-1-ylethyl)aminocarbonylphenyl)pyrrol-2-yl)methylene]indolin-2-one;
5-ureido-3-[(4-(4-(2-dimethylaminoethyl)aminocarbonylphenyl)pyrrol-2-yl)methylene]indolin-2-one;
5-ureido-3-[(4-(4-(4-methylpiperazin-1-yl)carbonylphenyl)pyrrol-2-yl)methylene]indolin-2-one;
5-ureido-3-[(4-(3-(2-dimethylaminoethyl)aminocarbonylphenyl)pyrrol-2-yl)methylene]indolin-2-one;
5-ureido-3-[(4-(3-(4-methylpiperazin-1-yl)carbonylphenyl)pyrrol-2-yl)methylene]indolin-2-one;
5-ureido-3-[(4-(4-(3-hydroxypyrrolidin-1-yl)carbonylphenyl)pyrrol-2-yl)methylene]indolin-2-one;
5-ureido-3-[(4-(3-(3-hydroxypyrrolidin-1-yl)carbonylphenyl)pyrrol-2-yl)methylene]indolin-2-one;
5-ureido-3-[(4-(pyrimidin-5-yl)pyrrol-2-yl)methylene]indolin-2-one; and
5-ureido-3-[(4-(5-methoxypyridin-3-yl)pyrrol-2-yl)methylene]indolin-2-one.

Of the preferred group of compounds described above, another preferred subgroup of compounds is that subgroup of compounds wherein:

m is 1 to 2;
n is 0;
A is oxygen;
$R^1$ is aryl (optionally substituted by one or more substituents selected from the group consisting of $-R^8-OR^7$, $-R^8-N(R^7)_2$, $-R^8-C(O)N(R^7)_2$, $-R^8-N(R^7)C(O)N(R^7)_2$, $-R^8-N(R^7)C(O)-R^9-N(R^7)_2$ and $-R^8-N(R^7)C(O)OR^7$, or $R^1$ is heterocyclyl (optionally substituted by one or more substituents selected from the group consisting of alkyl, $-R^8-OR^7$, $-R^8-N(R^7)_2$, $-R^8-N(R^7)C(O)N(R^7)_2$ and $-R^8-N(R^7)C(O)-R^9-N(R^7)_2$), or $R^1$ is heterocyclylalkyl (optionally substituted by one or more substituents selected from the group consisting of alkyl and $-R^8-OR^7$);

each $R^2$ is independently selected from the group consisting of $-R^8-N(R^7)_2$, $-R^8-S(O)_tN(R^7)_2$ (where t is 1 or 2), $-R^8-N(R^7)C(O)N(R^7)_2$ and $-R^8-N(R^7)C(O)-R^9-N(R^7)_2$;

$R^3$ is hydrogen;
$R^5$ is hydrogen;
each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

Of this preferred subgroup of compounds, preferred compounds are those compounds selected from the group consisting of the following:

5-aminosulfonyl-3-[(pyrrol-2-yl)(phenyl)methylene]indolin-2-one;
5-ureido-3-[(pyrrol-2-yl)(pyridin-4-yl)methylene]indolin-2-one;

5-ureido-3-[(pyrrol-2-yl)(pyridin-3-yl)methylene]indolin-2-one;
5-ureido-3-[(pyrrol-2-yl)(4-methoxyphenyl)methylene]indolin-2-one;
5-ureido-3-[(pyrrol-2-yl)(3-aminophenyl)methylene]indolin-2-one;
5-ureido-3-[(pyrrol-2-yl)(3-(1,1-dimethylethoxycarbonylamino)phenyl)methylene]indolin-2-one;
5-ureido-3-[(pyrrol-2-yl)(2-methoxypyridin-5-yl)methylene]indolin-2-one;
5-amino-3-[(pyrrol-2-yl)(3-(5,5-dimethyl-1,3-dioxan-2-yl)prop-1-yl)methylene]indolin-2-one; and
5-ureido-3-[(pyrrol-2-yl)(3-aminoacetamidophenyl)-methylene]indolin-2-one.

Of the preferred group of compounds described above, another preferred subgroup of compounds is that subgroup of compounds wherein:
m is 1 to 4;
n is 0;
A is oxygen;
$R^1$ is hydrogen or alkyl;
each $R^2$ is independently selected from the group consisting of heterocyclyl, $-R^8-N(R^7)C(O)-R^8-N(R^7)-R^8-C(O)-R^8-N(R^7)_2$, $-R^8-N=C(R^7)_2$, $-R^8-N(R^7)C(O)-R^8-N(R^7)-R^8-C(O)OR^7$, $-N(R^7)C(=NR^7)N(R^7)_2$, $-R^8-N(R^7)S(O)_tN(R^7)_2$ (where t is 1 or 2), and $-R^8-N(R^7)S(O)_tN(R^7)C(O)OR^7$ (where t is 1 or 2);
$R^3$ is hydrogen;
$R^5$ is hydrogen or alkyl;
each $R^7$ is independently hydrogen, optionally substituted alkyl, haloalkyl, optionally substituted aryl, optionally substituted aralkyl, optionally substituted heterocyclyl, or optionally substituted heterocyclylalkyl;
each $R^8$ is a bond or a straight or branched alkylene chain.

Of this preferred subgroup of compounds, preferred compounds are those compounds selected from the group consisting of the following:
5-(N'-aminocarbonylureido)-3-[(pyrrol-2-yl)methylene]indolin-2-one;
5-tetrazol-5-yl-3-[(pyrrol-2-yl)methylene]indolin-2-one;
4-(pyrrol-2-yl)methyleneamino-3-[(pyrrol-2-yl)methylene]indolin-2-one;
5-(N'-(ethoxycarbonylmethyl)ureido)-3-[1-(pyrrol-2-yl)ethylidene]indolin-2-one;
5-((1-pyrrol-2-yl)ethylidene)aminomethyl-3-[1-(pyrrol-2-yl)ethylidene]indolin-2-one;
5-(2,4-dioxoimidazolidin-1-yl)-3-[1-(pyrrol-2-yl)ethylidene]indolin-2-one;
5-guanidino-3-[1-(pyrrol-2-yl)ethylidene]indolin-2-one;
5-aminosulfonylamino-3-[1-(pyrrol-2-yl)ethylidene]indolin-2-one; and
5-(1,1-dimethylethoxy)carbonylaminosulfonylamino-3-[1-(pyrrol-2-yl)ethylidene]indolin-2-one.

Of the compounds of formula (I) set forth above in the Summary of the Invention, another preferred group of compounds is that group of compounds wherein:
m is 1 to 4;
n is 0 or 1;
A is oxygen;
$R^1$ is hydrogen or alkyl;
each $R^2$ is independently selected from the group consisting of $-R^8-N(R^7)_2$ and $-R^8-N(R^7)S(O)_tR^7$ (where t is 1 or 2);
$R^3$ is hydrogen;
$R^5$ is hydrogen or alkyl;
$R^6$ is $-R^8-N(R^7)_2$;
each $R^7$ is independently hydrogen, optionally substituted alkyl, haloalkyl, optionally substituted aryl, optionally substituted aralkyl, optionally substituted heterocyclyl, or optionally substituted heterocyclylalkyl;
each $R^8$ is a bond or a straight or branched alkylene chain.

Of this group of compounds, preferred compounds are selected from the group consisting of the following:
6-amino-3-[(pyrrol-2-yl)methylene]indolin-2-one;
5-amino-3-[(pyrrol-2-yl)methylene]indolin-2-one;
5-methylsulfonylamino-3-[(pyrrol-2-yl)methylene]indolin-2-one;
5-aminomethyl-3-[(pyrrol-2-yl)methylene]indolin-2-one;
4-amino-3-[(pyrrol-2-yl)methylene]indolin-2-one;
5-amino-3-[1-(pyrrol-2-yl)ethylidene]indolin-2-one;
5-aminomethyl-3-[1-(pyrrol-2-yl)ethylidene]indolin-2-one;
5-(4,5-dihydrooxazol-2-ylamino)-3-[1-(pyrrol-2-yl)ethylidene]indolin-2-one; and
5-amino-3-[(4-(aminomethyl)pyrrol-2-yl)methylene]indolin-2-one.

Of the compounds of formula (I) set forth above in the Summary of the Invention, another preferred group of compounds is that group of compounds wherein:
m is 0 to 4;
n is 0 to 3;
A is oxygen;
$R^1$ is hydrogen, alkyl, $-C(O)OR^7$, or $-C(O)N(R^7)_2$;
each $R^2$ is independently selected from the group consisting of alkyl, halo, haloalkyl, cyano, $-R^8-OR^7$, $-R^8-C(O)OR^7$, $-R^8-C(O)N(R^7)_2$ and $-R^8-S(O)_tN(R^7)_2$ (where t is 1 or 2);
$R^3$ is hydrogen or alkyl;
$R^5$ is hydrogen or alkyl;
each $R^6$ is independently selected from the group consisting of alkyl and nitro;
each $R^7$ is independently hydrogen, optionally substituted alkyl, haloalkyl, optionally substituted aryl, optionally substituted aralkyl, optionally substituted heterocyclyl, or optionally substituted heterocyclylalkyl;
each $R^8$ is a bond or a straight or branched alkylene chain.

Of this group of compounds, preferred compounds are selected from the group consisting of the following:
6-chloro-3-[(pyrrol-2-yl)methylene]indolin-2-one;
5-bromo-3-[(pyrrol-2-yl)methylene]indolin-2-one;
6-fluoro-3-[(pyrrol-2-yl)methylene]indolin-2-one;
6-methyl-3-[((1-methyl)pyrrol-2-yl)methylene]indolin-2-one;
6-trifluoromethyl-3-[(1-methylpyrrol-2-yl)methylene]indolin-2-one;
5-methoxy-3-[(pyrrol-2-yl)methylene]indolin-2-one;
5,6-dimethoxy-3-[(pyrrol-2-yl)methylene]indolin-2-one;
4-methyl-3-[(pyrrol-2-yl)methylene]indolin-2-one;
7-methyl-3-[(pyrrol-2-yl)methylene]indolin-2-one;
5-hydroxy-3-[(pyrrol-2-yl)methylene]indolin-2-one;
5-methyl-3-[(pyrrol-2-yl)methylene]indolin-2-one;
6-carboxy-3-[(pyrrol-2-yl)methylene]indolin-2-one;
5-methoxy-3-[(5-ethylpyrrol-2-yl)methylene]indolin-2-one;
5-hydroxy-3-[(5-ethylpyrrol-2-yl)methylene]indolin-2-one;
5-aminosulfonyl-3-[(pyrrol-2-yl)methylene]indolin-2-one;
3-[(4-nitropyrrol-2-yl)methylene]indolin-2-one;
7-methoxy-3-[(pyrrol-2-yl)methylene]indolin-2-one;
7-hydroxy-3-[(pyrrol-2-yl)methylene]indolin-2-one;
4-methoxy-3-[(pyrrol-2-yl)methylene]indolin-2-one;
4-hydroxy-3-[(pyrrol-2-yl)methylene]indolin-2-one;
5-(2-hydroxyethyl)aminosulfonyl-3-[(pyrrol-2-yl)methylene]indolin-2-one;
6-methoxy-3-[(pyrrol-2-yl)methylene]indolin-2-one;
6-hydroxy-3-[(pyrrol-2-yl)methylene]indolin-2-one;

5-dimethylaminosulfonyl-3-[(pyrrol-2-yl)methylene]indolin-2-one;
5-methylaminosulfonyl-3-[(pyrrol-2-yl)methylene]indolin-2-one;
5-hydroxy-3-[1-(pyrrol-2-yl)ethylidene]indolin-2-one;
5-methoxy-3-[1-(pyrrol-2-yl)ethylidene]indolin-2-one;
5-methoxy-4-methyl-3-[(pyrrol-2-yl)methylene]indolin-2-one;
5-hydroxy-4-methyl-3-[(pyrrol-2-yl)methylene]indolin-2-one;
5,6-dihydroxy-3-[(pyrrol-2-yl)methylene]indolin-2-one;
5-carboxy-3-[(pyrrol-2-yl)methylene]indolin-2-one;
5-aminosulfonyl-3-[(1-pyrrol-2-yl)ethylidene]indolin-2-one;
5-hydroxy-3-[(4-methylpyrrol-2-yl)methylene]indolin-2-one;
5-phenylaminosulfonyl-3-[(pyrrol-2-yl)methylene]indolin-2-one;
5-hydroxy-3-[(5-methylpyrrol-2-yl)methylene]indolin-2-one;
5-hydroxy-3-[(3-methylpyrrol-2-yl)methylene]indolin-2-one;
5-methoxy-3-[(4-nitropyrrol-2-yl)methylene]indolin-2-one;
5-methoxycarbonyl-3-[(pyrrol-2-yl)methylene]indolin-2-one;
5-aminocarbonyl-3-[(pyrrol-2-yl)methylene]indolin-2-one;
5-methoxy-3-[(3,5-dimethylpyrrol-2-yl)methylene]indolin-2-one;
5-methoxy-1-methyl-3-[(pyrrol-2-yl)methylene]indolin-2-one;
5-hydroxy-1-methyl-3-[(pyrrol-2-yl)methylene]indolin-2-one;
5-hydroxy-3-[(3,5-dimethylpyrrol-2-yl)methylene]indolin-2-one;
4-carboxy-3-[(pyrrol-2-yl)methylene]indolin-2-one;
5-cyano-3-[(pyrrol-2-yl)methylene]indolin-2-one;
4-methoxy-5-methoxycarbonyl-7-chloro-3-[(pyrrol-2-yl)methylene]indolin-2-one;
5-aminosulfonyl-3-[(pyrrol-2-yl)(ethoxycarbonyl)methylene]indolin-2-one;
5-aminosulfonyl-3-[(pyrrol-2-yl)(carboxy)methylene]indolin-2-one;
5-aminosulfonyl-3-[(pyrrol-2-yl)(aminocarbonyl)methylene]indolin-2-one;
5-cyano-3-[1-(pyrrol-2-yl)ethylidene]indolin-2-one;
5-aminocarbonyl-3-[3-(pyrrol-2-yl)ethylidene]indolin-2-one;
5-aminosulfonyl-3-[1-(pyrrol-2-yl)propylidene]indolin-2-one;
5-aminosulfonyl-3-[(pyrrol-2-yl)(N,N-diethylaminocarbonyl)methylene]indolin-2-one; and
5-aminosulfonyl-3-[(pyrrol-2-yl)(ethylaminocarbonyl)methylene]indolin-2-one.

Of the preferred compounds of formula (I) as set forth above, the most preferred compounds of formula (I) are selected from the group consisting of the following:
5-ureido-3-[(pyrrol-2-yl)methylene]indolin-2-one;
5-ureido-3-[1-(pyrrol-2-yl)ethylidene]indolin-2-one;
5-ureido-3-[1-(pyrrol-2-yl)propylidene]indolin-2-one;
5-ureido-3-[(pyrrol-2-yl)(3-aminophenyl)methylene]indolin-2-one;
5-ureido-3-[1-(4-(piperidin-4-ylcarbonylamino)methylpyrrol-2-yl)ethylidene]indolin-2-one;
5-ureido-3-[(4-(pyridin-3-yl)pyrrol-2-yl)methylene]indolin-2-one;
5-ureido-3-[1-(4-((2-aminoethyl)carbonylamino)methylpyrrol-2-yl)ethylidene]indolin-2-one;
5-ureido-3-[(4-(4-(2-piperidin-1-ylethyl)aminocarbonylphenyl)pyrrol-2-yl)methylene]indolin-2-one;
5-ureido-3-[(4-(4-(2-dimethylaminoethyl)aminocarbonylphenyl)pyrrol-2-yl)methylene]indolin-2-one;
5-ureido-3-[(4-(4-(pyrrolidin-1-yl)butyl)aminocarbonylpyrrol-2-yl)methylene]indolin-2-one;
5-ureido-3-[(4-(3-(2-dimethylaminoethyl)aminocarbonylphenyl)pyrrol-2-yl)methylene]indolin-2-one; and
5-acetamido-3-[1-(4-(2-aminoethylcarbamylmethyl)pyrrol-2-yl)ethylidene]indolin-2-one.

Of the compounds of formula (II) set forth above in the Summary of the Invention, a preferred group of compounds are those compounds wherein:

m is 0 to 4;

A is oxygen;

$R^1$ is hydrogen or alkyl;

each $R^2$ is independently selected from the group consisting of halo, haloalkyl, haloalkenyl, —$R^8$—$OR^7$ and —$R^8$—$N(R^7)C(O)$—$R^8$—$N(R^7)_2$;

$R^3$ is hydrogen or alkyl;

$R^4$ is naphthyl, pyridinyl, furanyl (optionally substituted with one or more substituents selected from the group consisting of alkyl and —$R^8$—$OC(O)R^7$)), indolyl, imidazolyl (optionally substituted with one or more alkyl groups), quinolinyl, or pyrazolyl (optionally substituted with one or more substituents selected from the group consisting of alkyl, halo and phenyl);

each $R^7$ is independently selected from the group consisting of hydrogen, alkyl, —$R^9$—$OR^7$, haloalkyl, aryl, aralkyl, heterocyclyl, heterocyclylalkyl; and each $R^8$ is a bond or a straight or branched alkylene chain; and each $R^9$ is a straight or branched alkylene chain.

Preferred compounds of this group of compounds are those compounds selected from the group consisting of the following:
5-ureido-3-[1-(imidazol-4-yl)ethylidene]indolin-2-one;
5-hydroxy-3-[(imidazol-4-yl)methylene]indolin-2-one;
5-hydroxy-3-[(imidazol-2-yl)methylene]indolin-2-one;
3-[(imidazol-4-yl)methylene]indolin-2-one;
3-[(imidazol-2-yl)methylene]indolin-2-one;
6-fluoro-3-[(pyridin-2-yl)methylene]indolin-2-one;
6-fluoro-3-[(pyridin-4-yl)methylene]indolin-2-one;
5-bromo-3-[(pyridin-4-yl)methylene]indolin-2-one;
3-[(pyridin-3-yl)methylene]indolin-2-one;
6-fluoro-3-[(furan-2-yl)methylene]indolin-2-one;
3-[(5-methylfuran-2-yl)methylene]indolin-2-one;
3-[(5-(acetoxymethyl)furan-2-yl)methylene]indolin-2-one;
3-[(naphth-1-yl)methylene]indolin-2-one;
3-[(naphth-2-yl)methylene]indolin-2-one;
6-fluoro-3-[(indol-3-yl)methylene]indolin-2-one;
3-[(quinolin-4-yl)methylene]indolin-2-one;
3-[(5-methylimidazol-4-yl)methylene]indolin-2-one;
3-[(1,3-dimethyl-5-chloropyrazol-4-yl)methylene]indolin-2-one; and
3-[(3-phenylpyrazol-4-yl)methylene]indolin-2-one.

Preferred compounds of Formula (I) include compounds of the following Formula (Ia) as a single stereoisomer, a mixture of stereoisomers, a solvate or a polymorph; or a pharmaceutically acceptable salt thereof:

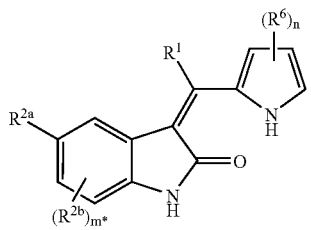

wherein
R$^1$ is hydrogen or alkyl;
R$^{2a}$ is —R$^8$—S(O)$_t$N(R$^7$)$_2$ (where t is 1 or 2), —R$^8$—N(R$^7$)$_2$, —R$^8$—N(R$^7$)S(O)$_t$N(R$^7$)$_2$ (where t is 1 or 2), —R$^8$—N(R$^7$)S(O)$_t$N(R$^7$)C(O)OR$^7$ (where t is 1 or 2), —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)—R$^9$—C(O)N(R$^7$)$_2$, —R$^8$—N(R$^7$)C(O)—R$^8$—N(R$^7$)—R$^8$—C(O)OR$^7$, —R$^8$—N(R$^7$)C(O)—R$^8$—N(R$^7$)—R$^8$—C(O)—R$^8$—N(R$^7$)$_2$, —N(R$^7$)C(=NR$^7$)N(R$^7$)$_2$, or —R$^8$—N=C(R$^7$)$_2$;
R$^{2b}$ is selected from the substituents listed in the definition of R$^2$ set forth in the description of compounds of formula (I);
m* is 0 to 3;
n is 0 to 3;
each R$^6$ is independently selected from the group consisting of halo, alkyl, nitro, —R$^8$—C(O)R$^7$, —R$^8$—N(R$^7$)$_2$, —R$^8$—C(O)OR$^7$, —R$^8$—C(O)N(R$^7$)$_2$, —R$^8$—N(R$^7$)—R$^8$—C(O)OR$^7$, —R$^8$—N(R$^7$)C(O)R$^7$, —R$^8$—C(O)—R$^9$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)C(O)—R$^9$—C(O)OR$^7$, —R$^8$—N(R$^7$)C(O)—R$^8$—N(R$^7$)—R$^8$—C(O)OR$^7$, heterocyclyl (optionally substituted by one or more substituents selected from the group consisting of alkyl, halo, haloalkyl, cyano, nitro, —R$^8$—OR$^7$, —RO—R—C(O)OR, —R$^8$—N(R$^7$)$_2$, —R$^8$—C(O)R$^7$, —R$^8$—C(O)OR$^7$, —R$^8$—C(O)N(R$^7$)$_2$, —R$^8$—N(R$^7$)C(O)OR$^7$, —R$^8$—N(R$^7$)C(O)R$^7$, —R$^8$—S(O)$_p$R$^7$ (where p is 0 to 2), —R$^8$—S(O)$_p$N(R$^7$)$_2$ (where p is 0 to 2), and —R$^8$—N(R$^7$)C(O)—R$^8$—N(R$^7$)$_2$) and aryl (optionally substituted by one or more substituents selected from the group consisting of alkyl, —R$^8$—OR$^7$, —R$^8$—O—R$^9$—C(O)OR$^7$, —R$^8$—C(O)R$^7$, —R$^8$—C(O)OR$^7$, —R$^8$—C(O)N(R$^7$)$_2$, —R$^8$—N(R$^7$)C(O)R$^7$, —R$^8$—N(R$^7$)C(O)OR$^7$, —R$^8$—N(R$^7$)$_2$, —R$^8$—N(R$^7$)C(O)—R$^8$—N(R$^7$)—R$^8$—C(O)OR$^7$, and —R$^8$—S(O)$_t$R$^7$ (where t is 0 to 2));
each R$^7$ is independently hydrogen, optionally substituted alkyl, haloalkyl, optionally substituted aryl, optionally substituted aralkyl, optionally substituted heterocyclyl, or optionally substituted heterocyclylalkyl;
each R$^8$ is a bond or a straight or branched alkylene chain; and
each R$^9$ is a straight or branched alkylene chain.

Preferred compounds within the scope of formula (Ia) include compounds where:
R$^1$ is hydrogen;
R$^{2a}$ is —R$^8$—N(R$^7$)$_2$, —R$^8$—N(R$^7$)S(O)$_t$N(R$^7$)$_2$ (where t is 1 or 2), —R$^8$—N(R$^7$)S(O)$_t$N(R$^7$)C(O)OR$^7$ (where t is 1 or 2), —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)—R$^9$—C(O)N(R$^7$)$_2$, —R$^8$—N(R$^7$)C(O)—R$^8$—N(R$^7$)—R$^8$—C(O)OR$^7$, —R$^8$—N(R$^7$)C(O)— R$^8$—N(R$^7$)—R$^8$—C(O)—R$^8$—N(R$^7$)$_2$, —N(R$^7$)C(=NR$^7$)N(R$^7$)$_2$, or —R$^8$—N=C(R$^7$)$_2$; and
m* is 0.

More preferred compounds within the scope of formula (Ia) include compounds where
R$^1$ is hydrogen;
R$^{2a}$ is —R$^8$—N(R$^7$)S(O)$_t$N(R$^7$)$_2$ (where t is 1 or 2), —R$^8$—N(R$^7$)S(O)$_t$N(R$^7$)C(O)OR$^7$ (where t is 1 or 2), —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)—R$^9$—C(O)N(R$^7$)$_2$, —R$^8$—N(R$^7$)C(O)—R$^8$—N(R$^7$)—R$^8$—C(O)OR$^7$, or —R$^8$—N(R$^7$)C(O)—R$^8$—N(R$^7$)—R$^8$—C(O)—R$^8$—N(R$^7$)$_2$; and
m* is 0.

Preparation of the Compounds of Formula (I) and (II)

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl (dimethylethoxycarbonyl), benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of the invention, as described above in the Summary of the Invention, may not possess pharmacological activity as such, they may be administered to a mammal with disease-state alleviated by the inhibition of PDK-1 activity and thereafter metabolized in the body to form compounds of the invention which are pharmacologically active. Such derivatives may therefore be described as "prodrugs". All prodrugs of compounds of the invention are included within the scope of the invention.

The following Reaction Schemes illustrate methods to make compounds of formula (I) where A is O. It is understood that one of ordinary skill in the art would be able to make other compounds of formula (I) and the compounds of formula (II) by similar methods or by methods known to one skilled in the art. In general, starting components may be obtained from sources such as Aldrich, or synthesized according to sources known to those of ordinary skill in the art (see, e.g., Smith and March, *March's Advanced Organic Chemistry: Reactions, Mechanisms, and Structure*, 5th edition (Wiley Interscience, New York)). Moreover, the R groups are selected from components as indicated in the specification heretofore, and may be attached to starting components, intermediate components, and/or final products according to schemes known to those of ordinary skill in the art.

In the following Reaction Schemes, unless otherwise noted, the various R groups are as defined above in the Summary of the Invention.

A. Preparation of Compounds of Formula (D)

Compounds of formula (D) are intermediates in the preparation of the compounds of formula (I). They are prepared as described below in Reaction Scheme 1 wherein $POCl_3$ is phosphorus oxychloride; DMF is dimethylformamide; $R^{5a}$ is hydrogen or a nitrogen-protecting group, such as phenylsulfonyl; $R^8$ is as defined above in the Summary of the Invention, $R^{7a}$ is alkyl or aralkyl, and X is halo:

REACTION SCHEME 1

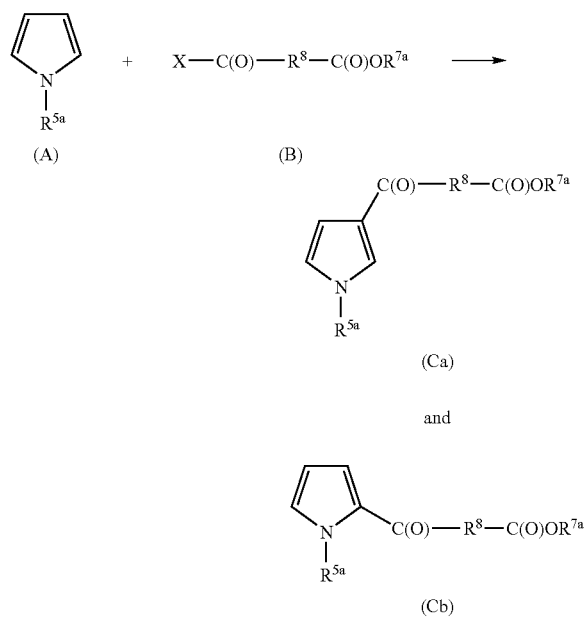

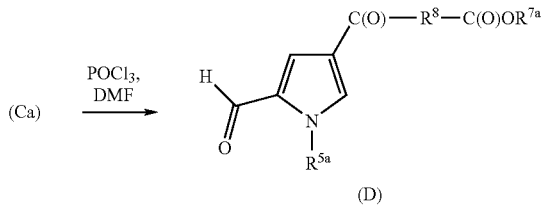

Compounds of formula (A) and formula (B) are commercially available or can be prepared according to methods known to one skilled in the art. In general, compounds of formula (Ca) and formula (Cb) are prepared by the method described in Kato, M. et. al., Chem. Pharm. Bull. (1997), Vol. 45, No. 11, p. 1767, in particular, by first treating a compound of formula (B) under standard Friedel-Crafts acylation conditions (for example, in the presence of a catalytic amount of aluminum chloride in an aprotic solvent, such as dichloromethane) with a protected or unprotected pyrrole compound of formula (A). The resulting reaction mixture is allowed to stir at ambient temperature for about 8 to about 16 hours, preferably for about 16 hours. The solvent is extracted and concentrated to form a mixture of isomers of formula (Ca) and (Cb), which were isolated by standard isolation techniques, such as chromatography.

The isomer of formula (Ca) is then treated with standard Vilsmeier-Haack reaction conditions (for example, in the presence of a suitable disubstituted formamide and phosphorus oxychloride in an aprotic solvent, such as dichloromethane). The resulting reaction mixture is heated to between about 50° C. and about 60° C., preferably to about 55° C. and stirred for a period of time of between about 3 hours and 4 hours, preferably for about 3.5 hours. The reaction is quenched by the addition of strong base, such as sodium hydroxide, and the resulting reaction mixture is allowed to stir at ambient temperature for a period of time of between about 8 hours and about 16 hours. The compound of formula (D) is isolated from the reaction mixture by standard isolation techniques, such as organic solvent extraction, removal of solvent by concentration and chromatography.

Compounds of formula (D) can be further hydrolized under standard hydrolysis conditions to produce compounds where $R^{7a}$ is hydrogen.

B. Preparation of Compounds of Formula (H)

Compounds of formula (H) are intermediates in the preparation of the compounds of formula (I). They are prepared as described below in Reaction Scheme 2 wherein $PG^1$ is t-butoxycarbonyl (dimethylethoxycarbonyl); $R^1$ is as described above in the Summary of the Invention; and X is halo:

REACTION SCHEME 2

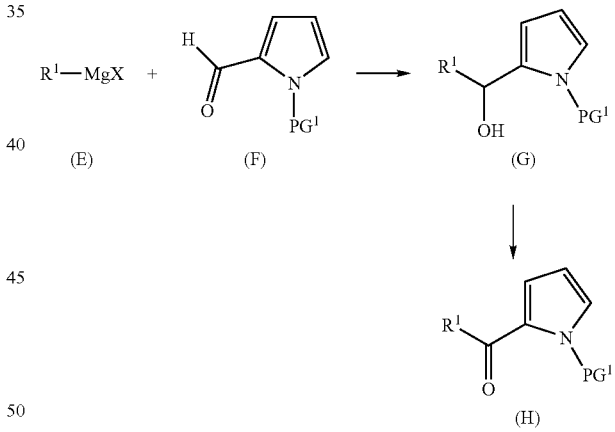

Compounds of formula (E) and formula (F) are commercially available or can be prepared according to methods known to one skilled in the art.

In general, compounds of formula (H) are prepared by first treating a compound of formula (F) in a polar solvent, such as tetrahydrofuran, with the Grignard reagent of formula (E) at initial temperatures of between about −30° C. and about 0° C., preferably at about −30° C. The reaction mixture is allowed to gradually warm to ambient temperature over a period of time of between about 1 hour and 2 hours, preferably about 1.5 hours. The reaction mixture is then poured into ice water and stirred for a period of time of between about 15 minutes and about 1 hour, preferably for about 30 minutes. The compound of formula (G) is isolated from the reaction mixture by standard isolation techniques, such as organic solvent extraction, removal of the solvent by concentration and chromatography. If desired at this point, the compound of formula (G) may be further treated under standard conditions to protect any functional $R^1$ groups.

Compounds of formula (G) in an aprotic solvent, such as dichloromethane, are then oxidized under standard oxidation conditions to yield the corresponding ketones of formula (H), which are then deprotected by standard deprotection techniques.

Alternatively, compounds of formula (F) can be treated with an $R^1$-organolithium group to produce the corresponding compounds of formula (G).

C. Preparation of Compounds of Formula (L) and Formula (La)

Compounds of formula (L) and formula (La) are intermediates in the preparation of the compounds of formula (I). They are prepared as described below in Reaction Scheme 3 wherein $R^1$ is as defined above in the Summary of the Invention, $PG^2$ is a nitrogen-protecting group, and $R^{6a}$ is —$CH_2NH_2$:

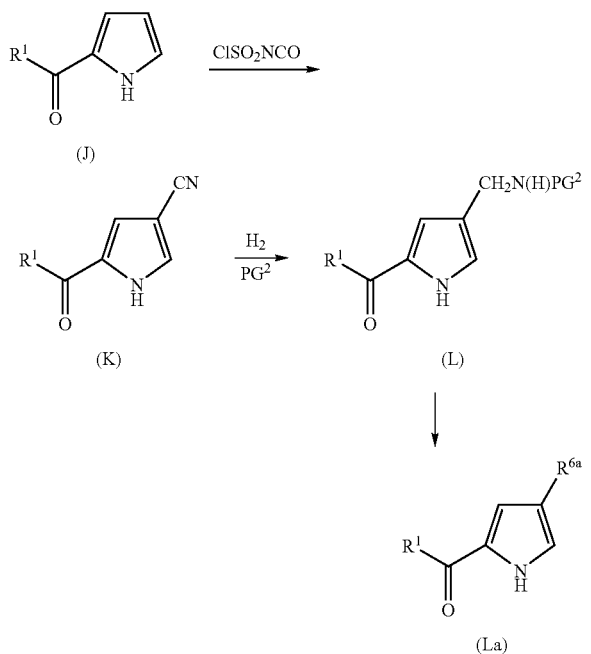

Compounds of formula (J) are commercially available or may be prepared by methods known to one of ordinary skill in the art.

In general, compound of formula (K) is prepared according to the method described in Loader, C. et al., *Can J. Chem.* (1981), Vol. 59, p. 2673. In particular, a solution of chlorosulfonylisocyanate in an aprotic solvent, such as acetonitrile, is added to a solution of a compound of formula (J) in an aprotic solvent, such as acetonitrile. The resulting reaction mixture is stirred at ambient temperatures for between about 2 hours and 3 hours, preferably for about 2.5 hours. The reaction mixture is then cooled to a temperature of between about −5° C. and about 5° C., preferably to about 0° C. and dimethylformamide is added to the mixture. The resulting reaction mixture is heated to a temperature of between about 45° C. and 55° C., preferably to about 50° C. for a period of time of between about 5 minutes and 20 minutes, preferably for about 10 minutes, and then poured onto ice. The compound of formula (K) is then isolated from the reaction mixture by standard isolation techniques, such as dissolving the product in an organic solvent, such as ethyl acetate, filtering the resulting solvent with activated charcoal, evaporating off the organic solvent, and recrystallizing the resulting product.

The compound of formula (K) is then reduced under standard reducing conditions, such as treatment of the compound in a protic solvent, such as methanol, by catalytic hydrogenation in the presence of a nitrogen-protecting group precursor, such as di-t-butyl dicarbonate, to afford a compound of formula (L), which is isolated from the reaction mixture by standard isolation techniques, such as filtration, concentration and purification by silica gel chromatography.

Compounds of formula (L) can then be deprotected by standard nitrogen-deprotecting techniques to form compounds of formula (La). Compounds of formula (La) can then be treated with the appropriate acylating or alkylating agent to form compounds of formula (La) wherein $R^{6a}$ is —$R^{8a}$—$N(R^7)_2$, —$R^{8a}$—$N(R^7)C(O)R^7$, —$R^{8a}$—$N(R^7)$—$R^8$—$C(O)OR^7$, —$R^{8a}$—$N(R^7)C(O)$—$R^9$—$C(O)OR^7$, —$R^{8a}$—$N(R^7)S(O)_t$—$R^{8a}$—$N(R^7)_2$ (where t is 1 or 2), and —$R^{8a}$—$N(R^7)S(O)_t$—$R^7$ (where t is 1 or 2) where $R^{8a}$ is —$CH_2$— and each $R^7$, $R^8$ and $R^9$ are as described above in the Summary of the Invention.

D. Preparation of Compounds of Formula (P)

Compounds of formula (P) are intermediates in the preparation of the compounds of formula (I). They are prepared as described below in Reaction Scheme 4 wherein $PG^3$ is a nitrogen-protecting group, p is 1 to 5 and $R^6$ is optionally substituted aryl or optionally substituted heterocyclyl:

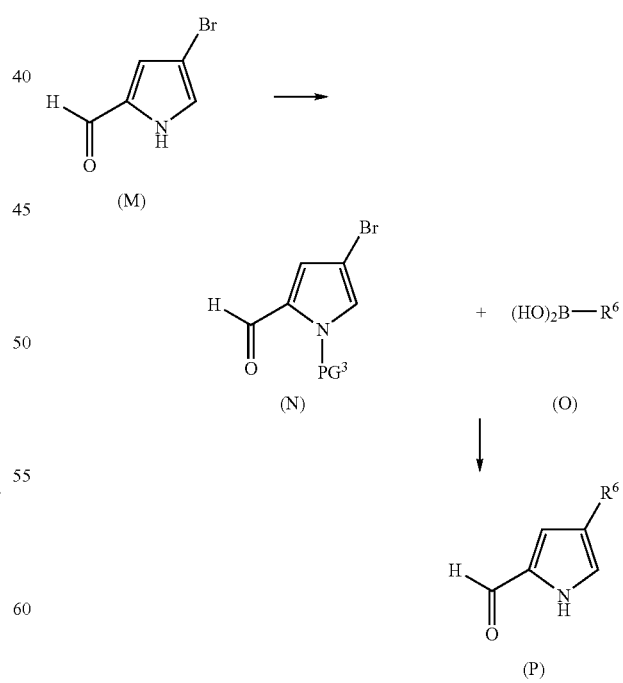

Compounds of formula (M) are prepared by the method disclosed in Sonnet, P. E., *J. Org. Chem.*, (1971), Fol. 36, p. 1005, or by methods known to one skilled in the art.

Compounds of formula (O) are commercialy available or may be prepared according to methods known to one skilled in the art.

In general, compounds of formula (P) are prepared by first preparing a compound of formula (M) by the method disclosed in Sonnet, P. E., *J. Org. Chem.*, (1971), Fol. 36, p. 1005. The compound of formula (M) is then dissolved in polar aprotic solvent, such as tetrahydrofuran, and cooled to a temperature of between about −5° C. and about 5° C., preferably at about 0° C. The reaction mixture is then treated with a strong base, such as lithium diisopropylamide in an aprotic polar solvent, such as tetrahydrofuran, and the resulting mixture is stirred at temperatures of between about −5° C. and about 5° C., preferably at about 0° C., for a period of time of between about 15 minutes and about 2 hours, preferably for about 15 minutes. A nitrogen-protecting group precursor, such as tosyl chloride, is then added to the reaction mixture. The resulting reaction mixture is allowed to warm to ambient temperature. The compound of formula (N) is then isolated from the reaction mixture by standard isolation techniques, such as diluting the reaction mixture with an organic solvent, washing the solution with water and brine, concentrating the solvent and silica gel chromatography.

Compounds of formula (N) are then treated under standard Suzuki coupling condtions (Miyaura, N. and Suzuki, A., *Chem. Rev.* (1995), Vol. 95, p. 2457) to form compounds of formula (P). In particular, the compound of formula (N) is dissolved in a protic solvent, such as ethanol, and the resulting solution is warmed to below reflux temperature. An excess molar amount of a compound of formula (O) is then added to the solution and the resulting reaction mixture is diluted with an aprotic organic solvent, such as toluene, and the resulting mixture is stirred until the reagents are completely dissolved. A palladium catalyst, such as $Pd(PPh_3)_4$, is then added to the reaction mixture in the presence of a base, such as sodium bicarbonate, and the resulting reaction mixture is stirred at reflux temperatures overnight. The compound of formula (P) is then isolated from the reaction mixture by standard isolation techniques, such as organic solvent extraction, concentration and chromatography.

E. Preparation of Compounds of Formula (T)

Compounds of formula (T) are intermediates in the preparation of the compounds of formula (I). They are prepared as described below in Reaction Scheme 5 wherein $R^7$ is haloalkyl and $R^8$ is a direct bond:

REACTION SCHEME 5

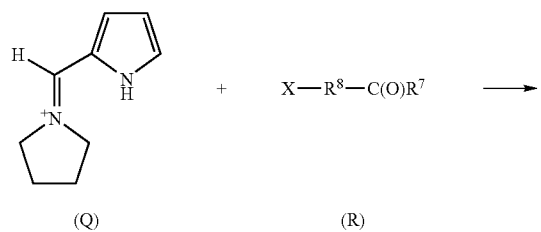

(Q)  (R)

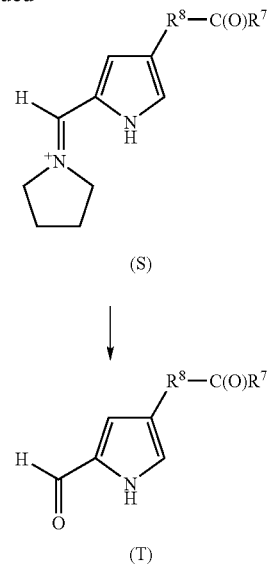

(S)

(T)

Compounds of formula (R) are commercially available or may be prepared according to methods known to one skilled in the art. Compounds of formula (Q) may be prepared by the method disclosed in Sonnet, P. E., *J. Org. Chem.*, (1971), Fol. 36, p. 1005, or by methods known to one skilled in the art.

In general, compounds of formula (T) are prepared by first treating a compound of formula (Q) in an aprotic solvent, such as dichloroethane, with a Lewis acid, such as aluminum chloride. The reaction mixture is cooled to a temperature of between about −5° C. and about 5° C., preferably to about 0° C. and then treated with an equimolar amount of a compound of formula (R). The reaction mixture is stirred at a temperature of between about −5° C. and about 5° C., preferably to about 0° C., for a period of time between about 8 hours and about 16 hours, preferably for about 16 hours. The reaction is then quenched by pouring the reaction mixture over crushed ice. The resulting compound of formula (S) is then hydrolyzed under standard base hydrolysis conditions, such as treatment with sodim bicarbonate. The compound of formula (T) is then isolated from the reaction mixture by standard isolation techniques, such as organic solvent extraction and concentration.

Compounds of formula (T) can further be treated with an appropriately substituted N-heterocyclyl to form compounds of formula (T) where $R^7$ is heterocyclylalkyl, which can then be used in subsequent reaction schemes described herein to prepare compounds of the invention. Alternatively, compounds of formula (T) can further be treated with an appropriately substituted amine of the formula $HN(R^7)_2$ to form compounds of the following formula (Ta) where $R^9$ and $R^7$ are as described above in the Summary of the invention, which can then be used in subsequent reaction schemes described herein to prepare compounds of the invention:

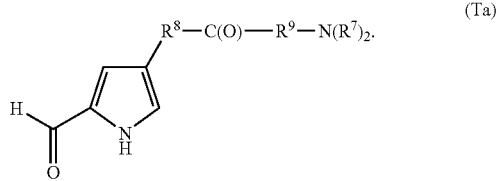

F. Preparation of Compounds of Formula (Ia)

Compounds of formula (Ia) are compounds of formula (I) and are prepared as described below in Reaction Scheme 6 wherein n, m, $R^1$, $R^2$, $R^3$ and $R^6$ are as described above in the Summary of the Invention:

REACTION SCHEME 6

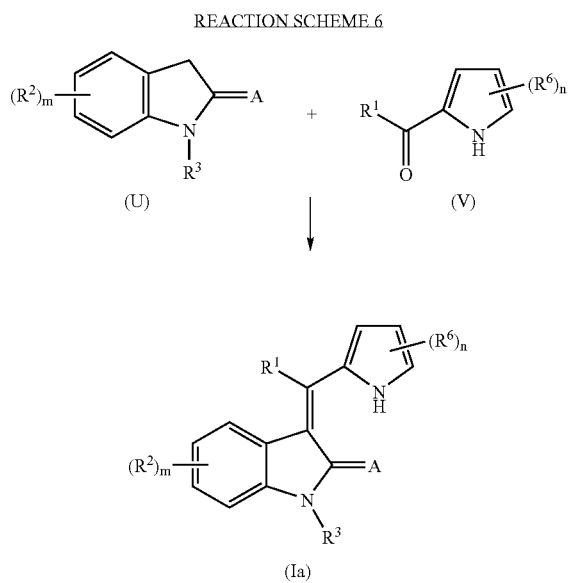

Compounds of formula (U) and formula (V) are commercially available or may be prepared according to methods known to one skilled in the art or by methods disclosed herein. Unprotected amine groups on the compounds of formula (U) must be protected prior to the reaction.

In general, compounds of formula (Ia) wherein $R^1$ is hydrogen, —C(O)OR$^7$ or —C(O)N(R$^7$)$_2$ are prepared by treating a compound of formula (U) with a compound of formula (V) n the presence of an alcohol, preferably ethanol or methanol, and a catalytic amount of a base, prefereably piperidine, at temperatures of between about 75° C. and 85° C., preferably at about 85° C. for a period of time of between about 2 hours and 4 hours, preferably for about 3 hours. The compound of formula (Ia) is then isolated from the reaction mixture by standard isolation techniques, such as chromatography.

Alternatively, compounds of formula (Ia) where $R^1$ is alkyl, optionally substituted aryl, optionally substituted aralkyl, optionally substituted heterocyclyl or optionally substituted heerocyclylalkyl as described above in the Summary of the Invention are prepared by heating a mixture of a compound of formula (U) and a compound of formula (V) in the presence of a catalytic amount of a base, preferably piperidine, to a temperature of between about 120° C. and about 140° C., preferably to about 130° C. for a period of time of between about 8 hours and about 16 hours, preferably for about 16 hours. Upon cooling, the compound of formula (Ia) is isolated from the reaction mixture by standard isolation techniques, such as silica gel chromatography.

Alternatively, compounds of formula (Ia) where R₁ is —R$^8$—C(O)OR$^7$ or —R$^8$—C(O)N(R$^7$)$_2$ are prepared by first treating a compound of formula (U) with a compound of formula (V) where $R^1$ is —R$^8$—C(O)C(O)OR$^7$ or —R$_8$—C(O)C(O)N(R$^7$)$_2$ in a polar solvent, such as ethanol, in the presence of a base, such as triethylamine. The resulting reaction mixture is refluxed for a period of time of between about 12 hours and about 55 hours, preferably for about 55 hours. The compounds of formula (Ia) where $R^1$ is —R$^8$—C(O)OR$^7$ are then isolated from the reaction mixture by standard isolation techniques, such as concentration and reverse phase HPLC.

Alternatively, compounds of formula (Ia) $R^1$ is —R$_8$—C(O)N(R$^7$)$_2$ are prepared by first treating a compound of formula (U) with a compound of formula (V) where $R^1$ is —R$_8$—C(O)C(O)N(R$^7$)$_2$ in the presence of a catalytic amount of a base, preferably piperidine. The resulting reaction mixture is irradiated in a microwave oven at a temperature of between about 150° C. and about 160° C., preferably of about 160° C., for a period of time of between about 1 minute and about 5 minutes, preferably of about 5 minutes. The reaction mixture is then dissolved in an aprotic solvent, preferably dichloromethane, and the compounds of formula (Ia) where $R^1$ is —R$^8$—C(O)N(R$^7$)$_2$ are then isolated from the reaction mixture by standard isolation techniques, such as acid/base wash, concentration and chromatography.

Compounds of formula (Ia) wherein the $R^2$ group is —R$^8$—OR$^7$ where $R^7$ is alkyl, hydroxyalkyl, haloalkyl, aralkyl or heterocyclylalkyl can be converted into the corresponding compounds where $R^7$ is hydrogen under standard Lewis acid cleavage conditions, such as treatment of the compound with an excess molar amount of boron tribromide in an aprotic solvent, such as dichloromethane.

Compounds of formula (Ia) wherein the $R^2$ group contains a terminal amino group can be reacted, for example, with acylating or alkylating agents, isocyanates or thioisocyanates to afford compounds of formula (Ia) wherein $R^2$ is —R$^8$—N(R$^7$)$_2$, —R$^8$—N(R$^7$)S(O)$_t$R$^7$ (where t is 1 or 2), —R$^8$—N(R$^7$)S(O)$_t$N(R$^7$)$_2$ (where t is 1 or 2), —R$^8$—N(R$^\ $)S(O)$_t$N(R$^7$)C(O)OR$^7$ (where t is 1 or 2), —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$—R$^8$—N(R$^7$)—R$^9$—C(O)N(R$^7$)$_2$, —R$^8$—N(R$^7$)C(O)—R$^8$—N(R$^7$)—R$^8$—C(O)OR$^7$, —R$_8$—N(R$^7$)C(O)—R$^8$—N(R$^7$)—R$^8$—C(O)—R$^8$—N(R$^7$)$_2$ or —N(R$^7$)C(=NR$^7$)N(R$^7$)$_2$.

Compounds of formula (Ia) where $R^2$ is cyano can be treated in a manner similar to that described in U.S. Pat. No. 5,691,364 to form compounds of the invention wherein $R^2$ is —C(=NR$^7$)—N(R$^7$)$_2$.

G. Preparation of Compounds of Formulae (Ib), (Ic), (Id), (Ie)

Compounds of formulae (Ib), (Ic), (Id), and (Ie) are compounds of formula (I) and are prepared as described below in Reaction Scheme 7 wherein A is oxygen, $R^{7a}$ is alkyl, and n, $R^1$ and $R^6$ are as described above in the Summary of the Invention:

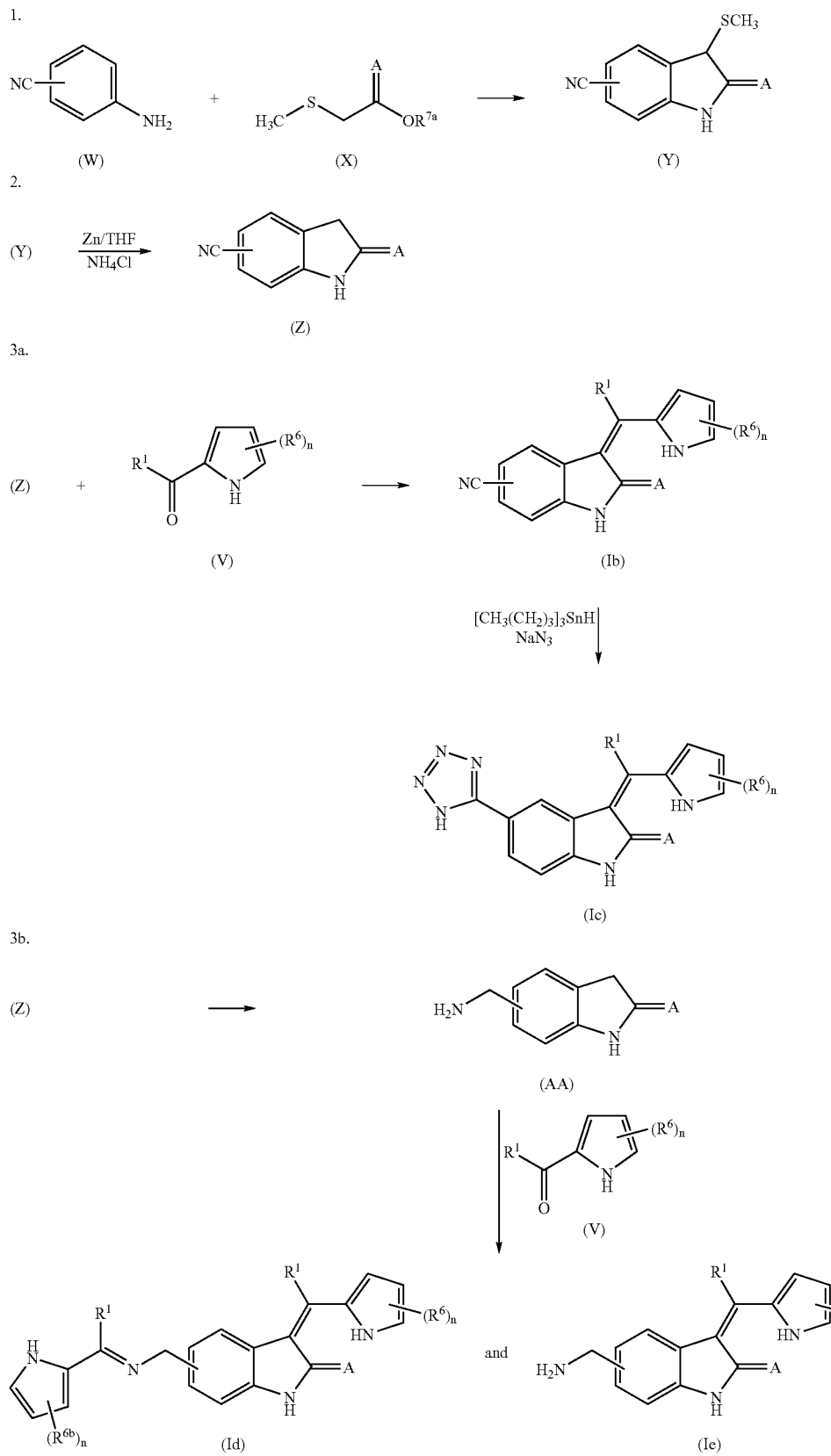

Compounds of formula (X) and formula (W) are commercially available or may be prepared according to methods known to one skilled in the art. Compounds of formula (V) are commercially available or may be prepared according to methods known to one skilled in the art or by methods disclosed herein.

In general, compounds of formulae (Ib), (Ic), (Id) and (Ie) are prepared by first preparing the compounds of formula (Y) and formula (Z) by the method described in PCT Published Patent Application, WO 99/10325.

To a suspension of a compound of formula (Z) in a protic solvent, such as ethanol, is added a compound of formula (V) in the presence of a base, such as piperidine. The reaction mixture is refluxed for a time period of between about 2 hour and about 3 hours, preferably for about 2 hours. The compound of formula (Ib) is then isolated from the reaction mixture by standard isolation techniques, such as precipitation, filtration and organic solvent extraction.

Under standard radical cyclization conditions, the compound of formula (Ib) in an organic solvent, such as toluene, is then treated with tributyltin hydride (0.68 g, 2.1 mmol) and $NaN_3$ (0.39 g, 2.52 mmol). The reaction mixture is refluxed overnight for a time period of between about 8 hours and about 16 hours, preferably for about 16 hours. The compound of formula (Ic) is then isolated from the reaction mixture by standard isolation techniques, such as concentration, filtration and evaporation of solvents.

Alternatively, the compound of formula (Z) may be hydrogenated under standard catalytic hydrogenation conditions to yield a compound of formula (AA), which is isolated from the reaction mixture by standard isolation techniques, such as filtration and concentration of solvents.

A compound of formula (AA) is then treated with an excess molar amount of a compound of formula (V) in the presence of a catalytic base, such as piperidine. The resulting solution is mixed in a microwave reaction vessel and heated to a temperature of between about 155° C. and 165° C., preferably of about 160° C. for a period of time of between about 5 minutes and about 10 minutes, preferably for about 8 minutes, in a microwave reactor. The compound of formula (Id) is isolated from the reaction mixture by re-dissolving the product in a polar aprotic solvent, such as dimethylsulfoxide, and purified by standard techniques, such as reverse phase HPLC.

Alternatively, a compound of formula (AA) in a protic solvent, such as ethanol, is treated with a base, such as diisopropylethylamine. After a period of time of between about 10 minutes and 30 minutes, preferably after 20 minutes, a compound of formula (V) and a catalytic base, such as pyrrolidine, are added to the solution. The resulting reaction mixture is stirred at a temperature of between about 50° C. and 70° C., preferably at about 60° C., for a period of time of between about 2 hours and about 4 hours, preferably for about 3 hours. The compound of formula (Ie) is then isolated from the reaction mixture by standard isolation techniques, such as concentration of the solvent and purification by reverse phase HPLC.

The compound of formula (Ie) can be further reacted, for example, with acylating or alkylating agents, isocyanates or thioisocyanates to afford compounds of the invention wherein $R^2$ is $-CH_2-N(R^7)_2$, $-CH_2-N(R^7)S(O)_tR^7$ (where t is 1 or 2), $-CH_2-N(R^7)S(O)_tN(R^7)_2$ (where t is 1 or 2), $-CH_2-N(R^7)S(O)_tN(R^7)C(O)OR^7$ (where t is 1 or 2), $-CH_2-N(R^7)C(O)R^7$, $-CH_2-N(R^7)-R^8-C(O)OR^7$, $-CH_2-N(R^7)C(O)N(R^7)_2$, $-CH_2-N(R^7)C(O)-R^9-N(R^7)_2$, $-CH_2-N(R^7)-R^9-C(O)N(R^7)_2$, $-CH_2-N(R^7)C(O)-R^8-N(R^7)-R^8-C(O)OR^7$, $-CH_2-N(R^7)C(O)-R^8-N(R^7)-R^8-C(O)-R^8-N(R^7)_2$ or $-N(R^7)C(=NR^7)N(R^7)_2$.

H. Preparation of Compounds of Formula (If) and Formula (Ig)

Compounds of formula (If) and formula (Ig) are compounds of formula (I) and are prepared as described below in Reaction Scheme 8 wherein n, $R^1$ and $R^6$ are as described above in the Summary of the Invention, and $PG^4$ is isocyanate protecting group, such as trimethylsilyl:

REACTION SCHEME 8

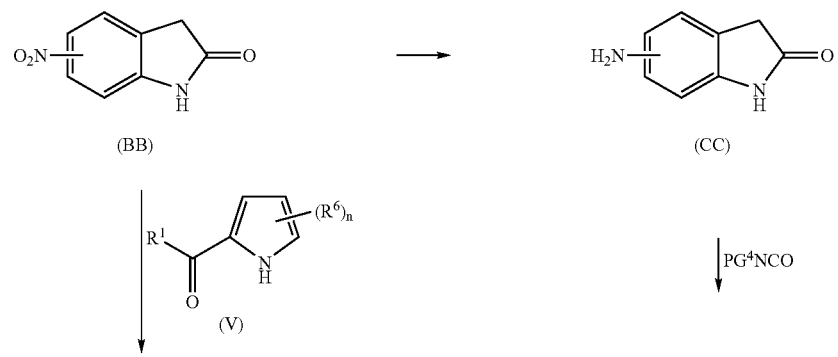

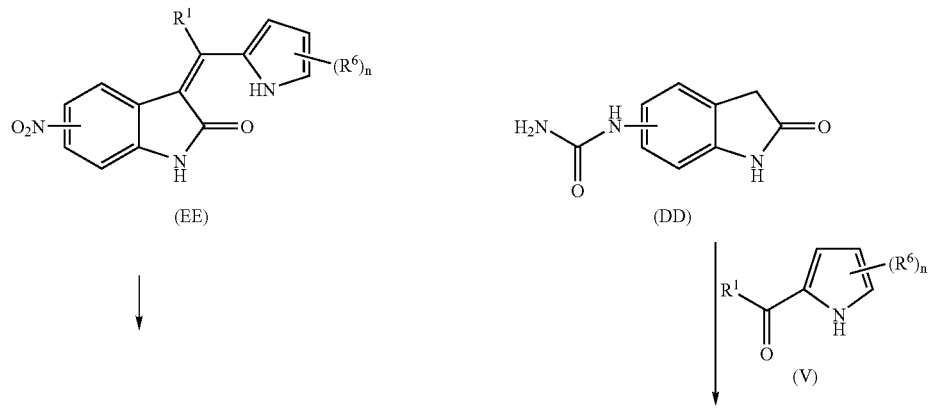

(EE) (DD)

(V)

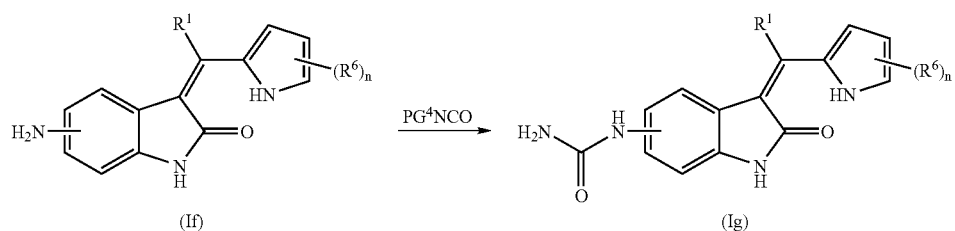

(If) PG⁴NCO (Ig)

Compounds of formula (BB) are commercially available or may be prepared according to methods known to one skilled in the art. Compounds of formula (V) are commerically available or may be prepared according to methods known to one skilled in the art or by methods disclosed herein.

In general, compounds of formula (Ig) are prepared by first reducing a compound of formula (BB) under standard catalytic hydrogenation conditions to form a compound of formula (CC).

The compound of formula (CC) in an aprotic polar solvent, such as a mixture of tetrahydrofuran and dimethylformamide, is then treated with an excess molar amount of a protected isocyanate. The resulting reaction mixture is then stirred at ambient temperature for a period of time between about 8 hours and about 20 hours, preferably for about 18 hours. A compound of formula (DD) is isolated from the reaction mixture by standard isolation techniques, such as filtration, organic solvent wash and evaporation of solvents.

The compound of formula (DD) in a protic solvent, preferably ethanol, is then treated with a compound of formula (V) in the presence of a catalytic amount of piperidine. The resulting reaction mixture is refluxed for a period of time of between about 8 hours and 20 hours, preferably for about 18 hours. After cooling, a compound of formula (Ig) is isolated from the reaction mixture by standard isolation techniques, such as filtration and organic solvent wash.

In general, compounds of formula (If) are prepared by first treating a compound of formula (BB) with an excess molar amount of a compound of formula (V) in the presence of a catalytic amount of piperidine. The resulting reaction mixture is heated to a temperature of between about 80° C. and 90° C., preferably to about 85° C., in a sealed tube reactor for a period of time of between about 2 hours and about 4 hours, preferably for about 3 hours. After cooling, the compound of formula (If) is isolated from the reaction mixture by standard isolation techniques, such as trituration, filtration, and organic solvent wash.

The compound of formula (If) can then be treated with a protected isocyanate as described above for compounds of formula (CC) to form corresponding compounds of formula (Ig).

I. Preparation of Compounds of Formulae (Ih), (Ii), (Ij) and (Ik)

Compounds of formulae (Ih), (Ii), (Ij) and (Ik) are compounds of formula (I) and are prepared as described below in Reaction Scheme 9 wherein X is halo, n, $R^1$ and $R^6$ are as described above in the Summary of the Invention and $R^{7a}$ is alkyl:

REACTION SCHEME 9

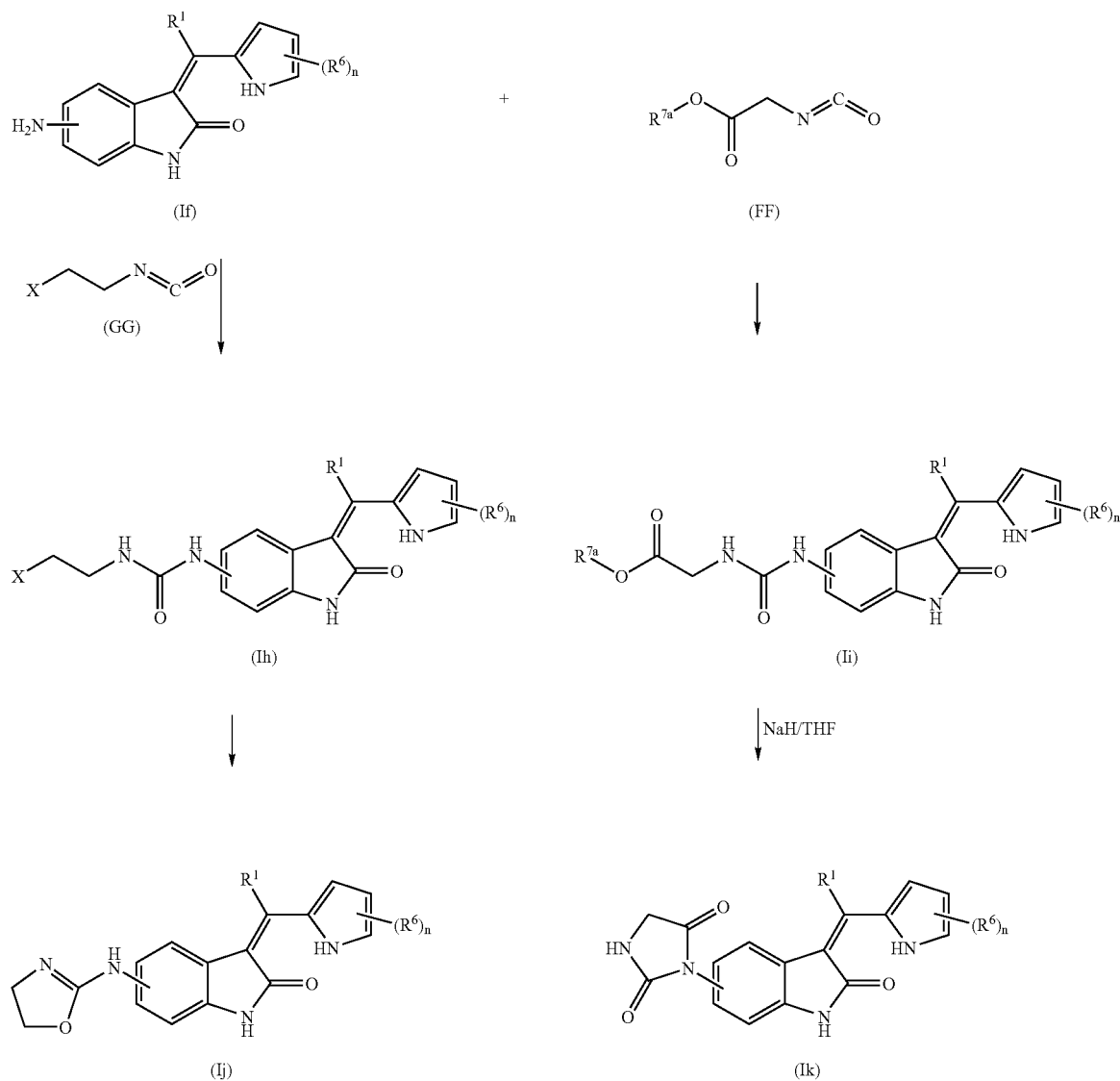

Compounds of formula (FF) and formula (GG) are commercially available or may be prepared according to methods known to one skilled in the art.

In general, compounds of formula (Ih) and (Ij) are prepared by first treating a compound of formula (If) in a polar aprotic solvent, such as dry tetrahydrofuran, with a compound of formula (GG) at ambient temperature. The resulting reaction mixture is stirred at a temperature of between about 40° C. and about 50° C., preferably at about 45° C., for a period of time of between about 1 hour and about 3 hours, preferably for about 2 hours. The reaction mixture is cooled to ambient temperature and the compound of formula (Ih) is isolated from the reaction mixture by standard isolation techniques, such as concentration of the solvents and silica gel chromatography.

The compound of formula (Ih) in a polar aprotic solvent, such as dimethylformamide, is then treated with base, such as triethyamine, and the reaction mixture is allowed to stir at ambient temperature for a period of time of between about 8 hours and about 20 hours, preferably for about 16 hours. The compound of formula (Ij) is then isolated from the reaction mixture by standard isolation techniques, such as filtration and purification by reverse phase HPLC.

In general, compounds of formula (Ii) and (Ik) are prepared by first treating a compound of formula (If) in a polar aprotic solvent, such as tetrahydrofuran, with a compound of formula (FF) at ambient temperature. The resulting reaction mixture is stirred for a period of time of between about 8 hours and about 20 hours, preferably for about 16 hours. The compound of formula (Ik) is isolated from the reaction mixture by standard isolation techniques, such as concentration and silica gel chromatography.

J. Preparation of Compounds of Formula (IIa)

Compounds of formula (IIa) are compounds of formula (II) wherein $R^4$ is optionally substituted imidazol-4-yl and are prepared as described below in Reaction Scheme 10 where m, A, $R^1$, $R^2$, and $R^3$ are as described above in the Summary of the Invention:

REACTION SCHEME 10

1.

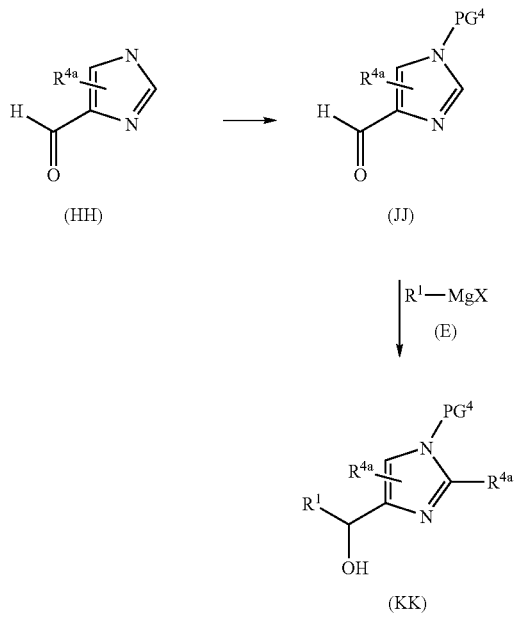

2.

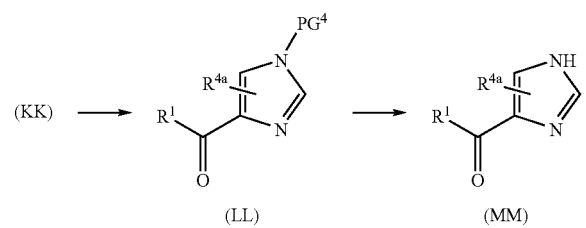

3.

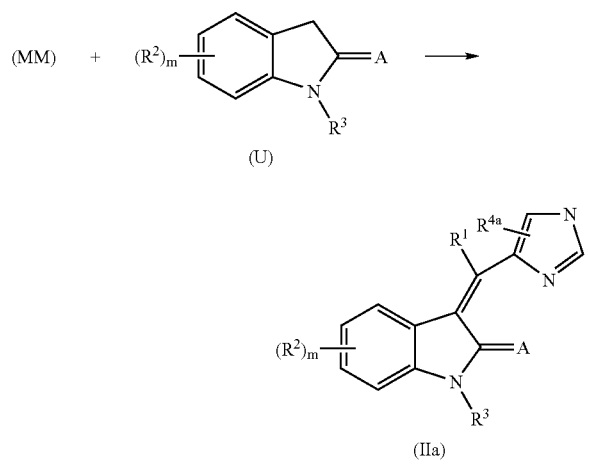

Compounds of formula (HH) and formula (U) are commercially available or may be prepared according to methods known to one skilled in the art.

In general, compounds of formula (IIa) are prepared by first treating a compound of formula (HH) in a polar aprotic solvent, such as tetrahydrofuran, with a nitrogen-protecting group precursor, di-t-butyl dicarbonate, in the presence of a catalytic amount of base, such as dimethylaminopyridine, at ambient temperature. The compound of formula (JJ) is then isolated from the reaction mixture by standard isolation techniques, such as organic extraction and concentration of solvents.

The compound of formula (JJ) in a polar aprotic solvent, such as tetrahydrofuran, is then treated with an appropriate Grignard reagent of formula (EE) at ambient temperature for a period of time of between about 8 hours and about 20 hours, preferably for about 16 hours. The compund of formula (KK) is then isolated from the reaction mixture by standard isolation techniques, such as extraction with ethyl acetate, and concentration.

The compound of formula (KK) is dissolved in an aprotic solvent, such as methylene chloride and then treated with an oxidizing agent, such as manganese oxide. The resulting reaction mixture is stirred at ambient temperature for a period of time of between about 8 hours and about 20 hours, preferably for about 16 hours. The compound of formula (LL) is then isolated from the reaction mixture by standard isolation techniques, such as filtration, concentration and purification by silica gel chromatography.

The compound of formula (LL) is then deprotected using standard nitrogen-deprotecting techniques to form a compound of formula (MM).

The compound of formula (MM) is then treated with a compound of formula (U) as described herein, i.e., the presence of a catalytic amount of piperidine at temperatures of between about 75° C. and 140° C., preferably at about 135° C., to form a compound of formula (IIa), which is isolated from the reaction mixture by standard isolation techniques.

Compounds of formula (IIa) wherein $R^2$ is nitro can be further treated under standard reduction conditions to form the corresponding amino-substituted compounds of formula (IIa), which can be further treated under standard conditions to form the corresponding ureido-substituted compounds of formula (IIa), such as treatment of the amino-substituted compound with an excess molar amount of the appropriately substituted isocyanate.

All compounds of the invention prepared above which exist in free base or acid form may be converted to their pharmaceutically acceptable salts by treatment with the appropriate inorganic or organic base or acid. Salts of the compounds prepared above may be converted to their free base or acid form by standard techniques.

The following specific examples are provided as a guide to assist in the practice of the invention, and are not intended as a limitation on the scope of the invention.

Preparation 1

Compounds of Formula (C) and Formula (D)

A. A mixture of $AlCl_3$ (24.02 g) and dichloromethane (400 mL) was treated with (carbomethoxy)propionyl chloride (27.05 g). A solution of pyrrole (10.01 g) in dichloromethane (150 mL) was then added dropwise. After stirring overnight, the reaction mixture was poured over ice and water (500 mL). The resulting mixture was then extracted with dichloromethane (500 mL). The combined organic layers were washed with brine (500 mL), dried (MgSO$_4$) and concentrated to afford γ-oxo-1-H-pyrrole-3-butanoic acid ethyl ester (5.14 g).

B. A solution of DMF (1.2 mL) in 1,2-dichloroethane (25 mL) at 0° C. was treated with POCl$_3$ (1.5 mL). The resulting solution was warmed to ambient temperature and then treated with a solution of γ-oxo-1-H-pyrrole-3-butanoic acid ethyl ester (2.06 g) in 1,2-dichloroethane (10 mL). The reaction mixture was heated to 55° C. After 3.5 hours, the reaction was quenched with the addition of 1N NaOH (16 mL), and then stirred overnight at ambient temperature. The reaction mixture was extracted with ethyl acetate (150 mL), and the organic layer was dried (MgSO$_4$) and concentrated. The resulting oil was chromatographed on SiO$_2$ (100 g) using 4:1 hexane/ethyl actetate to afford 5-formyl-γ-oxo-1-H-pyrrole-3-butanoic acid ethyl ester (0.54 g).

Preparation 2

Compounds of Formula (G) and Formula (H)

A. A solution of N-(dimethylethoxycarbonyl)pyrrole-2-carboxaldehyde (10 g, 50 mmol) in THF (500 mL) at −30° C. under nitrogen was added dropwise to 3-[bis(trimethylsilyl)amino]phenylmagnesium chloride (55 mL of a 1M solution in THF, 55 mmol). After addition the reaction mixture was gradually warmed up and stirred at 0° C. for 1 hour, then at ambient temperature for 15 minutes. The reaction mixture was poured into ice water, and stirred for 30 minutes. The reaction mixture was extracted with ethyl ether (1 L). The combined organic layers were dried (Na$_2$SO$_4$) and concentrated. Chromatography on SiO$_2$ (700 g) using 1:1 hexane/ethyl acetate afforded [N-(dimethylethoxycarbonyl)pyrrol-2-yl](3-aminophenyl)methanol (11.2 g).

B. A solution of [N-(dimethylethoxycarbonyl)pyrrol-2-yl](3-aminophenyl)methanol (9.26 g, 32.1 mmol) in dichloromethane (30 mL) was treated with di-t-butyl dicarbonate (7.6 g, 34.8 mmol) and the mixture was refluxed for 15 hours. The solution was concentrated and purified by chromatography on SiO$_2$ (700 g) to afford [N-(dimethylethoxycarbonyl)pyrrol-2-yl][3-N-(dimethylethoxycarbonyl)aminophenyl]methanol (12.7 g).

C. A solution of [N-(dimethylethoxycarbonyl)pyrrol-2-yl][3-N-(dimethylethoxycarbonyl)aminophenyl]methanol (12.7 g, 0.033 mole) in dichloromethane (50 mL) was treated with MnO$_2$ (12.5 g, 0.147 mol) in portions. After 2 days, additional dichloromethane (40 mL) was added and the mixture was refluxed for 1 hour. The solid was filtered and the filtrate was concentrated to give [N-(dimethylethoxycarbonyl)pyrrol-2-yl][3-N-(dimethylethoxycarbonyl)aminophenyl]methanone.

Preparation 3

Compounds of Formula (K)

A. A solution of chlorosulfonylisocyanate in acetonitrile (25 mL) was added dropwise to a solution of 2-acetylpyrrole (10.9 g, 100 mmol) in acetonitrile (25 mL) at 0° C. The reaction mixture turned from yellow to black and was allowed to stir at ambient temperature for 2.5 h. The reaction mixture was cooled to 0° C. and DMF (10 mL) was added. The resulting reaction mixture was then heated to 50° C. for 10 minutes and then poured onto ice to afford a dark colored product. The product was dissolved in ethyl acetate and treated with activated charcoal and filtered. The ethyl acetate was evaporated to afford a tan-colored product. Recrystallization from ethyl acetate afforded 4-cyano-2-acetylpyrrole (4.5 g) as a tan solid.

B. In a similar manner, other compounds of formula (K) are prepared.

Preparation 4

Compounds of Formula (L)

A. To a solution of 2-acetyl-4-cyanopyrrole (3.6 g, 26.86 mmol) and di-t-butyl dicarbonate (10.2 g, 46.78 mmol) in methanol (200 mL) was added 10% palladium on charcoal (0.8 g) under nitrogen. The reaction mixture was shaken under H$_2$ (45 psi) for 2 hours, filtered through celite and concentrated to afford a purple oil which was purified by chromatography on SiO$_2$ using hexane/ethyl acetate as the eluent to 2-acetyl-4-(dimethylethoxycarbonyl)aminomethylpyrrole (5.1 g).

B. In a similar manner, other compounds of formula (L) are prepared.

Preparation 5

Compounds of Formula (N)

4-Bromopyrrole-2-carboxaldehyde was prepared by the method of Sonnet, P. E., *J. Org. Chem.* (1971), Vol. 36, p. 1005. A solution of 4-bromopyrrole-2-carboxaldehyde (2.61 g) and tetrahydrofuran (100 mL) was cooled to 0° C. LDA (7.5 mL of a 2 N solution in THF) was added dropwise and the mixture was stirred at 0° C. for 1 hour. Tosyl chloride (2.88 g) was then added. The resulting reaction mixture was allowed to warm to ambient temperature overnight. The reaction mixture was diluted with ethyl acetate (100 mL), washed with water (100 mL) and brine (100 mL), dried (Na$_2$SO$_4$) and concentrated. The dark colored solid was chromatographed on SiO$_2$ with 4:1 hexane/ethyl acetate to afford N-tosyl-4-bromo-2-pyrrolecarboxaldehyde (3.8 g).

Preparation 6

Compounds of Formula (P)

A. N-Tosyl-4-bromo-2-pyrrolecarboxaldehyde (198 mg, 0.603 mmol) was dissolved in absolute ethanol (20 mL) and heated below reflux. To this warmed solution, 3-methoxyphenylboronic acid (140 mg, 0.921 mmol) was added and the resulting mixture was diluted with toluene (20 mL) and stirred until dissolved. To this homogeneous solution, Pd(PPh$_3$)$_4$ (683 mg, 0.591 mmol) was added followed by saturated NaHCO$_3$ (5 mL) and the resulting solution was allowed to stir at reflux overnight. The reaction mixture was then diluted with ethyl acetate (50 mL) and washed with water (50 mL) and brine (50 mL), dried (Na$_2$SO$_4$) and concentrated to afford a syrup. To this syrup was added dichloromethane (5 mL) until a heterogeneous solution was obtained which was then diluted with 20% ethyl acetate in hexanes (20 mL) and purified by chromatography on SiO$_2$ using 20% ethyl acetate in hexanes to afford a product (130 mg). The product was then dissolved in methanol and ethyl acetate and the resulting solution was treated with 20% KOH (20 mL). After stirring overnight, the methanol was removed and the reaction mixture was extracted with ethyl acetate (2×100 mL). The combined organic layers were washed with brine (50 mL), dried (Na$_2$SO$_4$) and concentrated. The residue was purified by reverse phase HPLC (acetonitrile/water) to afford 4-(3-methoxyphenyl)-2-pyrrolecarboxaldehyde (70 mg).

B. In a similar, other compounds of formula (P) are prepared.

Preparation 7

Compounds of Formula (S) and Formula (T)

A. A solution of a 1-(1H-pyrrol-2-ylmethylene)pyrrolidinium perchlorate salt (5.2 g) in dichloroethane (100 mL) was treated with aluminum chloride (1.93 g). The mixture was cooled to 0° C., and then treated with 2-bromoacetyl chloride (2.2 mL). After stirring overnight at 0° C., the mixture was poured over crushed ice. Ether (60 mL) and sodium bicarbonate (1.93 g) were added and the mixture was stirred until the ice completely melted. The resulting mixture was extracted with ether and concentrated to afford 4-(bromoacetyl)-2-pyrrolecarboxaldehyde (1.88 g).

B. In a similar manner, other compounds of formula (T) are prepared.

Preparation 8

Compounds of Formula (Y)

A. Following the procedure described in PCT Published Patent Application, WO 99/10325, a solution of 4-cyanoaniline (10 g, 84 mmol) in dry dichloromethane (200 mL) under nitrogen was cooled to −78° C. To this stirred solution was added a solution of t-butylhypochlorite (10.9 mL, 84 mmol) in dry dichloromethane (20 mL). The resulting solution was stirred for 10 minutes. A solution of ethyl methylthioacetate (10.9 mL, 84 mmol) in dichloromethane (20 mL) was added dropwise. After 1 hour, triethylamine (12 mL, 86 mmol) was added dropwise to the solution and the resulting reaction mixture was allowed to warm to ambient temperature over 1 hour. The reaction mixture was washed with water, brine, dried ($Na_2SO_4$) and concentrated to afford an orange oil. This oil was dissolved in ether (200 mL) and treated with 2N HCl (15 mL). The reaction mixture was stirred vigorously at room temperature for 18 hours. The resulting solid was collected by filtration, washed with ether, and dried in vacuo to afford 5-cyano-3-methylthioindolin-2-one as a solid (11 g).

B. In a similar manner, other compounds of formula (Y) are prepared.

Preparation 9

Compounds of Formula (Z)

A. Following the procedure described in PCT Published Patent Application, WO 99/10325, to a solution of 5-cyano-3-methylthioindolin-2-one (11 g, 53.92 mmol) in tetrahydrofuran (200 mL) at ambient temperature was added saturated $NH_4Cl$ solution (200 mL), followed by activated zinc (50 g). The reaction mixture was stirred for 18 hours at ambient temperature. This mixture was filtered through celite. The organic layer was separated, dried ($Na_2SO_4$) and concentrated to afford a product as a semisolid. This product was chromatographed over $SiO_2$ using hexane/ethyl acetate to afford a tan solid which was washed with ether to afford 5-cyanoindolin-2-one (6 g) as an off-white solid.

B. In a similar manner, other compounds of formula (Z) are prepared.

Preparation 10

Compounds of Formula (AA)

A. A slurry of 5-cyanoindolin-2-one (5 g, 31.64 mmol) and 10% palladium on carbon (500 mg), was hydrogenated under 40 psi at ambient temperature temp. for 24 hours. Filtration through a pad of celite and concentration afforded 5-aminomethylindolin-2-one (5.5 g) as an orange oil.

B. In a similar manner, other compounds of formula (AA) are prepared.

Preparation 11

Compounds of Formula (CC) and Formula (DD)

A. A suspension of 5-nitroindolin-2-one (2.0 g, 11.13 mmol), and 10% palladium on carbon (500 mg) in methanol (100 mL) was hydrogenated for 2 hours under 45 psi. The reaction mixture was filtered through celite and the resulting cake was washed with methanol. The filtrate was concentrated to afford 5-aminoindolin-2-one as a tan-colored solid (1.6 g).

B. To a solution of 5-aminoindolin-2-one (8.76, 58.79 mmol) in tetrahydrofuran:dimethylformamide (400 mL:60 mL) was added trimethylsilylisocyanate (10.6 mL, 78.68 mmol) dropwise. The reaction mixture was stirred at ambient temperature for 18 hours. A tan-colored solid formed which was isolated by filtration, washed with ether and dried in vacuo to afford 5-ureidoindolin-2-one (8.5 g).

C. In a similar manner, other compounds of formula (CC) and (DD) are prepared.

Preparation 12

Compounds of Formula (EE)

A. 5-Nitroindolin-2-one (1.08 g, 8.8 mmol), 2-acetyl-4-(dimethylethoxycarbonylamino)methylpyrrole (1.5 g, 6.3 mmol), and piperidine (2.5 mL) was placed in a sealed tube reactor and the tube was stirred in an oil bath preheated at 85° C. After 3 hours, additional 5-nitroindolin-2-one (0.5 g) was added and the reaction stirred for another 1 hour. The reaction mixture was cooled, triturated with ethanol and left overnight at ambient temperature. A solid formed which was isolated by filtration and washed with ethanol to afford 5-nitro-3-[(4-(dimethylethoxycarbonylaminomethyl)pyrrol-2-yl)methylene]indolin-2-one as a yellow solid (0.8 g); $^1$H NMR (400 MHz, DMSO) δ 1.38 (s, 9H), 2.84 (s, 3H), 4.08 (d, 2H), 7.08 (d, 1H), 7.10 (m, 1H), 7.20 (t, 1H), 7.32 (s, 1H), 8.12 (dd, 1H), 8.48 (d, 1H) ppm.

B. In a similar manner, other compounds of formula (EE) are prepared.

Preparation 12

Compounds of Formulae (JJ), (KK), (LL) and (MM)

A. To a solution of imidazole-4-carboxaldehyde (13.65 g, 140 mmol) in tetrahydrofuran (300 mL) was added di-t-butyl dicarbonate (32.6 g, 150 mmol) and a catalytic amount of dimethylaminopyridine at ambient temperature. The resulting white suspension changed to a pale-yellow clear solution after 30 minutes at ambient temperature. The reaction was quenched with water and basified with sodium bicarbonate solution. The resulting reaction mixture was extracted with ethyl acetate, dried ($Na_2SO_4$), and concentrated to afford 27.4 g of 1-(dimethylethoxycarbonyl)imidazole-4-carboxaldehyde as a white solid.

B. To a solution of 1-(dimethylethoxycarbonyl)imidazole-4-carboxaldehyde (9.3 g, 47 mmol) in tetrahydrofuran (200 mL) was added a methyl Grignard reagent (6.6 mL, 50 mmol) at ambient temperature. The resulting reaction mixture was stirred overnight at ambient temperature. The reaction was quenched with water and extracted with ethyl acetate. The organic layer was dried ($Na_2SO_4$) and concentrated to afford 10 g of 4-(1-hydroxyethyl)-1-(dimethylethoxycarbonyl)imidazole as an oil.

C. 4-(1-Hydroxyethyl)-1-(dimethylethoxycarbonyl)imidazole (8.7 g, 41 mmol) was dissolved in methylene chloride (100 mL) and $MnO_2$ (10.7 g, 123 mmol) was added. The resulting reaction mixture was stirred overnight at ambient temperature. The reaction mixture was filtered, concentrated, and purified with silica column chromatography to afford 4 g of 4-acetyl-1-(dimethylethoxycarbonyl)imidazole and unreacted starting material.

D. 4-Acetyl-1-(dimethylethoxycarbonyl)imidazole (1 g, 4.8 mmol) was dissolved in methylene chloride (50 mL) and trifluoroacetic acid (2 mL) was added. The resulting reaction mixture was stirred overnight at ambient temperature. The reaction mixture was concentrated to afford 0.7 g of a white solid, 4-acetylimidazole, as a TFA salt.

E. In a similar manner, other compounds of formulae (JJ), (KK), (LL) and (MM) are prepared.

EXAMPLE 1

Compounds of Formula (Ia)

A. 5-Methoxyindolin-2-one was prepared by the method of Crestini, C.; Saladino, R. *Synth. Commun.* (1994), Vol. 24, NO. 20, p. 2835. A solution of 5-methoxyindolin-2-one (0.41 g, 2.5 mmol) and 2-pyrrolecarboxaldehyde (0.25 g, 2.6 mmol) in ethanol (5 mL) was treated with piperidine (0.05 g, 0.65 mmol). The reaction mixture was then heated to 85° C. for 3 hours. The reaction was then cooled to ambient temperature and the reaction mixture was chromatographed on $SiO_2$ (12 g) using 3:1 hexane/ethyl acetate to afford 5-methoxy-3-[(pyrrol-2-yl)methylene]indolin-2-one; (0.48 g); $^1$H NMR (400 MHz, DMSO-$d_6$) δ 3.74 (s, 3H), 6.30 (m, 1H), 6.60–6.80 (m, 3H), 7.30 (m, 1H), 7.35 (m, 1H), 7.76 (m, 1H), 10.80 (s, 1H) ppm.

B. A solution of 5-methoxy-3-[(pyrrol-2-yl)methylene]indolin-2-one; (0.10 g, 0.4 mmol) in dichloromethane (5 mL) was treated with $BBr_3$ solution (2.0 mL of a 1M solution in dichloromethane, 20 mmol, 5.0 eq.). After stirring overnight at ambient temperature, the reaction mixture was concentrated. The resulting oil was chromatographed on $SiO_2$ (5 g) using 1:3 hexane/ethyl acetate to afford 5-hydroxy-3-[(pyrrol-2-yl)methylene]indolin-2-one; (0.04 g); $^1$H NMR (400 MHz, DMSO-$d_6$) δ 6.30 (m, 1H), 6.60 (m, 2H), 6.78 (m, 1H), 6.98 (m, 1H), 7.32 (m, 1H), 7.58 (m, 1H), 9.00 (s, 1H), 10.60 (s, 1H) ppm.

C. Alternatively, a mixture of 5-methoxyindolin-2-one (0.50 g, 3.1 mmol), 2-acetylpyrrole (0.28 g, 2.4 mmol) and piperidine (0.60 g, 0.6 mmol) was placed in a sealed tube and melted. The reaction vessel was sealed and the mixture was heated to 130° C. overnight. The reaction was then cooled to ambient temperature and dissolved in ethyl acetate (2 mL). Chromatography ($SiO_2$, 15 g) using 2:1 hexane/ethyl acetate afforded 5-methoxy-3-[1-(pyrrol-2-yl)ethylidene]indolin-2-one; (0.24 g); $^1$H NMR (400 MHz, DMSO-$d_6$) δ 2.78 (s, 3H), 3.82 (s, 3H), 6.38 (m, 1H), 6.70–6.80 (m, 2H), 6.98 (m, 1H), 7.16 (m, 1H), 7.30 (m, 1H), 7.68 (m, 1H) ppm.

D. A solution of 5-methoxy-3-[1-(pyrrol-2-yl)ethylidene]indolin-2-one; (0.12 g, 0.5 mmol) in dichloromethane (5 mL) was treated with $BBr_3$ solution (1.5 mL of a 1M solution in dichloromethane, 1.5 mmol, 3.0 eq.). After stirring overnight at ambient temperature, the reaction was quenched by water (10 mL). The organic layer was separated. The aqueous layer was neutralized with saturated $NaHCO_3$ solution and extracted with ethyl acetate (2×20 mL). The combined organic layers were concentrated. Reverse phase HPLC using acetonitrile/water afforded 5-hydroxy-3-[1-(pyrrol-2-yl)ethylidene]indolin-2-one; (0.04 g); $^1$H NMR (400 MHz, DMSO-$d_6$) δ 2.74 (s, 3H), 6.38 (m, 1H), 6.62 (m, 1H), 6.70 (m, 1H), 7.08 (m, 1H), 7.20 (m, 1H), 7.32 (m, 1H), 8.96 (s, 1H), 10.78 (s, 1H) ppm.

E. In a similar manner as described above in Paragraphs A and B or Paragraphs C and D, but using the appropriately substituted starting material, the following compounds were made:

5-acetamido-3-[1-(pyrrol-2-yl)ethylidene]indolin-2-one; $^1$H NMR (400 MHz, DMSO-$d_6$) δ 2.16 (s, 3H), 2.84 (s, 3H), 6.44 (m, 1H), 6.92 (d, 1H), 7.20 (m, 1H), 7.44 (s, 1H), 7.56 (m, 1H), 8.10 (m, 1H), 9.94 (s, 1H), 11.06 (s, 1H) ppm;

5-(pyridin-3-yl)carbonylamino-3-[1-(pyrrol-2-yl)ethylidene]indolin-2-one; $^1$H NMR (400 MHz, DMSO-$d_6$) δ 2.74 (s, 3H), 6.36 (m, 1H), 6.88 (d, 1H), 7.08 (m, 1H), 7.32 (m, 1H), 7.58 (m, 1H), 7.64 (m, 1H), 8.16 (m, 1H), 8.26 (m, 1H), 8.76 (m, 1H), 9.10 (s, 1H), 10.32 (s, 1H), 10.98 (s, 1H) ppm;

5-(pyridin-4-yl)carbonylamino-3-[1-(pyrrol-2-yl)ethylidene]indolin-2-one; $^1$H NMR (400 MHz, DMSO-$d_6$) δ 2.92 (s, 3H), 6.50 (m, 1H), 7.04 (d, 1H), 7.24 (m, 1H), 7.50 (m, 1H), 7.80 (m, 1H), 8.02 (d, 2H), 8.28 (s, 1H), 8.92 (d, 2H), 10.54 (s, 1H), 11.18 (s, 1H) ppm;

5-guanidino-3-[1-(pyrrol-2-yl)ethylidene]indolin-2-one; $^1$H NMR (400 MHz, DMSO-$d_6$) δ 2.78 (s, 3H), 6.40 (m, 1H), 6.98 (d, 1H), 7.06 (m, 1H), 7.10 (m, 1H), 7.24 (m, 3H), 7.40 (m, 1H), 7.58 (m, 1H), 9.44 (s, 1H), 10.96 (s, 1H) ppm;

5-aminosulfonylamino-3-[1-(pyrrol-2-yl)ethylidene]indolin-2-one; $^1$H NMR (400 MHz, DMSO-$d_6$) δ 2.74 (s, 3H), 6.38 (m, 1H), 6.82 (d, 1H), 6.90 (s, 2H), 7.04 (m, 1H), 7.10 (m, 1H), 7.36 (m, 1H), 7.64 (m, 1H), 8.92 (s, 1H), 10.96 (s, 1H) ppm;

5-(1,1-dimethylethoxy)carbonylaminosulfonylamino-3-[1-(pyrrol-2-yl)ethylidene]indolin-2-one; $^1$H NMR (400 MHz, DMSO-$d_6$) δ 1.38 (s, 9H), 2.72 (s, 3H), 6.38 (m, 1H), 6.84 (m, 1H), 7.00 (m, 1H), 7.10 (m, 1H), 7.36 (m, 1H), 7.58 (m, 1H), 9.90 (s, 1H), 11.00 (s, 1H) ppm;

5-(4-aminopiperidin-1-ylcarbonylamino)-3-[1-(pyrrol-2-yl)ethylidene]indolin-2-one;

$^1$H NMR (400 MHz, DMSO-$d_6$) δ 1.4 (m, 2H), 1.9 (m, 2H), 2.7 (s, 3H), 2.9 (m, 2H), 3.2 (m, 1H), 4.1 (m, 2H), 6.4 (s, 1H), 6.8 (d, 1H), 7.0 (m, 1H), 7.3 (m, 2H), 7.8 (s, 1H), 7.9 (m, 2H), 8.5 (s, 1H), 10.9 (s, 1H) ppm;

6-chloro-3-[(pyrrol-2-yl)methylene]indolin-2-one; $^1$H NMR (500 MHz, DMSO-$d_6$) δ 6.38 (m, 1H), 6.84–6.91 (m, 2H), 7.04 (dd, 1H), 7.39 (s, 1H), 7.64 (d, 1H), 7.79 (s, 1H), 11.00 (s, 1H), 13.24 (s, 1H) ppm;

5-chloro-3-[(pyrrol-2-yl)methylene]indolin-2-one; $^1$H NMR (500 MHz, DMSO-$d_6$) δ 6.39 (m, 1H), 6.83–6.91 (m, 2H), 7.18 (dd, 1H), 7.39 (s, 1H), 7.75 (d, 1H), 7.89 (s, 1H), 10.98 (s, 1H), 13.30 (s, 1H) ppm;

5-bromo-3-[(pyrrol-2-yl)methylene]indolin-2-one; $^1$H NMR (500 MHz, DMSO-d$_6$) δ 6.38 (m, 1H), 6.84 (m, 2H), 7.29 (dd, 1H), 7.40 (s, 1H), 7.88 (m, 2H), 10.97 (s, 1H), 13.29 (s, 1H) ppm;

6-fluoro-3-[(pyrrol-2-yl)methylene]indolin-2-one; $^1$H NMR (500 MHz, DMSO-d$_6$) δ 6.37 (m, 1H), 6.70 (m, 1H), 6.78–6.84 (m, 2H), 7.34 (s, 1H), 7.64 (m, 1H), 7.71 (s, 1H), 11.00 (s, 1H), 13.19 (s, 1H) ppm;

6-methyl-3-[((1-methyl)pyrrol-2-yl)methylene]indolin-2-one; $^1$H NMR (500 MHz, DMSO-d$_6$) δ 2.30 (s, 3H), 3.78 (s, 3H), 6.29 (m, 1H), 6.68 (s, 1H), 6.76 (d, 1H), 7.14 (m, 1H), 7.38 (s, 1H), 7.85 (d, 1H), 8.30 (s, 1H), 10.38 (s, 1H) ppm; and $^1$H NMR (500 MHz, DMSO-d$_6$) δ 3.88 (s, 3H), 6.20 (m, 1H), 6.64 (s, 1H), 6.99 (m, 1H), 7.12 (m, 1H), 7.48 (s, 1H), 7.58 (d, 1H), 8.18 (d, 1H), 10.32 (s, 1H) ppm;

6-trifluoromethyl-3-[(1-methylpyrrol-2-yl)methylene]indolin-2-one; $^1$H NMR (500 MHz, DMSO-d$_6$) δ 3.82 (s, 3H), 6.38 (m, 1H), 7.10 (s, 1H), 7.16 (m, 1H), 7.24–7.32 (m, 2H), 7.62 (s, 1H), 8.16 (d, 1H), 10.72 (s, 1H) ppm; and $^1$H NMR (500 MHz, DMSO-d$_6$) δ 3.92 (s, 3H), 6.28 (m, 1H), 7.05 (s, 1H), 7.24–7.32 (m, 2H), 7.77 (s, 1H), 7.94 (d, 1H), 8.37 (d, 1H), 10.47 (s, 1H) ppm;

5-(4-methoxy)phenyl-3-[(1-methylpyrrol-2-yl)methylene]indolin-2-one; $^1$H NMR (500 MHz, DMSO-d$_6$) δ 3.70 (m, 6H), 6.34 (m, 1H), 6.92 (d, 1H), 7.02 (d, 2H), 7.19 (dd, 1H), 7.42 (dd, 1H), 7.48 (d, 2H), 7.70 (s, 1H), 8.18 (s, 1H), 8.28 (m, 1H), 10.51 (m, 1H) ppm;

5-(4-(1,1-dimethyl)ethyl)phenyl-3-[(1-methylpyrrol-2-yl)methylene]indolin-2-one;

3-[(1-methylpyrrol-2-yl)methylene]indolin-2-one; $^1$H NMR (400 MHz, DMSO-d$_6$) δ 3.8 (s, 1H), 6.30 (m, 1H), 6.85 (d, 1H), 6.9 (t, 1H), 7.00 (d, 1H), 7.35 (s, 1H), 7.40 (s, 1H), 7.95 (d, 1H), 10.4 (s, 1H) ppm;

(Z)-3-[(1-phenylsulfonylpyrrol-2-yl)methylene]indolin-2-one; $^1$H NMR (400 MHz, DMSO-d$_6$) δ 6.60 (m, 1H), 6.80 d, 1H), 7.00 (t, 1H), 7.20 (t, 1H), 7.45 (d, 1H), 7.60 (t, 2H), 7.70 (d, 1H), 7.80 (m, 1H), 7.90 (m, 3H), 8.30 (m, 1H), 10.6 (s, 1H) ppm;

(E)-3-[(1-phenylsulfonylpyrrol-2-yl)methylene]indolin-2-one; $^1$H NMR (400 MHz, DMSO-d$_6$) δ 6.60 (m, 1H), 6.80 (m, 2H), 7.10 (m, 1H), 7.20 (t, 1H), 7.55 (m, 3H), 7.65 (m, 2H), 7.75 (m, 1H), 7.80 (d, 2H), 10.6 (s, 1H) ppm;

3-[(3,5-dimethyl-4-ethylpyrrol-2-yl)methylene]indolin-2-one; $^1$H NMR (400 MHz, DMSO-d$_6$) δ 1.00 (t, 0.3H), 2.20 (s, 3H), 2.25 (s, 3H), 2.35 (q, 2H), 6.80 (d, 1H), 6.90 (m, 1H), 7.00 (m, 1H), 7.55 (s, 1H), 7.7 (d, 1H), 10.7 (s, 1H) ppm;

5,6-dimethoxy-3-[(pyrrol-2-yl)methylene]indolin-2-one; $^1$H NMR (400 MHz, CDCl$_3$) δ 3.88 (s, 3H), 3.92 (s, 3H), 6.34 (m, 1H), 6.50 (m, 1H), 6.72 (m, 1H), 7.02 (m, 1H), 7.14 (m, 1H), 7.26 (m, 1H), 7.76 (s, 1H) ppm;

4-methyl-3-[(pyrrol-2-yl)methylene]indolin-2-one; $^1$H NMR (400 MHz, DMSO-d$_6$) δ 2.58 (s, 3H), 6.30 (m, 1H), 6.72 (m, 1H), 6.88 (m, 1H), 7.00 (m, 1H), 7.30 (m, 1H), 7.60 (s, 1H), 10.90 (s, 1H) ppm;

7-methyl-3-[(pyrrol-2-yl)methylene]indolin-2-one; $^1$H NMR (400 MHz, CDCl$_3$) δ 2.50 (s, 3H), 3.50 (m, 1H), 6.36 (m, 1H), 6.76 (m, 1H), 6.98 (m, 2H), 7.16 (m, 1H), 7.30 (m, 1H), 7.42 (m, 1H), 8.20 (m, 1H) ppm;

3-[(5-ethylpyrrol-2-yl)methylene]indolin-2-one; $^1$H NMR (400 MHz, DMSO-d$_6$) δ 1.10 (t, 3H), 2.60 (q, 2H), 6.00 (m, 1H), 6.70 (m, 1H), 6.80 (d, 1H), 6.90 (m, 1H), 7.00 (m, 1H), 7.50 (m, 1H), 7.60 (d, 1H), 10.8 (s, 1H) ppm;

5-methyl-3-[(pyrrol-2-yl)methylene]indolin-2-one; $^1$H NMR (400 MHz, DMSO-d$_6$) δ 2.36 (s, 3H), 6.36 (m, 1H), 6.76 (m, 2H), 6.98 (m, 1H), 7.16 (m, 1H), 7.28 (m, 1H), 7.40 (s, 1H), 8.00 (s, 1H) ppm;

6-carboxy-3-[(pyrrol-2-yl)methylene]indolin-2-one; $^1$H NMR (400 MHz, DMSO-d$_6$) δ 6.43 (s, 1H), 6.95 (s, 1H), 7.44 (s, 1H), 7.46 (s, 1H), 7.65 (d, 1H), 7.75 (d, 1H), 7.93 (s, 1H), 11.08 (s, 1H) ppm;

5-methoxy-3-[(5-ethylpyrrol-2-yl)methylene]indolin-2-one; $^1$H NMR (400 MHz, DMSO-d$_6$) δ 1.22 (t, 3H), 2.72 (m, 2H), 3.74 (s, 3H), 6.16 (m, 1H), 6.64–6.78 (m, 3H), 7.26 (m, 1H), 7.68 (m, 1H), 10.58 (s, 1H) ppm;

5-hydroxy-3-[(5-ethylpyrrol-2-yl)methylene]indolin-2-one; $^1$H NMR (400 MHz, DMSO-d$_6$) δ 1.22 (t, 3H), 2.70 (m, 2H), 6.10 (m, 1H), 6.52 (m, 1H), 6.62 (m, 1H), 6.70 (m, 1H), 6.92 (m, 1H), 7.48 (m, 1H), 10.50 (s, 1H) ppm;

5-aminosulfonyl-3-[(pyrrol-2-yl)methylene]indolin-2-one; $^1$H NMR (400 MHz, DMSO-d$_6$) δ 40 (s, 1H), 6.96 (s, 1H), 7.02 (d, 1H), 7.15 (s, 2H), 7.42 (s, 1H), 7.64 (d, 1H), 7.92 (s, 1H), 8.08 (s, 1H), 11.25 (s, 1H) ppm;

3-[(4-nitropyrrol-2-yl)methylene]indolin-2-one; $^1$H NMR (400 MHz, DMSO-d$_6$) δ 6.85 (d, 1H), 7.00 (t, 1H), 7.20 (t, 1H), 7.30 (d, 1H), 7.60 (d, 1H), 7.70 (s, 1H), 8.20 (d, 1H), 11.0 (s, 1H) ppm;

7-methoxy-3-[(pyrrol-2-yl)methylene]indolin-2-one; $^1$H NMR (400 MHz, DMSO-d$_6$) δ 3.80 (s, 3H), 6.36 (m, 1H), 6.82 (m, 2H), 6.92 (m, 1H), 7.22 (m, 1H), 7.34 (m, 1H), 7.70 (m, 1H), 10.90 (s, 1H) ppm;

7-hydroxy-3-[(pyrrol-2-yl)methylene]indolin-2-one; $^1$H NMR (400 MHz, DMSO-d$_6$) δ 6.36 (m, 1H), 6.62 (m, 1H), 6.80 (m, 2H), 7.08 (m, 1H), 7.30 (m, 1H), 7.62 (m, 1H), 9.44 (m, 1H), 10.90 (s, 1H) ppm;

4-methoxy-3-[(pyrrol-2-yl)methylene]indolin-2-one; $^1$H NMR (400 MHz, DMSO-d$_6$) δ 3.92 (s, 3H), 6.30 (m, 1H), 6.52 (m, 1H), 6.60 (m, 1H), 6.74 (m, 1H), 7.08 (m, 1H), 7.30 (m, 1H), 7.92 (s, 1H), 10.90 (s, 1H) ppm;

4-hydroxy-3-[(pyrrol-2-yl)methylene]indolin-2-one; $^1$H NMR (400 MHz, DMSO-d$_6$) δ 6.28 (m, 1H), 6.40 (m, 1H), 6.48 (m, 1H), 6.70 (m, 1H), 6.92 (m, 1H), 7.20 (m, 1H), 7.90 (m, 1H), 10.20 (s, 1H), 10.76 (s, 1H) ppm;

5-(2-hydroxyethyl)aminosulfonyl-3-[(pyrrol-2-yl)methylene]indolin-2-one; $^1$H NMR (400 MHz, DMSO-d$_6$) δ 2.78 (t, 2H), 3.35 (t, 2H), 4.62 (br s, 1H), 6.40 (s, 1H), 6.96 (s, 1H), 7.02 (d, 1H), 7.30 (br s, 1H), 7.42 (s, 1H), 7.55 (d, 1H), 7.92 (s, 1H), 8.08 (s, 1H), 11.25 (s, 1H) ppm;

6-methoxy-3-[(pyrrol-2-yl)methylene]indolin-2-one; $^1$H NMR (400 MHz, DMSO-d$_6$) δ 3.77 (s, 3H), 6.32 (m, 1H), 6.44 (m, 1H), 6.58 (m, 1H), 6.76 (m, 1H), 7.30 (m, 1H), 7.50–7.66 (m, 2H), 10.84 (s, 1H) ppm;

3-[1-(pyrrol-2-yl)ethylidene]indolin-2-one; $^1$H NMR (400 MHz, DMSO-d$_6$) δ 2.70 (s, 3H), 6.30 (m, 1H), 6.85 (d, 1H), 6.90 (t, 1H), 7.00 (m, 1H), 7.20 (m, 1H), 7.30 (m, 1H), 7.65 (d, 1H), 11.0 (br, 1H) ppm;

6-hydroxy-3-[(pyrrol-2-yl)methylene]indolin-2-one; $^1$H NMR (400 MHz, DMSO-d$_6$) δ 6.26 (m, 1H), 6.30 (m, 1H), 6.38 (m, 1H), 6.70 (m, 1H), 7.20 (m, 1H), 7.36 (m, 1H), 7.44 (m, 2H), 9.50 (m, 1H), 10.70 (s, 1H) ppm;

5-dimethylaminosulfonyl-3-[(pyrrol-2-yl)methylene]indolin-2-one; $^1$H NMR (400 MHz, DMSO-d$_6$) δ 2.60 (s, 6H), 6.40 (s, 1H), 6.90 (s, 1H), 7.02 (d, 1H), 7.40 (s, 1H), 7.50 (d, 1H), 8.00 (s, 1H), 8.08 (s, 1H), 11.30 (s, 1H) ppm;

5-methylaminosulfonyl-3-[(pyrrol-2-yl)methylene]indolin-2-one; $^1$H NMR (400 MHz, DMSO-d$_6$) δ 2.40 (d, 3H), 6.40 (s, 1H), 6.96 (s, 1H), 7.05 (d, 1H), 7.20 (br s, 1H), 7.42 (s, 1H), 7.55 (d, 1H), 7.92 (s, 1H), 8.08 (s, 1H), 11.25 (s, 1H) ppm;

5-methoxy-4-methyl-3-[(pyrrol-2-yl)methylene]indolin-2-one; $^1$H NMR (400 MHz, DMSO-d$_6$) δ 2.40 (s, 3H), 3.72 (s, 3H), 6.30 (m, 1H), 6.64 (m, 1H), 6.78 (m, 1H), 6.90 (m, 1H), 7.30 (m, 1H), 7.70 (m, 1H), 10.70 (s, 1H) ppm;

5-hydroxy-4-methyl-3-[(pyrrol-2-yl)methylene]indolin-2-one; $^1$H NMR (400 MHz, DMSO-d$_6$) δ 2.38 (s, 3H), 6.30 (m, 1H), 6.50 (m, 1H), 6.60 (m, 1H), 6.88 (m, 1H), 7.26 (m, 1H), 7.62 (m, 1H), 8.90 (s, 1H), 10.60 (s, 1H) ppm;

5,6-dihydroxy-3-[(pyrrol-2-yl)methylene]indolin-2-one; $^1$H NMR (400 MHz, DMSO-d$_6$) δ 6.20 (m, 1H), 6.28 (m, 1H), 6.44 (m, 1H), 6.90 (m, 1H), 7.16 (m, 1H), 7.28 (m, 1H), 8.34 (m, 1H), 9.10 (s, 1H), 10.38 (s, 1H) ppm;

5-carboxy-3-[(pyrrol-2-yl)methylene]indolin-2-one; $^1$H NMR (400 MHz, DMSO-d$_6$) δ 6.40 (s, 1H), 6.85 (s, 1H), 6.90 (d, 1H), 7.40 (s, 1H), 7.80 (d, 1H), 7.92 (s, 1H), 8.20 (s, 1H), 11.25 (s, 1H) ppm;

5-aminosulfonyl-3-[(1-pyrrol-2-yl)ethylidene]indolin-2-one; $^1$H NMR (400 MHz, DMSO-d$_6$) δ 6.40 (s, 1H), 7.04 (d, 1H), 7.21 (br s, 1H), 7.22 (s, 2H), 7.42 (s, 1H), 7.64 (d, 1H), 8.16 (s, 1H), 11.40 (s, 1H) ppm;

5-hydroxy-3-[(4-methylpyrrol-2-yl)methylene]indolin-2-one; $^1$H NMR (400 MHz, DMSO-d$_6$) δ 2.30 (s, 3H), 6.15 (m, 1H), 6.56 (m, 1H), 6.62 (m, 1H), 7.12 (m, 1H), 7.20 (m, 1H), 7.48 (m, 1H), 8.88 (s, 1H), 10.52 (s, 1H) ppm;

5-methylsulfonylamino-3-[(pyrrol-2-yl)methylene]indolin-2-one; $^1$H NMR (400 MHz, DMSO-d$_6$) δ 2.92 (s, 3H), 6.32 (m, 1H), 6.80 (m, 1H), 6.90 (m, 1H), 6.98 (m, 1H), 7.32 (m, 1H), 7.44 (m, 1H), 7.68 (s, 1H), 9.36 (s, 1H), 10.90 (s, 1H) ppm;

5-phenylaminosulfonyl-3-[(pyrrol-2-yl)methylene]indolin-2-one; $^1$H NMR (400 MHz, DMSO-d$_6$) δ 6.40 (s, 1H), 6.90–6.96 (m, 3H), 7.10 (d, 2H), 7.18 (t, 2H), 7.40 (s, 1H), 7.50 (d, 1H), 7.90 (s, 1H), 8.00 (s, 1H), 10.20 (br, s, 1H), 11.25 (s, 1H) ppm;

5-hydroxy-3-[(5-methylpyrrol-2-yl)methylene]indolin-2-one; $^1$H NMR (400 MHz, DMSO-d$_6$) δ 2.40 (s, 3H), 6.14 (m, 1H), 6.58 (m, 1H), 6.70 (m, 1H), 6.78 (m, 1H), 7.00 (d, 1H), 7.52 (s, 1H), 8.96 (s, 1H), 10.56 (s, 1H) ppm;

5-hydroxy-3-[(3-methylpyrrol-2-yl)methylene]indolin-2-one; $^1$H NMR (400 MHz, DMSO-d$_6$) δ 2.06 (s, 3H), 6.52–6.64 (m, 3H), 6.92 (m, 1H), 7.10 (m, 1H), 7.48 (m, 1H), 8.94 (s, 1H), 10.52 (s, 1H) ppm;

5-methoxy-3-[(4-nitropyrrol-2-yl)methylene]indolin-2-one; $^1$H NMR (400 MHz, DMSO-d$_6$) δ 3.74 (s, 3H), 6.78 (m, 2H), 7.30 (m, 2H), 7.78 (s, 1H), 8.22 (m, 1H), 10.96 (s, 1H) ppm;

5-methoxycarbonyl-3-[(pyrrol-2-yl)methylene]indolin-2-one; $^1$H NMR (400 MHz, DMSO-d$_6$) δ 3.90 (s, 3H), 6.40 (s, 1H), 6.90 (s, 1H), 7.00 (d, 1H), 7.40 (s, 1H), 7.80 (d, 1H), 8.00 (s, 1H), 8.30 (s, 1H), 11.25 (s, 1H) ppm;

5-aminocarbonyl-3-[(pyrrol-2-yl)methylene]indolin-2-one; $^1$H NMR (400 MHz, DMSO-d$_6$) δ 6.35 (s, 1H), 6.85 (s, 1H), 6.90 (d, 1H), 7.39 (s, 1H), 7.68 (d, 1H), 7.72 (s, 1H), 8.15 (s, 1H), 11.10 (s, 1H) ppm;

3-[(3,5-dimethylpyrrol-2-yl)methylene]indolin-2-one; $^1$H NMR (400 MHz, DMSO-d$_6$) δ 2.26 (s, 3H), 2.30 (s, 3H), 5.96 (s, 1H), 6.84 (m, 1H), 6.92 (m, 1H), 7.06 (m, 1H), 7.56 (s, 1H), 7.70 (m, 1H), 10.76 (s, 1H) ppm;

5-methoxy-3-[(3,5-dimethylpyrrol-2-yl)methylene]indolin-2-one; $^1$H NMR (400 MHz, DMSO-d$_6$) δ 2.24 (s, 3H), 2.28 (s, 3H), 3.74 (s, 3H), 5.96 (m, 1H), 6.64 (m, 1H), 6.74 (s, 1H), 7.38 (s, 1H), 7.56 (s, 1H), 10.56 (s, 1H) ppm;

5-methoxy-1-methyl-3-[(pyrrol-2-yl)methylene]indolin-2-one; $^1$H NMR (400 MHz, DMSO-d$_6$) δ 3.34 (s, 3H), 3.84 (s, 3H), 6.38 (m, 1H), 6.76 (m, 3H), 7.08 (dd, 1H), 7.16 (s, 1H), 7.26 (s, 1H), 7.38 (s, 1H) ppm;

5-hydroxy-1-methyl-3-[(pyrrol-2-yl)methylene]indolin-2-one; $^1$H NMR (400 MHz, DMSO-d$_6$) δ 3.20 (s, 1H), 6.34 (m, 1H), 6.60 (d, 1H), 6.82 (s, 1H), 7.14 (m, 1H), 7.30 (s, 1H), 7.62 (s, 1H), 9.06 (brs, 1H) ppm;

5-hydroxy-3-[(3,5-dimethylpyrrol-2-yl)methylene]indolin-2-one; $^1$H NMR (400 MHz, DMSO-d$_6$) δ 2.24 (s, 3H), 2.28 (s, 3H), 5.96 (m, 1H), 6.50 (m, 1H), 6.62 (s, 1H), 7.08 (s, 1H), 7.38 (s, 1H), 8.82 (s, 1H), 10.44 (s, 1H) ppm;

4-carboxy-3-[(pyrrol-2-yl)methylene]indolin-2-one; $^1$H NMR (400 MHz, DMSO-d$_6$) δ 6.40 (s, 1H), 6.80 (s, 1H), 7.20 (d, 1H), 7.30 (t, 1H), 7.42–7.48 (m, 2H), 8.53 (s, 1H), 11.05 (s, 1H) ppm;

5-acetamido-3-[(pyrrol-2-yl)methylene]indolin-2-one; $^1$H NMR (400 MHz, DMSO-d$_6$) δ 2.00 (s, 3H), 6.32 (m, 1H), 6.78 (d, 1H), 6.98 (m, 1H), 7.14 (d, 1H), 7.34 (s, 1H), 7.56 (s, 1H), 7.88 (s, 1H), 9.78 (s, 1H), 10.78 (s, 1H) ppm;

4-methoxy-5-methoxycarbonyl-7-chloro-3-[(pyrrol-2-yl)methylene]indolin-2-one; $^1$H NMR (400 MHz, DMSO-d$_6$) δ 3.84 (s, 3H), 3.88 (s, 3H), 6.42 (s, 1H), 7.08 (m, 1H), 7.48 (m, 1H), 7.60 (s, 1H), 8.08 (m, 1H), 11.68 (s, 1H) ppm;

5-trifluoroacetamido-3-[(pyrrol-2-yl)methylene]indolin-2-one; $^1$H NMR (400 MHz, DMSO-d$_6$) δ 6.34 (m, 1H), 6.76 (dm 2H), 7.24 (d, 1H), 7.90 (s, 1H), 10.98 (s, 1H), 11.14 (s, 1H) ppm;

4-acetamido-3-[(pyrrol-2-yl)methylene]indolin-2-one; $^1$H NMR (400 MHz, DMSO-d$_6$) δ 2.00 (s, 3H), 10.8 (s, 1H) 6.30 (m, 1H), 6.80 (m, 1H), 7.00 (dd, 1H), 7.30 (m, 1H), 7.40 (s, 1H), 7.50 (d, 1H), 7.60 (s, 1H), 10.0 (s, 1H) ppm;

5-(pyrrolidin-1-yl)acetamido-3-[(pyrrol-2-yl)methylene]indolin-2-one; $^1$H NMR (400 MHz, DMSO-d$_6$) δ 1.70 (m, 4H), 2.60 (m, 4H), 3.20 (s, 2H), 6.30 (m, 1H), 6.80 (m, 1H), 7.10 (m, 1H), 7.30 (s, 1H), 7.50 (m, 2H), 7.60 (s, 1H), 9.70 (s, 1H), 10.8 (s, 1H) ppm;

5-aminocarbonyl-3-[3-(pyrrol-2-yl)ethylidene]indolin-2-one; $^1$H NMR (400 MHz, DMSO-d$_6$) δ 3.08 (s, 3H), 6.60 (s, 1H), 7.20 (d, 1H), 7.38 (br s, 1H), 7.45 (br s, 1H), 7.60 (s, 1H), 8.00 (d, 1H), 8.20 (brs, 1H), 8.40 (s, 1H), 11.10 (s, 1H) ppm;

4-ethoxycarbonylmethylamino-3-[(pyrrol-2-yl)methylene]indolin-2-one; $^1$H NMR (400 MHz, DMSO-d$_6$) δ 1.20 (t, 3H), 3.90 (d, 2H), 4.10 (q, 2H), 6.10 (s, 1H), 6.20 (m, 1H), 6.30 (m, 2H), 6.60 (m, 1H), 7.20 (m, 1H), 7.30 (m, 2H), 10.6 (s, 1H) ppm;

5-aminosulfonyl-3-[1-(pyrrol-2-yl)propylidene]indolin-2-one; $^1$H NMR (400 MHz, DMSO-d$_6$) δ 1.35 (t, 3H), 3.18 (q, 2H), 6.40 (s, 1H), 7.02 (d, 1H), 7.14 (br s, 1H), 7.22 (s, 2H), 7.38 (s, 1H), 7.64 (d, 1H), 7.98 (s, 1H), 11.40 (s, 1H) ppm;

5-aminosulfonyl-3-[(pyrrol-2-yl)(phenyl)methylene]indolin-2-one; $^1$H NMR (400 MHz, DMSO-d$_6$) δ 5.82 (s, 1H), 5.86 (m, 1H), 6.25 (m, 1H), 6.85 (s, 2H), 6.95 (d, 1H), 7.24–7.28 (m, 2H), 7.42 (br s, 1H), 7.48 (d, 1H), 7.50–7.52 (m, 3H), 11.40 (s, 1H) ppm;

5-acetamidomethyl-3-[1-(pyrrol-2-yl)ethylidene]indolin-2-one; $^1$H NMR (400 MHz, DMSO-d$_6$) δ 2.90 (s, 3H), 2.78 (s, 3H), 4.22 (d, 2H), 6.38 (m, 1H), 6.82 (d, 1H), 7.18 (m, 2H), 7.30 (m, 1H), 7.60 (s, 1H), 8.26 (t, 1H), 10.96 (s, 1H) ppm;

5-(1,1-dimethylethoxy)carbonylaminomethyl-3-[1-(pyrrol-2-yl)ethylidene]indolin-2-one; $^1$H NMR (400 MHz, DMSO-d$_6$) δ 1.60 (s, 9H), 2.92 (s, 3H), 4.28 (d, 2H), 6.50 (m, 1H), 6.98 (d, 1H), 7.20 (m, 2H), 7.48 (m, 1H), 7.52 (t, 1H), 7.78 (s, 1H), 11.12 (s, 1H) ppm;

5-aminoacetamido-3-[1-(pyrrol-2-yl)ethylidene]indolin-2-one; $^1$H NMR (400 MHz, DMSO-d$_6$) δ 2.76 (s, 3H), 3.78 (s, 2H), 6.38 (m, 1H), 6.90 (m, 1H), 7.10 (m, 2H), 8.10 (m, 3H), 10.32 (s, 1H), 11.00 (s, 1H) ppm;

5-ethoxycarbonylmethylamino-3-[1-(pyrrol-2-yl)ethylidene]indolin-2-one; $^1$H NMR (400 MHz, DMSO-d$_6$) δ 1.20 (s, 3H), 2.70 (s, 3H), 3.90 (s, 2H), 4.12 (m, 2H), 5.70

(t, 1H), 6.36 (m, 1H), 6.40 (m, 1H), 6.64 (m, 1H), 7.02 (m, 2H), 7.30 (m, 1H), 10.60 (t, 1H) ppm;

5-aminocarbonylmethylamino-3-[1-(pyrrol-2-yl)ethylidene]indolin-2-one; $^1$H NMR (400 MHz, DMSO-$d_6$) δ 2.70 (s, 3H), 3.60 (m, 2H), 5.60 (t, 1H), 6.36 (m, 2H), 6.70 (m, 1H), 7.00–7.15 (m, 3H), 7.30 (m, 1H), 7.36 (m, 1H), 10.62 (s, 1H) ppm;

5-aminosulfonyl-3-[(4-carboxy-3-methylpyrrol-2-yl)methylene]indolin-2-one; $^1$H NMR (400 MHz, DMSO-$d_6$) δ 1.45 (m, 6H), 2.56 (s, 3H), 2.74 (m, 4H), 6.98 (d, 1H), 7.60 (d, 1H), 7.73 (s, 1H), 7.78 (s, 1H), 8.24(s, 1H) ppm;

5-aminosulfonyl-3-[(3-methyl-4-(3-(piperidin-1-yl)propyl)aminocarbonylpyrrol-2-yl)methylene]indolin-2-one; $^1$H NMR (400 MHz, DMSO-$d_6$) δ 1.36 (m, 1H), 1.64 (m, 3H), 1.82 (m, 4H), 2.84 (m, 2H), 2.96 (s, 3H), 3.04 (m, 2H), 3.23 (m, 2H), 3.41 (m, 2H), 7.19 (d, 1H), 7.40 (s, 2H), 7.76 (d, 1H), 7.85 (s, 1H), 8.05 (s, 1H), 8.27 (t, 1H), 8.54 (s, 1H) ppm;

5-acetamido-3-[1-(4-aminomethylpyrrol-2-yl)ethylidene]indolin-2-one; $^1$H NMR (400 MHz, DMSO-$d_6$) δ 2.04 (s, 3H), 2.70 (s, 3H), 3.96 (d, 2H), 6.86 (d, 1H), 7.14 (s, 1H), 7.44 (s, 1H), 7.48 (s, 1H), 8.06 (s, 1H), 8.16 (s, 2H), 9.90 (s, 1H), 11.00 (s, 1H) ppm; and 5-acetamido-3-[1-(4-(2-aminoethylcarbamylmethyl)pyrrol-2-yl)ethylidene]indolin-2-one; $^1$H NMR (400 MHz, DMSO-$d_6$) δ 2.26 (s, 3H), 2.72 (m, 2H), 2.94 (s, 3H), 3.26 (m, 2H), 4.46 (d, 2H), 7.08 (d, 1H), 7.20 (s, 1H), 7.46 (m, 1H), 7.64 (dd, 1H), 7.96 (s, 2H), 8.24 (s, 1H), 8.66 (t, 1H), 10.08 (s, 1H), 11.16 (s, 1H) ppm.

F. Alternatively, a mixture of 5-aminosulfonylindolin-2-one (1.0 g, 4.7 mmol), 2-ethoxycarbonylcarbonylpyrrole (2.5 g, 14.5 mmol) in ethanol (120 mL) was treated with triethylamine (1.0 mL, 7.2 mmol). The reaction mixture was refluxed for 24 hours. The reaction mixture was concentrated to approximately 20 mL, treated with additional triethylamine (0.2 mL, 1.44 mmol) and refluxed for 55 hoursr. The reaction was then cooled to ambient temperature and concentrated. Reverse phase HPLC using acetonitrile/water afforded 5-aminosulfonyl-3-[(pyrrol-2-yl)(ethoxycarbonyl)methylene]indolin-2-one; $^1$H NMR (400 MHz, DMSO-$d_6$) δ 1.35 (t, 3H), 4.50 (q, 2H), 6.40 (s, 1H), 6.65 (s, 1H), 7.06 (d, 1H), 7.25(s, 2H), 7.48 (br s, 1H), 7.50 (s, 1H), 7.68 (d, 1H), 11.50 (s, 1H) ppm; (45 mg) and 5-aminosulfonyl-3-[(pyrrol-2-yl)(carboxy)methylene]indolin-2-one; $^1$H NMR (400 MHz, DMSO-$d_6$) δ 6.40 (s, 1H), 6.65 (s, 1H), 7.06 (d, 1H), 7.25 (s, 2H), 7.48 (br s, 1H), 7.68 (d, 1H), 7.85 (s, 1H), 11.50 (s, 1H) ppm; (48 mg).

G. In a similar manner, but replacing 2-ethoxycarbonylcarbonylpyrrole with the appropriately substituted (aminocarbonyl)carbonylpyrrole, which can be prepared by methods known to one of ordinary skill in the art or by the methods disclosed in Archibald, J. L. et al., *J. Med. Chem.* (1974), Vol. 17, pp. 736–739, the following compounds were made:

5-aminosulfonyl-3-[(pyrrol-2-yl)(aminocarbonyl)methylene]indolin-2-one; $^1$H NMR (400 MHz, DMSO-$d_6$) δ 6.40 (s, 1H), 6.75 (s, 1H), 7.00 (d, 1H), 7.20 (s, 2H), 7.44 (br s, 1H), 7.68 (d, 1H), 8.00 (br s, 2H), 8.25 (s, 1H), 11.20 (s, 1H) ppm; and 5-aminosulfonyl-3-[(pyrrol-2-yl)(N,N-diethylaminocarbonyl)methylene]-indolin-2-one; $^1$H NMR (400 MHz, DMSO-$d_6$) δ 0.78 (t, 3H), 1.30 (t, 3H), 3.15 (m, 2H), 3.36 (m, 1H), 3.85 (m, 1H), 6.40 (s, 1H), 6.58 (s, 1H), 7.02 (d, 1H), 7.20 (br s, 2H), 7.42 (s, 1H), 7.64 (s, 1H), 7.70 (d, 1H), 11.40 (s, 1H) ppm.

H. Alternatively, a mixture of 5-aminosulfonylindolin-2-one (0.22 g, 1.0 mmol), 2-(ethylamino)carbonylcarbonylpyrrole (0.33 g, 2.0 mmol) and piperidine (0.2 mL, 2.0 mmol) was irradiated in a microwave at 160° C. for 5 minutes. The reaction mixture was dissolved in dichloromethane (25 mL). The resulting mixture was washed with 0.2 N HCl (25 mL) and saturated sodium bicarbonate (25 mL), dried (magnesium sulfate) and concentrated. Chromatography on SiO$_2$ (10 g) using hexane/ethyl acetate afforded 5-aminosulfonyl-3-[(pyrrol-2-yl)(ethylaminocarbonyl)methylene]indolin-2-one; (45 mg), $^1$H NMR (400 MHz, DMSO-$d_6$) δ 1.16 (t, 3H), 3.36 (q, 2H), 6.40 (s, 1H), 6.64 (s, 1H), 7.02 (d, 1H), 7.20 (brs, 2H), 7.42 (s, 1H), 7.64 (d, 1H), 7.75 (s, 1H), 8.85 (t, 1H), 11.40 (s, 1H) ppm.

EXAMPLE 2

Compounds of Formula (Ib) and Formula (Ic)

A. To a suspension of 5-cyanoindolin-2-one (158 mg, 1 mmol) in ethanol (15 mL) was added 2-acetylpyrrole (95 mg, 1 mmol) and piperidine (0.1 mL). The reaction mixture was refluxed for 2 hours. A golden-colored product precipitated from the reaction mixture, which was filtered and washed with ethanol to afford 5-cyano-3-[1-(pyrrol-2-yl)ethylidene]indolin-2-one; (160 mg) $^1$H NMR (400 MHz, DMSO-$d_6$) δ 2.80 (s, 3H), 6.40. (m, 1H), 7.04 (d, 1H), 7.20 (m, 1H), 7.42 (m, 1H), 7.60 (dd, 1H), 8.04 (s, 1H), 11.40 (s, 1H) ppm.

B. A solution of 5-cyano-3-[1-(pyrrol-2-yl)ethylidene]indolin-2-one (100 mg, 0,42 mmol) in toluene was treated with tributyltin hydride (0.68 g, 2.1 mmol) and NaN$_3$ (0.39 g, 2.52 mmol). The reaction mixture was refluxed overnight. Concentration afforded a residue which was dissolved in methanol and left at ambient temperature overnight. An orange-colored solid formed, which was filtered and dried in vacuo to afford 5-tetrazol-5-yl-3-[(pyrrol-2-yl)methylene]indolin-2-one; (29 mg) as an orange solid; $^1$H NMR (400 MHz, DMSO-$d_6$) δ 6.22 (s, 1H), 6.90 (s, 1H), 7.08 (d, 1H), 7.20 (s, 1H), 7.80 (m, 1H), 7.84 (s, 1H), 8.14 (s, 1H), 11.22 (s, 1H) ppm.

C. In a similar manner as described above, but using the appropriately substituted starting material, the following compound of the invention was made:

5-cyano-3-[(pyrrol-2-yl)methylene]indolin-2-one; $^1$H NMR (400 MHz, DMSO-$d_6$) δ 6.40 (m, 1H), 6.88 (m, 1H), 7.06 (d, 1H), 7.48 (s, 1H), 7.66 (dd, 1H), 7.94 (s, 1H), 8.18 (s, 1H), 11.40 (s, 1H) ppm.

EXAMPLE 3

Compounds of Formula (Id) and Formula (Ie)

A. 5-Aminomethylindolin-2-one (160 mg, 1 mmol), 2-acetylpyrrole (190 mg, 1.74 mmol) and piperidine (0.4 mL) were mixed together in a microwave reaction vessel and heated to 160° C. for 8 minutes in a microwave reactor. The resulting black-colored solid was dissolved in DMSO and purified by reverse phase HPLC (acetonitrile/water) to afford 5-((1-pyrrol-2-yl)ethylidene)aminomethyl-3-[1-(pyrrol-2-yl)ethylidene]indolin-2-one; (20 mg), as a trifluoroacetate salt; $^1$H NMR (400 MHz, DMSO) δ 2.74 (s, 3H) 2.76 (s, 3H), 4.90 (d, 2H), 6.34 (m, 1H), 6.50 (m, 1H), 6.92 (d, 1H), 7.08 (m, 1H), 7.24 (d, 1H), 7.42 (s, 1H), 7.60 (m, 2H), 7.78 (s, 1H), 11.20 (s, 1H), 11.28 (brs, 1H) ppm.

B. Alternatively, a solution of 5-aminomethylindolin-2-one acetate salt (220 mg, 1 mmol) in ethanol (10 mL) was treated with diisopropylethylamine (DIEA) (3 mL). After 20 minutes, 2-pyrrolecarboxaldehyde (95 mg, 1 mmol) and pyrrolidine (0.05 mL) were added and the reaction mixture was stirred at 60° C. for 3 hours. Concentration of the solvent gave an oil which was purified by reverse phase HPLC (acetonitrile/water) to afford 5-aminomethyl-3-[(pyrrol-2-yl)methylene]indolin-2-one; as a trifluoroacetate salt (70 mg); $^1$H NMR (400 MHz, DMSO-d$_6$) δ 3.98 (m, 2H), 6.36 (m, 1H), 6.84 (brs, 1H), 6.88 (d, 1H), 7.22 (d, 1H), 7.34 (s, 1H), 7.62 (s, 1H), 7.68 (s, 1H), 8.20 (brs, 2H), 11.00 (s, 1H) ppm.

C. In a similar manner as described above in Paragraphs A and B, but using the appropriately substituted starting material, the following compounds of the invention were made:

5-aminomethyl-3-[1-(pyrrol-2-yl)ethylidene]indolin-2-one; $^1$H NMR (400 MHz, DMSO-d$_6$) δ 2.80 (s, 3H), 4.06 (m, 2H), 6.38 (m, 1H), 6.92 (d, 1H), 7.16 (m, 1H), 7.24 (d, 1H), 7.36 (m, 1H), 7.82 (s, 1H), 8.08 (brs, 2H), 11.08 (s, 1H) ppm;

4-(pyrrol-2-yl)methyleneamino-3-[(pyrrol-2-yl)methylene]indolin-2-one; $^1$H NMR (400 MHz, DMSO-d$_6$) δ 6.2 (m, 1H), 6.3 (m, 1H), 6.7 (m, 2H), 6.78 (m, 1H), 6.8 (dd, 1H), 7.0 (m, 1H), 7.3 (m, 1H), 7.58 (d, 1H), 7.62 (s, 1H), 8.3 (s, 1H), 10.9 (s, 1H), 11.7 (m, 2H) ppm.

EXAMPLE 4

Compounds of Formula (If)

A. To a suspension of 5-nitro-3-[(4-(dimethylethoxycarbonylaminomethyl)-pyrrol-2-yl)methylene]indolin-2-one (0.8 g, 2 mmol) in ethyl acetate/pyridine (60 mL/9 mL) was added tin (II) chloride dihydrate and the reaction mixture was refluxed for 1.5 hours. The reaction mixture was cooled to ambient temperature, filtered through celite and the filtrate was partitioned in water and ethyl acetate. The organic layer was washed with water and filtered again through celite. The organic layer was then washed with brine, and concentrated to afford 5-amino-3-[(4-(dimethylethoxycarbonylaminomethyl)pyrrol-2-yl)methylene]indolin-2-one as a red colored solid (0.68 g); $^1$H NMR (400 MHz, DMSO) δ 1.38 (s, 9H), 2.62 (s, 3H), 4.0 (d, 2H), 4.64 (s, 2H), 6.42 (d, 1H), 6.58 (d, 1H), 6.82 (s, 1H), 7.0 (s, 1H), 8.08 (m, 2H), 10.52 (s, 1H) ppm. Hydrolysis under standard conditions yielded 5-amino-3-[(4-(aminomethyl)pyrrol-2-yl)methylene]indolin-2-one; $^1$H NMR (400 MHz, DMSO-d$_6$) δ 2.66 (s, 3H), 4.00 (m, 2H), 6.50. (dd, 1H), 6.64 (d, 1H), 7.08 (s, 1H), 7.26 (s, 1H), 7.38 (s, 1H), 8.06 (brs, 1H), 10.18 (s, 1H) ppm.

B. In a similar manner as described above, but using the appropriately substituted starting material, the following compounds of formula (If) were prepared:

6-amino-3-[(pyrrol-2-yl)methylene]indolin-2-one; $^1$H NMR (400 MHz, DMSO-d$_6$) δ 6.30 (m, 1H), 6.84 (m, 3H), 7.34 (m, 1H), 7.68 (m, 1H), 7.78 (s, 1H), 11.04 (s, 1H) ppm;

4-amino-3-[(pyrrol-2-yl)methylene]indolin-2-one; $^1$H NMR (400 MHz, DMSO-d$_6$) δ 5.30 (s, 2H), 6.15 (d, 1H), 6.15 (dd, 1H), 6.25 (m, 1H), 6.60 (m, 1H), 7.15 (m, 1H), 7.20 (d, 1H), 7.25 (s, 1H), 10.6 (s, 1H) ppm;

5-amino-3-[1-(pyrrol-2-yl)ethylidene]indolin-2-one; $^1$H NMR (400 MHz, DMSO-d$_6$) δ 2.68 (s, 3H), 4.70 (s, 2H), 6.30 (m, 1H), 6.42 (m, 1H), 6.60 (m, 1H), 6.98 (m, 1H), 7.04 (m, 1H), 7.28 (m, 1H), 10.60 (s, 1H) ppm;

5-amino-3-[(pyrrol-2-yl)methylene]indolin-2-one; $^1$H NMR (400 MHz, DMSO-d$_6$) δ 6.38 (m, 1H), 6.90 (m, 2H), 7.06 (m, 1H), 7.36 (m, 1H), 7.44 (m, 1H), 7.78 (m, 1H), 11.02 (s, 1H) ppm;

5-amino-3-[1-(4-(2-aminoethylcarbamylmethyl)pyrrol-2-yl)ethylidene]indolin-2-one; $^1$H NMR (400 MHz, DMSO-d$_6$) δ 2.52 (m, 2H), 2.72 (s, 3H), 3.00 (m, 2H), 4.18 (d, 2H), 6.92 (d, 1H), 7.00 (s, 2H), 7.28 (s, 1H), 7.59 (s, 1H), 7.6 (s, 2H), 8.42 (t, 1H), 11.06 (s, 1H) ppm; and 5-amino-3-[(pyrrol-2-yl)(3-(5,5-dimethyl-1,3-dioxan-2-yl)prop-1-yl)methylene]indolin-2-one; $^1$H NMR (400 MHz, DMSO-d$_6$) δ 0.82 (s, 3H), 1.22 (s, 3H), 1.90 (m, 2H), 2.03 (m, 2H), 3.30 (m, 2H), 3.70 (d, 2H), 4.70 (t, 1H), 6.58 (m, 1H), 7.13 (d, 1H), 7.22–7.28 (m, 2H), 7.54 (m, 2H), 11.38 (s, 1H) ppm.

EXAMPLE 5

Compounds of Formula (Ig)

A. To a solution 5-ureidoindolin-2-one (326 mg, 1.71 mmol) in ethanol was added 4-bromo-2-pyrrolecarboxaldehyde (297 mg, 1.71 mmol), and piperidine (0.2 mL). The reaction mixture was refluxed for 18 hours. The mixture was cooled and filtered to afford a golden-colored solid which was washed with ethanol and ether to afford 5-ureido-3-[(4-bromopyrrol-2-yl)methylene]indolin-2-one; (453 mg); $^1$H NMR (400 MHz, DMSO-d$_6$) δ 5.77 (s, 2H); 6.74–6.76 (d, 1H); 6.96 (s, 1H); 7.02–7.04 (dd, 1H); 7.41–7.42 (m, 1H); 7.52–7.53 (m, 1H); 7.73–7.74 (d, 1H); 8.34 (s, 1H); 10.82 (bd, 1H); 13.5 (bs, 1H) ppm.

B. Alternatively, to a solution of 5-amino-3-[(4-(aminomethyl)pyrrol-2-yl)methylene]indolin-2-one; (178 mg, 0.46 mmol) in THF (30 mL) was added trimethylsilylisocyanate (0.3 mL, 2.90 mmol) and the reaction mixture was stirred at ambient temperature for 18 hours. The precipitate was filtered and washed with THF to afford a tan colored compound, 5-ureido-3-[1-(4-(1,1-dimethylethoxycarbonylaminomethyl)pyrrol-2-yl)ethylidene]indolin-2-one; (130 mg, 68%); $^1$H NMR (400 MHz, DMSO-d$_6$) δ 1.98 (s, 9H), 2.64 (s, 3H), 4.04 (d, 2H), 5.70 (brs, 2H), 6.76 (d, 1H), 6.92 (s, 1H), 7.16 (m, 2H), 7.78 (s, 1H), 8.38 (s, 1H), 10.80 (s, 1H) ppm.

C. In a similar manner as described above in either Paragraph A or Paragraph B, but using the appropriately substituted starting material, the following compounds of formula (Ig) were prepared:

5-ureido-3-[(4-(2-(imidazol-4-yl)ethyl)aminocarbonylpyrrol-2-yl)methylene]indolin-2-one; $^1$H NMR (400 MHz, DMSO-d$_6$) δ 2.85 (t, 2H), 3.48 (m, 2H), 5.78 (s, 2H), 6.75 (d, 1H), 7.04 (d, 1H), 7.17 (s, 1H), 7.44 (s, 1H), 7.53 (s, 1H), 7.70 (m, 2H), 8.21 (t, 1H), 8.36 (s, 1H), 8.95 (s, 1H) ppm;

5-ureido-3-[(4-(2-(pyridin-4-yl)ethyl)aminocarbonylpyrrol-2-yl)methylene]indolin-2-one; $^1$H NMR (400 MHz, DMSO-d$_6$) δ 3.05 (t, 2H), 3.48 (m, 2H), 5.78 (s, 2H), 6.74 (d, 1H), 7.04 (d, 1H), 7.15 (s, 1H), 7.54 (s, 1H), 7.70 (m, 2H), 7.76 (d, 2H), 8.19 (t, 1H), 8.33 (s, 1H), 8.72 (d, 2H) ppm;

5-ureido-3-[(4-((3R)-3-(dimethylamino)pyrrolidin-1-yl)carbonylpyrrol-2-yl)methylene]indolin-2-one; $^1$H NMR (400 MHz, DMSO-d$_6$) δ 2.10 (m, 1H), 2.25 (m, 1H), 2.83 (d, 6H), 3.41–4.20 (m, 5H), 6.74 (d, 1H), 6.96 (d, 1H), 7.24 (s, 1H), 7.58 (s, 1H), 7.78 (m, 2H), 8.38 (m, 2H), 9.82 (s, 1H), 10.82 (s, 1), 5-ureido-3-[(4-((3S)-3-(dimethylamino)pyrrolidin-1-yl)carbonylpyrrol-2-yl)methylene]indolin-2-one; $^1$H NMR (400 MHz, DMSO-d$_6$) δ 2.10 (m, 1H), 2.26 (m, 1H), 2.83 (d, 6H), 3.41–4.20 (m, 5H), 5.78 (s, 2H), 6.74 (d, 1H), 6.95 (d, 1H), 7.24 (s, 1H), 7.58 (s, 1H), 7.78 (m, 2H), 8.38 (m, 2H), 9.98 (s, 1H), 10.82 (s, 1H) ppm;

5-ureido-3-[(4-(3-(pyrrolidin-1-yl)propyl)aminocarbonylpyrrol-2-yl)methylene]indolin-2-one; $^1$H NMR (400 MHz, DMSO-d$_6$) δ 1.83 (m, 4H), 1.97 (m, 2H), 2.87 (m, 2H), 3.14 (m, 2H), 3.25 (m, 2H), 3.52 (m, 2H), 5.78 (s, 2H), 6.74 (d, 1H), 7.04 (d, 1H), 7.18 (s, 1H), 7.55 (s, 1H), 7.74 (m, 2H), 8.24 (t, 1H), 8.35 (s, 1H), 9.47 (s, 1H), 10.81 (s, 1H) ppm;

5-ureido-3-[(4-(4-(pyrrolidin-1-yl)butyl)aminocarbonylpyrrol-2-yl)methylene]indolin-2-one; $^1$H NMR (400 MHz, DMSO-d$_6$) δ 1.52 (m, 2H), 1.63 (m, 2H), 1.82 (m, 2H), 1.97 (m, 2H), 2.96 (m, 2H), 3.14 (m, 2H), 3.25 (m, 2H), 3.48 (m, 2H), 5.78 (s, 2H), 6.74 (d, 1H), 7.04 (d, 1H), 7.18 (s, 1H), 7.54 (s, 1H), 7.74 (m, 2H), 8.14 (t, 1H), 8.35 (s, 1H), 9.47 (s, 1H), 10.80 (s, 1H) ppm;

5-ureido-3-[(4-(4-methylpiperazin-1-yl)carbonylpyrrol-2-yl)methylene]indolin-2-one; $^1$H NMR (400 MHz, DMSO-d$_6$) δ 2.81 (s, 3H), 3.04 (m, 2H), 3.28 (m, 2H), 3.43 (m, 2H), 4.43 (m, 2H), 6.74 (d, 1H), 6.97 (d, 1H), 7.11 (s, 1H), 7.56 (s, 1H), 7.65 (s, 1H), 7.78 (s, 1H), 8.40 (s, 1H), 9.98 (s, 1H), 10.81 (s, 1H) ppm;

5-ureido-3-[(4-(4-(4-methylpiperazin-1-yl)carbonylphenyl)pyrrol-2-yl)methylene]indolin-2-one; $^1$H NMR (400 MHz, DMSO-d$_6$) δ 2.81 (s, 3H), 3.08 (s, 4H), 3.40 (peak obscured by water, m, 4H), 5.77 (s, 1H), 6.75 (d, 1H), 7.00 (dd, 1H), 7.31 (d, 1H), 7.45 (d, 2H), 7.58 (s, 1H), 7.69 (d, 2H), 7.77 (s, 1H), 7.88 (m, 1H), 8.35 (s, 1H), 9.83 (bs, 1H), 10.78 (s, 1H) ppm;

5-ureido-3-[(4-(3-(2-dimethylaminoethyl)aminocarbonylphenyl)pyrrol-2-yl)methylene]indolin-2-one; $^1$H NMR (400 MHz, DMSO-d$_6$) δ 2.84 (sm, 6H), 3.26 (m 2H), 3.64 (m, 2H), 5.78 (brs, 2H), 6.76 (d, 1H), 7.02 (dd, 1H), 7.30 (s, 1H), 7.48 (t, 1H), 7.58 (s, 1H), 7.68 (d, 1H), 7.78 (m, 2H), 7.84 (s, 1H), 8.08 (s, 1H), 8.38 (s, 1H), 7.26 (s, 1), 8.76 (t, 1H), 9.30 (brs, 1H), 10.78 (s, 1H) ppm;

5-ureido-3-[(4-(3-(4-methylpiperazin-1-yl)carbonylphenyl)pyrrol-2-yl)methylene]indolin-2-one; $^1$H NMR (400 MHz, DMSO-d$_6$) δ 2.83 (bs, 4H); 3.10 (bs, 4H); 5.78 (s, 2H); 6.75–6.77 (d, 1H); 6.99–7.02 (dd, 1H); 7.25–7.27 (d, 1H); 7.30 (m, 1H); 7.45–7.49 (dd, 1H); 7.58 (s, 1H); 7.66 (m, 1H); 7.73–7.75 (d, 1H); 7.86–7.87 (m, 1H); 8.36 (s, 1H); 10.79 (s, 1H); 13.46 (s, 1H) ppm; same sample with few drops of D2O added to clarify: $^1$H NMR (400 MHz, DMSO-d$_6$ plus a few drops of D$_2$O) δ 2.78 (s, 3H), 3.10 (bs, 4H), 3.31 (bs, 4H), 6.77–6.79 (d, 1H), 6.99–7.01 (dd, 1H), 7.22–7.23 (d, 1H), 7.26 (s, 1H), 7.43–7.47 (t, 1H), 7.58 (s, 1H), 7.62 (s, 1H), 7.69 (d, 1H), 7.71–7.73 (d, 1H), 7.80 (s, 1H) ppm;

5-ureido-3-[(4-(2-carboxyethyl)-3,5-dimethylpyrrol-2-yl)methylene]indolin-2-one; $^1$H NMR (400 MHz, DMSO-d$_6$) δ 1.45 (m, 6H), 2.18 (t, 2H), 2.12 (s, 3H), 2.23 (s, 3H), 2.57 (t, 2H), 2.74 (m, 4H), 5.81 (s, 2H), 6.70 (d, 1H), 7.08 (d, 1H), 7.35 (s, 1H), 7.68 (s, 1H), 8.24(s, 1H) ppm;

5-ureido-3-[(4-(2-(4-methylpiperazin-1-yl)carbonylethyl)-3,5-dimethylpyrrol-2-yl)methylene]indolin-2-one; $^1$H NMR (400 MHz, DMSO-d$_6$) δ 2.21 (s, 3H), 2.27 (m, 3H), 2.48 (m, 2H), 2.61 (m, 2H), 2.74 (s, 3H), 2.85 (m, 3H), 3.18 (m, 1H), 3.37 (m, 2H), 3.97 (m, 1H), 4.43 (m, 1H), 6.70 (d, 1H), 6.98 (d, 1H), 7.38 (s, 1H), 7.63 (s, 1H), 8.26 (s, 1H), 9.84 (s, 1H), 10.58 (s, 1H) ppm;

5-ureido-3-[(4-4-((3R)-3-hydroxypyrrolidin-1-yl)carbonylphenyl)pyrrol-2-yl)methylene]indolin-2-one; $^1$H NMR (400 MHz, DMSO-d$_6$) δ 1.70–1.90 (m, 2H), 3.40–3.60 (m, 3H), 4.25 (d, 1H), 4.90 (br d, 1H), 5.75 (br s, 2H), 6.75 (d, 1H), 7.02 (d, 1H), 7.29 (br s, 1H), 7.50 (brs, 2H), 7.55 (s, 1H), 7.60–7.68 (m, 2H), 7.40 (s, 1H), 7.86 (s, 1H), 8.30 (s, 1H), 10.80 (s, 1H) ppm;

5-ureido-3-[(4-(3-((3R)-3-hydroxypyrrolidin-1-yl)carbonylphenyl)pyrrol-2-yl)methylene]indolin-2-one; $^1$H NMR (400 MHz, DMSO-d$_6$) δ 1.75–2.00 (bm, 2H), 3.20–3.23 (d, 1H), 3.49–3.61 (m, 2H), 4.23 (bs, 1H), 4.33(bs, 1H), 5.78 (s, 2H), 6.74–6.76 (d, 1H), 7.03–7.05 (dd, 1H), 7.28–7.31(m, 2H), 7.40–7.44 (t, 1H), 7.58 (s, 1H), 7.68–7.70 (m, 1H), 7.74 (s, 1H), 7.89 (s, 1H), 8.34 (s, 1H), 10.79 (s, 1H), 13.48 (s, 1H) ppm;

5-ureido-3-[(4-(2-carboxyethyl)-3-methylpyrrol-2-yl)methylene]indolin-2-one; $^1$H NMR (400 MHz, DMSO-d$_6$) δ 1.47 (m, 6H), 2.21 (s, 3H), 2.34 (t, 2H), 2.61 (t, 2H), 2.75 (m, 4H), 5.78 (s, 2H), 6.72 (d, 1H), 7.08 (d, 1H), 7.11 (s, 1H), 7.40 (s, 1H), 7.62 (s, 1H), 8.43 (s, 1H) ppm;

5-ureido-3-[(4-(2-(pyridin-3-ylmethyl)aminocarbonylethyl)-3-methylpyrrol-2-yl)methylene]indolin-2-one; $^1$H NMR (400 MHz, DMSO-d$_6$) δ 2.22 (s, 3H), 2.39 (t, 2H), 2.67 (t, 2H), 4.38 (d, 2H), 6.72 (d, 1H), 7.04 (d, 1H), 7.06 (s, 1H), 7.42 (s, 1H), 7.65 (s, 1H), 7.70 (t, 1), 7.97 (d, 1H), 8.26 (s, 1H), 8.50 (t, 1H), 8.65 (m, 2H), 10.68 (s, 1H) ppm;

5-ureido-3-[(4-(2-(pyridin-4-yl)aminocarbonylethyl)-3-methylpyrrol-2-yl)methylene]indolin-2-one; $^1$H NMR (400 MHz, DMSO-d$_6$) δ 2.24 (s, 3H), 2.75 (m, 4H), 6.71 (d, 1H), 7.03 (d, 1H), 7.14 (s, 1H), 7.42 (s, 1H), 7.65 (s, 1H), 8.02 (d, 2H), 8.28 (s, 1H), 8.50 (t, 1H), 8.65 (d, 2H), 10.65 (s, 1H), 11.33 (s, 1H) ppm;

5-ureido-3-[(4-(2-(2-piperidin-1-ylethyl)aminocarbonylethyl)-3-methylpyrrol-2-yl)methylene]indolin-2-one; $^1$H NMR (400 MHz, DMSO-d$_6$) δ 1.31 (m, 1H), 1.60 (m, 3H), 1.74 (m, 2H), 2.22 (s, 3H), 2.34 (t, 2H), 2.64 (t, 2H), 2.83 (m, 2H), 3.03 (m, 2H), 3.39 (m, 4H), 6.72 (d, 1H), 7.03 (d, 1H), 7.08 (s, 1H), 7.41 (s, 1H), 7.65 (s, 1H), 8.14 (t, 1H), 8.28 (s, 1H), 10.64 (s, 1H) ppm;

5-ureido-3-[(4-(2-(4-methylpiperazin-1-yl)carbonylethyl)-3-methylpyrrol-2-yl)methylene]indolin-2-one; $^1$H NMR (400 MHz, DMSO-d$_6$) δ 2.22 (s, 3H), 2.61 (m, 4H), 2.76 (s, 3H), 3.88 (m, 3H), 3.25 (m, 1H), 3.38 (m, 2H), 4.05 (m, 1H), 4.43 (m, 1H), 6.72 (d, 1H), 7.04 (d, 1H), 7.13 (s, 1H), 7.42 (s, 1H), 7.65 (s, 1H), 8.28 (s, 1H), 10.63 (s, 1H) ppm;

5-ureido-3-[(4-(pyrimidin-5-yl)pyrrol-2-yl)methylene]indolin-2-one; $^1$H NMR (400 MHz, DMSO-d$_6$) δ 5.78 (s, 2H), 6.75–6.77 (d, 1H), 7.05–7.07 (dd, 1H), 7.40 (s, 1H), 7.59 (s, 1H), 7.76 (d, 1H), 7.99 (s, 1H), 8.34 (s, 1H), 9.00 (s, 1H), 9.08 (s, 2H), 10.82 (s, 1H), 13.34 (s, 1H) ppm;

5-ureido-3-[(4-(5-methoxypyridin-3-yl)pyrrol-2-yl)methylene]indolin-2-one; $^1$H NMR (400 MHz, DMSO-d$_6$) δ 3.88 (s, 3H), 5.78 (s, 2H), 6.75–6.77(d, 1H), 7.03–7.06 (dd, 1H), 7.36 (s, 1H), 7.55–7.58 (m, 2H), 7.75 (s, 1H), 7.93 (d, 1H), 8.18–8.12 (d, 1H), 8.34 (s, 1H), 8.48 (d, 1H), 10.78–10.79 (bd, 1H) ppm;

5-(ureido)methyl-3-[1-(pyrrol-2-yl)ethylidene]indolin-2-one; $^1$H NMR (400 MHz, DMSO-d$_6$) δ 2.78 (s, 3H), 4.18 (d, 2H), 5.50 (brs, 2H), 6.36 (m, 2H), 6.84 (d, 1H), 7.06 (m, 2H), 7.43 (m, 1H), 7.62 (s, 1H), 10.98 (s, 1H) ppm;

5-ureido-3-[1-(pyrrol-2-yl)propylidene]indolin-2-one; $^1$H NMR (400 MHz, DMSO) δ 1.42 (t, 3H), 3.25 (q, 2H), 5.82 (br s, 2H), 6.50 (m, 1H), 6.90 (d, 1H), 7.19 (s, 1H), 7.28 (d, 1H), 7.43 (s, 1H), 7.92 (s, 1H), 8.54 (s, 1H), 10.95 (s, 1H) ppm;

5-ureido-3-[(pyrrol-2-yl)(3-aminophenyl)methylene]indolin-2-one; $^1$H NMR (400 MHz, DMSO) δ 3.80 (br s, 3H), 5.30 (s, 1H), 5.65 (s, 1H), 5.75 (m, 1H), 6.20 (m, 1H), 6.68 (d, 1H), 7.05–7.15 (m, 3H), 7.35 (brs, 2H), 7.55 (t, 1H), 7.85 (s, 1H), 10.8 (s, 1H) ppm;

5-ureido-3-[(pyrrol-2-yl)(3-(1,1-dimethylethoxycarbonylamino)phenyl)-methylene]indolin-2-one; $^1$H NMR (400 MHz, DMSO-d$_6$) δ 1.40 (s, 9H), 5.36 (s, 1H), 5.60 (br s, 2H), 5.73 (m, 1H), 6.18 (m, 1H), 6.68 (d, 1H), 6.84 (d, 1H), 7.18 (dd, 1H), 7.32 (m, 2H), 7.39 (t, 1H), 7.52 (s, 1H), 7.62 (d, 1H), 9.50 (s, 1H), 10.8 (s, 1H) ppm;

5-ureido-3-[(pyrrol-2-yl)(3-aminoacetamidophenyl)-methylene]indolin-2-one; $^1$H NMR (400 MHz, DMSO-d$_6$) δ 3.70 (m, 2H), 5.48 (s, 1H), 5.75 (m, 1H), 6.20 (m, 1H), 6.68 (d, 1H), 7.02 (d, 1H), 7.07 (dd, 1H), 7.34 (s, 1H), 7.48–7.56 (m, 2H), 7.70 (d, 1H), 8.04 (br s, 3H) ppm;

5-ureido-3-[1-(pyrrol-2-yl)ethylidene]indolin-2-one; $^1$H NMR (400 MHz, DMSO-d$_6$) δ 2.72 (s, 3H), 5.70 (s, 2H), 6.34 (m, 1H), 6.76 (d, 1H), 7.04 (m, 1H), 7.20 (m, 1H), 7.30 (m, 1H), 7.76 (m, 1H), 8.40 (s, 1H), 10.82 (s, 1H) ppm;

5-(N'-ethylureido)-3-[1-(pyrrol-2-yl)ethylidene]indolin-2-one; $^1$H NMR (400 MHz, DMSO-d$_6$) δ 1.04 (t, 3H), 2.74 (s, 3H), 3.10 (m, 2H), 6.00 (t, 1H), 6.36 (m, 1H), 6.78 (d, 1H), 7.06 (s, 1H), 7.18 (m, 1H), 7.34 (m, 1H), 8.06 (m, 1H), 8.28 (s, 1H), 10.88 (s, 1H) ppm;

5-(N'-phenylureido)-3-[1-(pyrrol-2-yl)ethylidene]indolin-2-one; $^1$H NMR (400 MHz, DMSO-d$_6$) δ 2.76 (s, 3H), 6.38 (m, 1H), 6.84 (d, 1H), 6.94 (m, 1H), 7.08 (m, 1H), 7.22–7.30 (m, 3H), 7.34 (m, 1H), 7.46 (m, 2H), 7.90 (m, 1H), 8.60 (s, 1H), 8.64 (s, 1H), 10.90 (s, 1H) ppm;

5-(N-ethylureido)-3-[1-(pyrrol-2-yl)ethylidene]indolin-2-one; $^1$H NMR (400 MHz, DMSO-d$_6$) δ 1.02 (t, 3H), 2.76 (s, 3H), 3.58 (m, 2H), 5.44 (s, 2H), 6.36 (m, 1H), 6.90 (d, 1H), 7.00 (m, 1H), 7.10 (m, 1H), 7.36 (m, 1H), 7.48 (m, 1H), 11.10 (s, 1H) ppm;

5-ureido-3-[(pyrrol-2-yl)(pyridin-4-yl)methylene]indolin-2-one; $^1$H NMR (400 MHz, DMSO-d$_6$) δ 5.40 (s, 2H), 5.70 (m, 1H), 6.14 (m, 1H), 6.76 (d, 1H), 7.08 (m, 1H), 7.1–7.16 (m, 3H), 7.80 (m, 1H), 8.80 (m, 2H), 11.00 (s, 1H) ppm;

5-ureido-3-[(pyrrol-2-yl)(2-methoxypyridin-5-yl)methylene]indolin-2-one; $^1$H NMR (400 MHz, DMSO-d$_6$) δ 3.94 (s, 3H), 5.38 (s, 1H), 5.76 (m, 2H), 6.22 (m, 1H), 6.66 (d, 1H), 6.94 (d, 1H), 7.06 (m, 1H), 7.36 (m, 1H), 7.62 (d, 1H), 8.04 (s, 1H), 10.90 (s, 1H) ppm;

5-ureido-3-[(pyrrol-2-yl)methylene]indolin-2-one; $^1$H NMR (400 MHz, DMSO-d$_6$) δ 5.65 (brs, 2H), 6.32 (m, 1H), 6.72 (d, 1H), 6.85 (b, 1H), 6.92 (dd, 1H), 7.32 (s, 1H), 7.06 (s, 1H), 7.70 (s, 1H), 8.30 (s, 1H), 10.18 (s, 1H) ppm;

5-(N'-aminocarbonylureido)-3-[(pyrrol-2-yl)methylene]indolin-2-one; $^1$H NMR (400 MHz, DMSO-d$_6$) δ 6.38 (m, 1H), 6.78 (d, 1H), 6.85 (b, 1H), 7.18 (dd, 1H), 7.34 (s, 1H), 7.70 (s, 1H), 8.84 (s, 1H), 9.86 (s, 1H), 10.30 (s, 1H) ppm;

5-ureido-3-[(pyrrol-2-yl)(pyridin-3-yl)methylene]indolin-2-one; $^1$H NMR (400 MHz, DMSO-d$_6$) δ 5.4 (s, 1H), 5.6 (m, 3H), 6.2 (m, 1H), 6.7 (d, 1H), 7.1 (dd, 1H), 7.4 (m, 1H), 7.6 (m, 1H), 7.7 (s, 1H), 7.75 (m, 1H), 8.5 (s, 1H), 8.75 (m, 1H), 11 (s, 1H) ppm;

5-ureido-3-[(pyrrol-2-yl)(4-methoxyphenyl)methylene]indolin-2-one; $^1$H NMR (400 MHz, DMSO-d$_6$) δ 3.8 (s, 3H), 5.4 (m, 1H), 5.6 (m, 2H), 5.8 (m, 1H), 6.2 (m, 1H), 6.7 (d, 1H), 7.1 (d, 2H), 7.15 (m, 1H), 7.2 (d, 2H), 7.6 (m, 1H), 7.6 (s, 1H), 10.9 (s, 1H) ppm;

5-ureido-3-[1-(4-(aminomethyl)pyrrol-2-yl)ethylidene]indolin-2-one; $^1$H NMR (400 MHz, DMSO-d$_6$) δ 2.68 (s, 3H), 3.98 (d, 2H), 5.78 (brs, 2H), 6.80 (d, 1H), 7.04 (s, 1H), 7.20 (d, 1H), 7.40 (s, 1H), 7.44 (s, 1H), 8.02 (brs, 2H), 8.26 (s, 1H), 10.88 (s, 1H) ppm;

5-ureido-3-[1-(4-(acetamidomethyl)pyrrol-2-yl)ethylidene]indolin-2-one; $^1$H NMR (400 MHz, DMSO-d$_6$) δ 1.80 (s, 3H), 2.68 (s, 3H), 4.18 (d, 2H), 5.74 (brs, 2H), 6.76 (d, 1H), 6.94 (s, 1H), 7.20 (m, 2H), 7.75 (s, 1H), 8.20 (t, 1H), 8.38 (s, 1H), 10.72 (s, 1H) ppm;

5-ureido-3-[1-(4-(((1,1-dimethylethoxycarbonylamino)methyl)-carbonylaminomethyl)pyrrol-2-yl)ethylidene]indolin-2-one; $^1$H NMR (400 MHz, DMSO-d$_6$) δ 1.40 (s, 9H), 2.66 (s, 3H), 3.54 (d, 2H), 4.20 (d, 2H), 5.68 (brs, 2H), 6.75 (d, 1H), 6.94 (s, 1H), 7.22 (m, 2H), 7.80 (s, 1H), 8.18 (t, 1H), 8.38 (s, 1H), 10.80 (s, 1H) ppm;

5-ureido-3-[1-(4-(aminoacetamido)methylpyrrol-2-yl)ethylidene]indolin-2-one; $^1$H NMR (400 MHz, DMSO-d$_6$) δ 2.84 (s, 3H), 3.74 (d, 2H), 4.22 (d, 2H), 5.88 (brs, 2H), 6.94 (d, 1H), 7.16 (s, 1H), 7.36 (d, 1H), 7.42 (s, 1H), 8.00 (s, 1H), 8.20 (brs, 2H), 8.62 (s, 1H), 8.82 (t, 1H), 10.96 (s, 1H) ppm;

5-ureido-3-[1-(4-(pyridin-4-ylcarbonylamino)methylpyrrol-2-yl)ethylidene]indolin-2-one; $^1$H NMR (400 MHz, DMSO-d$_6$) δ 2.70 (s, 3H), 3.74 (d, 2H), 4.40 (d, 2H), 5.68 (brs, 2H), 6.76 (d, 1H), 7.00 (s, 1H), 7.20 (d, 1H), 7.28 (s, 1H), 7.78 (m, 3H), 8.36 (s, 1H), 8.22 (d, 2H), 9.16 (t, 1H), 10.82 (s, 1H) ppm;

5-ureido-3-[1-(4-(hydroxyacetamido)methylpyrrol-2-yl)ethylidene]indolin-2-one; $^1$H NMR (400 MHz, DMSO-d$_6$) δ 2.66 (s, 3H), 3.82 (d, 2H), 4.24 (d, 2H), 5.44 (t, 1H), 5.72 (brs, 2H), 6.76 (d, 1H), 6.94 (s, 1H), 7.20 (m, 2H), 7.74 (s, 1H), 7.78 (t, 1H), 8.38 (s, 1H), 10.80 (s, 1H) ppm;

5-ureido-3-[1-(4-(1-(1,1-dimethylethoxycarbonyl)piperidin-4-ylcarbonylamino)methylpyrrol-2-yl)ethylidene]indolin-2-one; $^1$H NMR (400 MHz, DMSO-d$_6$) δ 1.38 (s, 9H), 1.20 (m, 2H), 1.62 (d, 2H), 2.28 (m, 1H), 2.46 (m, 1H), 2.64 (s, 3H), 2.68 (m, 1H), 3.88 (d, 2H), 4.18 (d, 2H), 5.68 (brs, 2H), 6.76 (d, 1H), 6.92 (s, 1H), 7.20 (m, 2H), 7.78 (s, 1H), 8.12 (t, 1H), 8.38 (s, 1H), 10.80 (s, 1H) ppm;

5-ureido-3-[1-(4-(piperidin-4-ylcarbonylamino)methylpyrrol-2-yl)ethylidene]indolin-2-one; $^1$H NMR (400 MHz, DMSO-d$_6$) δ 1.70 (m, 2H), 1.82 (d, 2H), 2.42 (m, 1H), 2.66 (s, 3H), 2.84 (m, 2H), 3.28 (m, 2H), 4.18 (d, 2H), 5.70 (brs, 2H), 6.76 (d, 1H), 6.92 (s, 1H), 7.24 (m, 2H), 7.80 (s, 1H), 8.24 (t, 1H), 8.38 (s, 1H), 10.32 (s, 1H) ppm;

5-ureido-3-[1-(4-((1,1-dimethylethoxycarbonyl)acetamido)-methylpyrrol-2-yl)ethylidene]indolin-2-one; $^1$H NMR (400 MHz, DMSO-d$_6$) δ 1.38 (s, 9H), 2.64 (s, 3H), 3.12 (s, 2H), 4.18 (d, 2H), 5.70 (brs, 2H), 6.76 (d, 1H), 6.96 (s, 1H), 7.20 (m, 2H), 7.76 (s, 1H), 8.30 (t, 1H), 8.40 (s, 1H), 10.32 (s, 1H) ppm;

5-ureido-3-[1-(4-(1-(1,1-dimethylethoxycarbonyl)pyrrolidin-2-ylcarbonylamino)methylpyrrol-2-yl)ethylidene]indolin-2-one; $^1$H NMR (400 MHz, DMSO-d$_6$) δ 1.24 (s, 9H), 1.80 (m, 3H), 2.08 (m, 1H), 2.66 (s, 3H), 3.40 (m, 2H), 4.18 (m, 3H), 5.64 (brs, 2H), 6.74 (d, 1H), 6.96 (d, 1H), 7.22 (m, 2H), 7.78 (s, 1H), 8.19 (t, 1H), 8.42 (s, 1H), 10.40 (s, 1H) ppm;

5-ureido-3-[1-(4-((2-(1,1-dimethylethoxycarbonylamino)ethyl)carbonylamino)methylpyrrol-2-yl)ethylidene]indolin-2-one; $^1$H NMR (400 MHz, DMSO-d$_6$) δ 1.38 (s, 9H), 2.22 (t, 2H), 2.64 (s, 3H), 3.16 (t, 2H), 4.18 (m, 3H), 5.70 (brs, 2H), 6.75 (d, 1H), 6.92 (s, 1H), 7.22 (m, 2H), 7.74 (s, 1H), 8.14 (t, 1H), 8.34 (s, 1H), 10.80 (s, 1H) ppm;

5-ureido-3-[1-(4-(carboxyacetamido)methylpyrrol-2-yl)ethylidene]indolin-2-one; $^1$H NMR (400 MHz, DMSO-d$_6$) δ 2.64 (s, 3H), 3.18 (s, 2H), 4.18 (d, 2H), 5.68 (brs, 2H), 6.54 (s, 1H), 6.74 (d, 1H), 6.98 (s, 1H), 7.18 (m, 2H), 7.78 (s, 1H), 8.34 (t, 1H), 8.40 (s, 1H), 10.82 (s, 1H) ppm;

5-ureido-3-[1-(4-(pyrrolidin-2-ylcarbonylamino)methylpyrrol-2-yl)ethylidene]indolin-2-one; $^1$H NMR (400 MHz, DMSO-d$_6$) δ 1.84 (m, 3H), 2.22 (m, 1H), 2.64 (s, 3H), 3.22 (m, 2H), 4.06 (brs, 1H), 4.35 (m, 2H), 5.72 (brs, 2H), 6.78 (d, 1H), 6.94 (d, 1H), 7.16 (d, 1H), 7.24 (s, 1H), 7.82 (s, 1H), 8.40 (s, 1H), 8.56 (brs, 1H), 8.88 (t, 1H), 9.24 (brs, 1H), 10.88 (s, 1H) ppm;

5-ureido-3-[1-(4-(pyridin-3-ylcarbonylamino)methylpyrrol-2-yl)ethylidene]indolin-2-one; $^1$H NMR (400 MHz, DMSO-d$_6$) δ 2.66 (s, 3H), 4.44 (d, 2H), 4.40 (d, 2H), 6.78

(d, 1H), 7.00 (s, 1H), 7.20 (d, 1H), 7.30 (s, 1H), 7.62 (m, 1H), 7.78 (s, 1H), 8.38 (dd, 1H), 8.40 (s, 1H), 8.74 (q, 1H), 9.22 (m, 2H), 10.82 (s, 1H) ppm;

5-ureido-3-[1-(4-((2-aminoethyl)carbonylamino)methylpyrrol-2-yl)ethylidene]indolin-2-one; ¹H NMR (400 MHz, DMSO-d₆) δ 2.44 (m, 2H), 2.54 (s, 3H), 3.00 (q, 2H), 4.20 (d, 2H), 5.72 (brs, 2H), 6.78 (d, 1H), 6.94 (s, 1H), 7.18 (dd, 1H), 7.22 (s, 1H), 7.70 (brs, 2H), 7.82(s, 1H), 8.42 (s, 1H), 10.86 (s, 1H) ppm;

5-ureido-3-[1-((4-((1,2-diaminoethyl)carbonylamino)methylpyrrol-2-yl)ethylidene]indolin-2-one; ¹H NMR (400 MHz, DMSO-d₆) δ 2.50 (s, 3H), 3.28 (m, 2H), 4.20 (d, 2H), 4.36 (dd, 1H), 6.68 (d, 1H), 6.74 (d, 1H), 7.00 (s, 1H), 7.18 (dd, 1H), 7.28 (s, 1H), 7.82 (s, 1H), 8.50 (brs, 4H), 8.70 (brs, 4H), 9.00 (t, 1H), 10.84 (s, 1H) ppm;

5-ureido-3-[1-(4-((1-amino-2-methoxycarbonylethyl)carbonylamino)-methylpyrrol-2-yl)ethylidene]indolin-2-one; ¹H NMR (400 MHz, DMSO-d₆) δ 2.70 (s, 3H), 2.78 (dq, 2H), 3.68 (s, 3H), 4.20 (br, 1H), 4.44 (dd, 1H), 5.76 (brs, 2H), 6.78 (d, 1H), 6.90 (s, 1H), 7.28 (dd, 1H), 7.46 (s, 1H), 7.84 (s, 1H), 8.36 (brs, 2H), 8.40 (s, 1H), 8.78 (t, 1H), 10.86 (s, 1H) ppm;

5-ureido-3-[1-(4-((3-amino-1-acetylaminoprop-1-yl)carbonylamino)methylpyrrol-2-yl)ethylidene]indolin-2-one; ¹H NMR (400 MHz, DMSO-d₆) δ 1.78 (m, 1H), 1.86 (s, 3H), 1.94 (m, 1H), 2.68 (s, 3H), 2.76 (m, 2H), 4.18 (d, 2H), 4.35 (q, 1H), 5.74 (brs, 2H), 6.76 (d, 1H), 6.88 (s, 1H), 7.18 (dd, 1H), 7.20 (s, 1H), 7.70 (brs, 2H), 7.82 (s, 1H), 8.20 (d, 1H), 8.36 (t, 1H), 8.42 (s, 1H), 10.86 (s, 1H) ppm;

5-ureido-3-[1-(4-(piperazin-2-ylcarbonylamino)methylpyrrol-2-yl)ethylidene]indolin-2-one; ¹H NMR (400 MHz, DMSO-d₆) δ 2.78 (s, 3H), 3.08 (m, 4H), 3.52 (m, 2H), 4.02 (m, 1H), 4.24 (dq, 2H), 5.74 (brs, 2H), 6.78 (d, 1H), 6.90 (s, 1H), 7.18 (d, 1H), 7.26 (s, 1H), 7.84 (s, 1H), 8.40 (s, 1H), 8.92 (brs, 1H), 10.84 (s, 1H) ppm;

5-ureido-3-[1-(4-(1-methylpiperidin-4-ylcarbonylamino)methylpyrrol-2-yl)ethylidene]indolin-2-one; ¹H NMR (400 MHz, DMSO-d₆) δ 1.76 (m, 2H), 1.90 (d, 2H), 2.36 (m, 1H), 2.68 (s, 3H), 2.74 (d, 3H), 2.90 (m, 2H), 3.40 (m, 2H), 4.20 (d, 2H), 5.72 (brs, 2H), 6.76 (d, 1H), 6.94 (s, 1H), 7.18 (d, 1H), 7.22 (s, 1H), 8.42 (s, 1H), 8.48 (t, 1H), 8.98 (brs, 1H), 10.82 (s, 1H) ppm;

5-ureido-3-[1-(4-(2-(piperidin-1-yl)ethylcarbonylamino)methylpyrrol-2-yl)ethylidene]indolin-2-one; ¹H NMR (400 MHz, DMSO-d₆) δ 1.64 (m, 4H), 1.86 (d, 2H), 2.38 (m, 1H), 2.68 (s, 3H), 2.74 (d, 3H), 2.90 (m, 2H), 3.44 (d, 2H), 4.18 (d, 2H), 5.72 (brs, 2H), 6.74 (d, 1H), 6.94 (s, 1H), 7.20 (m, 2H), 7.80 (s, 1H), 8.38 (t, 1H), 8.40 (m, 1H), 9.22 (brs, 1H), 10.80 (s, 1H) ppm;

5-ureido-3-[(4-(piperidin-1-ylmethyl)carbonylpyrrol-2-yl)methylene]indolin-2-one;
¹H NMR (400 MHz, DMSO-d₆) δ 1.38 (m, 2H); 1.51 (m, 4H); 2.41 (m, 4H); 3.46 (bs 2H); 5.77 (s, 2H); 6.74–6.76 (d, 1H); 7.05–7.07 (dd, 1H); 7.30 (s, 1H); 7.63(s, 1H); 7.73 (d, 1H); 8.10–8.11 (m, 1H); 8.34 (s, 1H); 10.83 (bs, 1H); 13.91 (bs, 1H) ppm;

5-ureido-3-[(4-((4-methylpiperazin-1-yl)methylcarbonyl)pyrrol-2-yl)methylene]indolin-2-one; ¹H NMR (400 MHz, DMSO-d₆) δ 2.14 (s, 3H); 2.32 (bs, 4H); 2.49 (bs, 4H); 3.52 (s, 2H); 5.77 (s, 1H); 6.74–6.76 (d, 1H); 6.96 (s, 1H); 7.02–7.04 (dd, 1H); 7.29 (d, 1H); 7.63 (s, 1H); 7.25–7.30 (d, 1H); 8.08–8.09 (m, 1H); 8.34 (s, 1H); 10.84 (bs, 1H); 12.12 (bs, 2H); 14.79 (bs, 1H) ppm;

5-ureido-3-[(4-(3-methoxyphenyl)pyrrol-2-yl)methylene]indolin-2-one; ¹H NMR (400 MHz, DMSO-d₆) δ 3.79 (s, 3H); 5.77 (s, 2H); 6.74–6.78 (m, 2H); 7.02–7.04 (dd, 1H); 7.15–7.20 (m, 2H); 7.26–7.30 (m, 2H); 7.57 (s, 1H); 7.74 (d, 1H); 7.82 (d, 1H); 8.33 (s, 1H); 10.76 (bs, 1H); 13.51 (bs, 1H) ppm;

5-ureido-3-[(4-(4-methoxyphenyl)pyrrol-2-yl)methylene]indolin-2-one; ¹H NMR (400 MHz, DMSO-d₆) δ 3.76 (s, 3H); 5.76 (s, 2H); 6.74–6.76 (s, 1H); 6.93–6.95 (ddd, 2H); 7.04 (dd, 1H); 7.18 (dd, 1H); 7.52–7.55 (ddd, 2H); 7.56 (s, 1H); 7.71–7.73 (m, 2H); 8.32 (s, 1H); 10.74 (bs, 1H); 13.55 (bs, 1H) ppm;

5-ureido-3-[(4-(3-hydroxyphenyl)pyrrol-2-yl)methylene]indolin-2-one; ¹H NMR (400 MHz, DMSO-d₆) δ 5.77 (s, 2H); 6.59–6.61 (dd, 2H); 6.74–6.76 (d, 1H); 6.98–7.04 (m, 4H); 7.13–7.18 (m, 2H); 7.59 (s, 1H); 7.73 (d, 1H); 8.33 (s, 1H); 9.36 (bs, 1H); 10.76 (bs, 1H); 13.53 (bs, 1H) ppm;

5-ureido-3-[(4-(3-acetylaminophenyl)pyrrol-2-yl)methylene]indolin-2-one; ¹H NMR (400 MHz, DMSO-d₆) δ 2.05 (s, 3H); 5.77 (s, 2H); 6.74–6.78 (d, 1H); 7.04–7.07 (dd, 1H); 7.18 (s, 1H); 7.27–7.28 (m, 2H); 7.41–7.44 (m, 1H); 7.64 (s, 1H); 7.71–7.72 (d, 2H); 7.79 (s, 1H); 8.33 (s, 1H); 9.95 (s, 1H); 10.76 (bs, 1H); 13.53 (bs, 1H) ppm;

5-ureido-3-[(4-(3-carboxyphenyl)pyrrol-2-yl)methylene]indolin-2-one; ¹H NMR (400 MHz, DMSO-d₆) δ 5.92 (s, 2H); 6.74–6.78 (d, 1H); 7.09–7.12 (dd, 1H); 7.28 (s, 1H); 7.34–7.38 (dd, 1H); 7.41–7.44 (m, 1H); 7.59 (s, 1H); 7.66–7.68 (d, 1H); 7.71–7.73 (d, 2H); 7.83 (s, 1H); 8.13 (s, 1H); 8.71 (s, 1H); 10.79 (bs, 1H); 13.5 (bs, 1H) ppm;

5-ureido-3-[(4-(pyridin-3-yl)pyrrol-2-yl)methylene]indolin-2-one; ¹H NMR (400 MHz, DMSO-d₆) δ 5.77 (s, 2H); 6.75–6.77 (d, 1H); 7.03–7.06 (dd, 1H); 7.33 (s, 1H); 7.34–7.40 (dd, 1H); 7.59 (s, 1H); 7.75–7.76 (d, 1H); 7.90–7.91 (d, 1H); 7.97–8.00 (dt, 1H); 8.33 (bs, 1H); 8.39–8.40 (dd, 1H); 8.87–8.89 (d, 1H); 10.77–10.79 (d, 1H); 13.42 (bs, 1H) ppm;

5-ureido-3-[(4-(3-(2-morpholin-4-ylethoxy)phenyl)pyrrol-2-yl)methylene]indolin-2-one; ¹H NMR (400 MHz, DMSO-d₆) δ 3.19 (bs, 4H); 3.64 (bs, 4H); 3.99 (bs, 3H); 4.19 (s, 2H); 4.78 (bs, 1H); 5.82 (bs, 2H); 6.59–6.62 (ddd, 1H); 6.98–6.99 (m, 1H); 7.02 (s, 1H); 7.04–7.05 (d, 1H); 7.07 (s, 1H); 7.12–7.14 (m, 2H); 7.25–7.30 (m, 1H); 7.69 (s, 1H); 7.77–7.78 (m, 1H); 7.82 (d, 1H); 8.46 (s, 1H); 9.38 (bs, 1H); 13.83 (bs, 1H) ppm;

5-ureido-3-[(4-(piperazin-1-ylmethylcarbonyl)pyrrol-2-yl)methylene]indolin-2-one; ¹H NMR (400 MHz, DMSO-d₆) δ 2.85–3.00 (bs, 4H); 3.35–3.45 (bs, 4H); 5.77 (bs, 2H); 6.75–6.77 (d, 1H); 7.01–7.04 (dd, 1H); 7.31 (s, 1H); 7.63 (s, 1H); 7.78 (s, 1H); 8.07–8.09 (dd, 1H); 8.40 (s, 1H); 8.62–8.74 (bs, 1H); 10.86 (s, 1H); 13.32 (bs, 1H) ppm;

5-ureido-3-[(4-(3-methoxycarbonylmethoxyphenyl)pyrrol-2-yl)methylene]indolin-2-one; ¹H NMR (400 MHz, DMSO-d₆) δ 3.64 (s, 3H); 4.65 (s, 2H); 5.75 (bs, 2H); 6.54–6.56 (dd, 1H); 6.69–6.71 (d, 1H); 6.88–6.71 (d, 1H); 6.94 (s, 1H); 6.97–6.99 (d, 1H); 7.01–7.04 (dd, 1H); 7.08–7.12 (dd, 1H); 7.22 (m, 1H); 7.67 (s, 1H); 7.70 (s, 1H); 7.76 (s, 1H); 8.35 (s, 1H); 9.32 (bs, 1H) ppm;

5-ureido-3-[(4-(4-methoxyarbonylphenyl)pyrrol-2-yl)methylene]indolin-2-one; ¹H NMR (400 MHz, DMSO-d₆) δ 3.84 (s, 3H); 5.78 (s, 2H); 6.75–6.77 (d, 1H); 7.04–7.06 (dd, 1H); 7.35 (s, 1H); 7.60 (s, 1H); 7.77–7.78 (d, 3H); 7.94–7.96 (d, 3H); 8.35 (s, 1H); 10.80 (bs, 1H); 13.41 (bs, 1H) ppm;

5-ureido-3-[(4-(3-aminocarbonylphenyl)pyrrol-2-yl)methylene]indolin-2-one; ¹H NMR (400 MHz, DMSO-d₆) δ 5.77 (s, 2H); 6.75–6.77 (d, 1H); 7.05–7.07 (dd, 1H); 7.31 (s, 1H); 7.39–7.46 (m, 2H); 7.60 (s, 1H); 7.67–7.69 (d, 1H); 7.73–7.76 (m, 2H); 7.86 (s, 1H); 8.03 (s, 1H); 8.11 (s, 1H); 8.33 (s, 1H); 10.78 (bs, 1H); 13.49 (bs, 1H) ppm;

5-ureido-3-[(4-(3,4-dimethoxyphenyl)pyrrol-2-yl)methylene]indolin-2-one; ¹H NMR (400 MHz, DMSO-d₆) δ 3.75

(s, 3H); 3.82 (s, 3H); 5.77 (s, 2H); 6.74–6.76 (d, 1H); 6.93–6.95 (d, 1H); 7.02–7.04 (dd, 1H); 7.12–7.14 (dd, 1H); 7.17–7.21 (dd, 1H); 7.56 (s, 1H); 7.73–7.75 (dd, 2H); 8.33 (s, 1H); 10.74 (bs, 1H); 13.55 (bs, 1H) ppm;

5-ureido-3-[(4-(4-carboxyphenyl)pyrrol-2-yl)methylene]indolin-2-one; $^1$H NMR (400 MHz, DMSO-$d_6$) δ 6.19 (bs, 2H); 6.71–6.73 (d, 1H); 7.26 (s, 1H); 7.43–7.45 (m, 2H); 7.59–7.63 (m, 3H); 7.83 (s, 1H); 7.93–7.95 (d, 2H); 9.74 (bs, 1H); 10.74 (bs, 1H); 13.55 (bs, 1H) ppm;

5-ureido-3-[(4-(3,4-dihydroxyphenyl)pyrrol-2-yl)methylene]indolin-2-one; $^1$H NMR (400 MHz, DMSO-$d_6$) δ 5.77 (s, 2H); 6.57 (s, 2H); 6.69–6.75 (m, 2H); 6.86–6.89 (dd, 1H); 6.97–7.12 (m, 2H); 7.56–7.60 (m, 1H); 7.71–7.73 (m, 2H); 8.32–8.33 (m, 1H); 8.74 (bs, 1H); 10.69–10.73 (bd, 1H); 13.60 (bs, 1H) ppm;

5-ureido-3-[(4-(4-(1,1-dimethylethoxycarbonylamino)methylphenyl)pyrrol-2-yl)methylene]indolin-2-one; $^1$H NMR (400 MHz, DMSO-$d_6$) δ 1.40 (s, 9H); 4.14–4.16 (d, 2H); 5.77 (bs, 2H); 6.74–6.76 (d, 1H); 7.04–7.07 (m, 2H); 7.22 (bs, 1H); 7.29–7.33 (dd, 1H); 7.39–7.42 (dd, 1H); 7.46–7.48 (m, 2H); 7.61 (s, 1H); 7.71–7.72 (d, 1H); 7.76–7.77 (dd, 1H); 8.33 (s, 1H); 10.76 (s, 1H); 13.51 (s, 1H) ppm;

5-ureido-3-[(4-(3-aminomethylphenyl)pyrrol-2-yl)methylene]indolin-2-one; $^1$H NMR (400 MHz, DMSO-$d_6$) δ 4.06 (s, 2H); 5.77 (bs, 2H); 6.75–6.77 (d, 1H); 7.01–7.04 (dd, 1H); 7.26–7.28 (m, 2H); 7.41–7.45 (dd, 1H); 7.60 (s, 1H); 7.62–7.64 (d, 1H); 7.72 (s, 1H); 7.76 (d, 1H); 7.79–7.80 (dd, 1H); 8.17 (bs, 2H); 8.36 (s, 1H); 10.76 (s, 1H); 13.46 (s, 1H) ppm;

5-ureido-3-[(4-(3-acetamidomethylphenyl)pyrrol-2-yl)methylene]indolin-2-one; $^1$H NMR (400 MHz, DMSO-$d_6$) δ 1.89 (s, 3H); 4.26–4.29 (d, 2H); 5.77 (bs, 2H); 6.74–6.76 (d, 1H); 7.03–7.06 (dd, 1H); 7.07–7.09 (d, 1H); 7.24 (m, 1H); 7.29–7.33 (dd, 1H); 7.49–7.50 (m, 2H); 7.61 (s, 1H); 7.73 (s, 1H); 7.78 (m, 1H); 8.33–8.37 (m, 2H); 10.76 (s, 1H); 13.51 (s, 1H) ppm;

5-ureido-3-[(4-(3-(1,1-dimethylethoxycarbonyl)aminomethylcarbonylaminomethyl-phenyl)pyrrol-2-yl)methylene]indolin-2-one; $^1$H NMR (400 MHz, DMSO-$d_6$) δ 1.40 (s, 9H); 3.58–3.60 (d, 2H); 4.30–4.32 (d, 2H); 5.77 (bs, 2H); 6.74–6.76 (d, 1H); 7.01–7.08 (m, 3H); 7.28–7.31 (m, 2H); 7.47–7.50 (m, 2H); 7.57 (s, 1H); 7.73–7.74 (d, 1H); 7.82 (bs, 1H); 8.30–8.33 (m, 2H); 10.76 (bs, 1H); 13.48 (bs, 1H) ppm;

5-ureido-3-[(4-(4-methylsulfonylphenyl)pyrrol-2-yl)methylene]indolin-2-one; $^1$H NMR (400 MHz, DMSO-$d_6$) δ 3.20 (s, 3H); 5.77 (bs, 2H); 6.75–6.77 (d, 1H); 7.04–7.06 (dd, 1H); 7.39 (s, 1H); 7.61 (s, 1H); 7.75–7.76 (d, 1H); 7.85–7.90 (m, 4H); 7.97 (m, 1H); 8.35 (s, 1H); 10.81 (bs, 1H); 13.39 (s, 1H) ppm;

5-ureido-3-[(4-(2-ethoxycarbonylethyl)carbonylpyrrol-2-yl)methylene]indolin-2-one; $^1$H NMR (400 MHz, DMSO-$d_6$) δ 1.18 (m, 3H), 2.59 (t, 2H), 3.08 (t, 2H), 4.04 (m, 2H), 5.77 (s, 1H), 6.76 (d, 1H), 7.06 (dd, 1H), 7.27 (s, 1H), 7.64 (s, 1H), 7.73 (s, 1H), 7.99 (m, 1H), 8.35 (s, 1H), 10.85 (s, 1H) ppm;

5-ureido-3-[(4-(2-carboxyethyl)carbonylpyrrol-2-yl)methylene]indolin-2-one; $^1$H NMR (400 MHz, DMSO-$d_6$) δ 2.5 (obscured by DMSO, t, 2H), 3.02 (t, 2H), 5.77 (s, 1H), 6.74 (d, 1H), 7.05 (dd, 1H), 7.25 (t, 1H), 7.62 (s, 1H), 7.71 (d, 1H), 7.98 (m, 1H), 8.34 (s, 1H), 10.84 (s, 1H) ppm;

5-ureido-3-[(4-(3-(2-piperidin-1-ylethyl)aminocarbonylphenyl)pyrrol-2-yl)methylene]indolin-2-one; $^1$H NMR (400 MHz, DMSO-$d_6$) δ 1.38 (m, 1H), 1.66 (m, 3H), 1.79 (d, 2H), 2.88 (m, 2H), 3.24 (m, 2H), 3.55 (d, 2H), 3.63 (m, 2H), 6.77 (d, 1H), 7.00 (m, 1H), 7.23 (s, 1H), 7.42 (t, 1H), 7.59 (s, 1H), 7.66 (d, 1H) 7.72 (d, 1H), 7.75 (d, 1H), 7.77 (m, 1H), 8.08 (t, 1H), 8.74 (t, 1H), 9.03 (s, 1H), 10.75 (s, 1H) ppm;

5-ureido-3-[(4-(ethoxycarbonylpyrrol-2-yl)methylene]indolin-2-one; $^1$H NMR (400 MHz, DMSO-$d_6$) δ 1.25 (t, 3H), 4.21 (q, 2H), 5.78 (s, 2H), 6.75 (d, 1H), 7.07 (d, 1H), 7.22 (s, 1H), 7.62 (s, 1H), 7.69 (s, 1H), 7.83 (s, 1H), 8.36 (s, 1H), 10.83 (s, 1H) ppm;

5-ureido-3-[(4-(carboxypyrrol-2-yl)methylene]indolin-2-one; $^1$H NMR (400 MHz, DMSO-$d_6$) δ 1.51 (m, 6H), 2.79 (m, 4H), 5.93 (s, 2H), 6.74 (d, 1H), 7.11 (s, 1H), 7.18 (d, 1H), 7.56 (s, 1H), 7.62 (s, 1H), 7.68 (s, 1H), 8.95 (s, 1H) ppm;

5-ureido-3-[(4-(2-morpholin-4-ylethyl)aminocarbonylpyrrol-2-yl)methylene]indolin-2-one; $^1$H NMR (400 MHz, DMSO-$d_6$) δ 3.16 (m, 2H), 3.27 (m, 2H), 3.51–3.69 (m, 6H), 3.96 (m, 2H), 6.64 (d, 1H), 7.03 (d, 1H), 7.20 (s, 1H), 7.57 (s, 1H), 7.72 (s, 1H), 7.76 (s, 1H), 8.38 (m, 2H), 9.82 (s, 1H) ppm;

5-ureido-3-[(4-(2-piperidin-1-ylethyl)aminocarbonylpyrrol-2-yl)methylene]indolin-2-one; $^1$H NMR (400 MHz, DMSO-$d_6$) δ 1.38 (m, 1H), 1.63 (m, 3H), 1.81 (m, 2H), 2.92 (m, 2H), 3.20 (m, 2H), 3.56 (m, 4H), 6.74 (d, 1H), 7.03 (d, 1H), 7.21 (s, 1H), 7.57 (s, 1H), 7.73 (s, 1H), 7.77 (s, 1H), 8.38 (m, 2H), 10.81 (s, 1H) ppm;

5-ureido-3-[(4-(pyridin-3-ylmethyl)aminocarbonylpyrrol-2-yl)methylene]indolin-2-one; $^1$H NMR (400 MHz, DMSO-$d_6$) δ 4.52 (d, 2H), 5.78 (s, 2H), 6.74 (d, 1H), 7.04 (d, 1H), 7.22 (s, 1H), 7.58 (s, 1H), 7.70 (s, 1H), 7.76 (m, 2H), 8.18 (d, 1H), 8.23 (s, 1H), 8.65–8.82 (m, 3H), 10.81 (s, 1H) ppm;

5-ureido-3-[(3-methyl-4-carboxypyrrol-2-yl)methylene]indolin-2-one; $^1$H NMR (400 MHz, DMSO-$d_6$) δ 1.51 (m, 6H), 2.58 (s, 3H), 2.78 (m, 4H), 5.93 (s, 2H), 6.72 (d, 1H), 7.19 (d, 1H), 7.44 (s, 1H), 7.60 (s, 1H), 7.65 (s, 1H), 8.73 (s, 1H) ppm;

5-ureido-3-[(4-(3-piperidin-1-ylpropyl)aminocarbonylpyrrol-2-yl)methylene]indolin-2-one; $^1$H NMR (400 MHz, DMSO-$d_6$) δ 1.37 (m, 1H), 1.61 (m, 3H), 1.75–1.90 (m, 4H), 2.85 (m, 2H), 3.06 (m, 2H), 3.26 (m, 2H), 3.40 (m, 2H), 6.74 (d, 1H), 7.03 (d, 1H), 7.18 (s, 1H), 7.56 (s, 1H), 7.73 (s, 1H), 7.77 (s, 1H), 8.24 (t, 1H), 8.38 (s, 1H), 10.81 (s, 1H) ppm;

5-ureido-3-[(4-(2-dimethylaminoethyl)aminocarbonylpyrrol-2-yl)methylene]indolin-2-one; $^1$H NMR (400 MHz, DMSO-$d_6$) δ 2.78 (s, 6H), 3.17 (m, 2H), 3.52 (m, 2H), 5.72 (s, 2H), 6.70 (d, 1H), 7.01 (d, 1H), 7.18 (s, 1H), 7.56 (s, 1H), 7.70 (s, 1H), 7.74 (s, 1H), 8.32 (m, 2H), 10.80 (s, 1H) ppm;

5-ureido-3-[(3-methyl-4-(2-piperidin-1-ylethyl)aminocarbonylpyrrol-2-yl)methylene]indolin-2-one; $^1$H NMR (400 MHz, DMSO-$d_6$) δ 1.38 (m, 1H), 1.63 (m, 3H), 1.81 (m, 2H), 2.52 (s, 3H), 2.92 (m, 2H), 3.18 (m, 2H), 3.55 (m, 4H), 6.76 (d, 1H), 7.07 (d, 1H), 7.49 (s, 1H), 7.72 (s, 1H), 7.75 (s, 1H), 8.18 (t, 1H), 8.34 (s, 1H), 10.80 (s, 1H) ppm;

5-ureido-3-[(4-phenylpyrrol-2-yl)methylene]indolin-2-one; $^1$H NMR (400 MHz, DMSO-$d_6$) δ 5.77 (s, 2H), 6.74–6.76 (dd, 1H), 7.02–7.05 (dd, 1H), 7.17–7.21 (dd, 1H), 7.26 (dd, 1H), 7.34–7.38 (dd, 2H), 7.56–7.62 (m, 3H), 7.74 (d, 1H), 7.81–7.82 (dd, 1H), 8.33 (s, 1H), 10.76 (s, 1H), 13.50 (bs, 1H) ppm;

5-ureido-3-[(4-(4-(2-piperidin-1-ylethyl)aminocarbonylphenyl)pyrrol-2-yl)methylene]indolin-2-one; $^1$H NMR (400 MHz, DMSO-$d_6$) δ 1.37 (m, 1H), 1.64 (m, 3H), 1.82 (d, 2H), 2.92 (m, 2H), 3.22 (m, 2H), 3.54 (d, 2H), 3.61 (m, 2H), 5.77 (s, 2H), 6.75 (d, 1H), 7.01 (dd, 1H), 7.33 (s, 1H), 7.57

(s, 1H), 7.72 (d, 2H), 7.76 (d, 1H), 7.86 (d, 2H), 7.91 (m, 1H), 8.35 (s, 1H), 8.66 (t, 1H), 9.00 (bs, 1H), 10.78 (s, 1H) ppm;

5-ureido-3-[(4-((morpholin-4-ylmethyl)carbonylaminomethyl)pyrrol-2-yl)methylene]indolin-2-one; $^1$H NMR (400 MHz, DMSO-d$_6$/TFA) δ 3.10–3.20 (m, 2H), 3.36 (m, 3H), 3.70–3.80 (m, 2H), 3.85 (m, 2H), 3.90 (s, 2H), 4.20 (d, 2H), 6.72 (d, 1H), 6.78 (s, 1H), 6.96 (d, 1H), 7.42 (s, 1H), 7.50 (s, 1H), 7.75 (s, 1H), 8.85 (t, 1H) ppm;

5-ureido-3-[(4-((piperidin-1-yl)acetamido)methylpyrrol-2-yl)methylene]indolin-2-one; $^1$H NMR (400 MHz, DMSO-d$_6$/TFA) δ 1.40 (m, 1H), 1.70–1.90 (m, 5H), 3.00 (m, 2H), 3.45 (d, 2H), 3.90 (s, 2H), 4.15 (d, 2H), 6.80 (d, 1H), 6.85 (s, 1H), 7.04 (d, 1H), 7.30 (s, 1H), 7.60 (s, 1H), 8.55 (br s, 1H), 8.90 (t, 1H), 9.64 (br s, 1H) ppm; and 5-ureido-3-[(4-(4-(2-dimethylaminoethyl)aminocarbonylphenyl)pyrrol-2-yl)methylene]indolin-2-one; $^1$H NMR (400 MHz, DMSO-d$_6$) δ 2.84 (d, 6H), 3.26 (t, 2H), 3.59 (q, 2H), 5.77 (s, 1H), 6.75 (d, 1H), 7.01 (dd, 1H), 7.33 (s, 1H), 7.57 (s, 1H), 7.72 (d, 2H), 7.76 (m, 1H), 7.86 (d, 2H), 7.90 (m, 1H), 8.35 (s, 1H), 8.63 (t, 1H), 9.27 (bs, 1H), 10.78 (s, 1H) ppm.

EXAMPLE 6

Compounds of Formula (Ih) and Formula (Ij)

A. A solution of 5-amino-3-[1-(pyrrol-2-yl)ethylidene]indolin-2-one (150 mg, 0.63 mmol) in dry tetrahydrofuran (15 mL) was treated with 2-bromoethyl isocyanate (105 mg, 0.63 mmol) at ambient temperature. The resulting reaction mixture was stirred at 45° C. for 2 hours. The reaction mixture was cooled to ambient temperature and concentrated. Chromatograpy on SiO$_2$ (5 g) using 2:1 hexane/ethyl acetate afforded a mixture of 5-(N'-(2-bromoethyl)ureido)-3-[1-(pyrrol-2-yl)ethylidene]indolin-2-one and 5-(4,5-dihydrooxazol-2-ylamino)-3-[1-(pyrrol-2-yl)ethylidene]indolin-2-one (120 mg).

B. A solution of 5-(N'-(2-bromoethyl)ureido)-3-[1-(pyrrol-2-yl)ethylidene]indolin-2-one and 5-(4,5-dihydrooxazol-2-ylamino)-3-[1-(pyrrol-2-yl)ethylidene]indolin-2-one (120 mg) and DMF (5 mL) was treated with triethylamine (61 mg, 0.6 mmol). After stirring overnight, the reaction was poured into water (25 mL) affording a solid which was isolated by filtration. Purification by reverse phase HPLC (acetonitrile/water) afforded 5-(4,5-dihydrooxazol-2-ylamino)-3-[1-(pyrrol-2-yl)ethylidene]indolin-2-one; (26 mg); $^1$H NMR (400 MHz, DMSO-d$_6$) δ 2.76 (s, 3H), 3.84 (t, 2H), 4.80 (t, 2H), 6.40 (m, 1H), 6.98 (m, 1H), 7.15 (m, 2H), 7.40 (m, 1H), 7.68 (m, 1H), 11.20 (s, 1H) ppm.

C. In a similar manner as described above, other compounds of formula (Ih) and formula (Ik) are prepared.

EXAMPLE 7

Compounds of Formula (Ii) and Formula (Ik)

A. A solution of 5-amino-3-[1-(pyrrol-2-yl)ethylidene]indolin-2-one (360 mg, 1.5 mmol) in tetrahydrofuran (15 mL) was treated with ethyl isocyanatoacetate (195 mg, 1.5 mmol) at ambient temperature. After stirring overnight, methanol (5 mL) was added and the reaction was concentrated. Chromatography on SiO$_2$ (7.2 g) using 1:2 hexane/ethyl acetate afforded 5-(N'-(ethoxycarbonylmethyl)ureido)-3-[1-(pyrrol-2-yl)ethylidene]indolin-2-one; $^1$H NMR (400 MHz, DMSO-d$_6$) δ 1.32 (t, 3H), 2.82 (s, 3H), 3.96 (d, 2H), 4.22 (q, 2H), 6.44 (m, 2H), 6.88 (d, 1H), 7.16 (m, 1H), 7.28 (d, 1H), 7.40 (m, 1H), 7.96 (m, 1H), 8.76 (s, 1H), 11.02 (s, 1H) ppm; (200 mg).

B. A solution of 5-(N'-(ethoxycarbonylmethyl)ureido)-3-[1-(pyrrol-2-yl)ethylidene]indolin-2-one (95 mg, 0.25 mmol) in tetrahydrofuran (2.5 mL) was treated with NaH (16 mg, 0.40 mmol). After stirring overnight, ethyl acetate (15 mL) and water (5 mL) were added and the reaction mixture was neutralized with 6N HCl. The organic layer dried (NaSO$_4$) and concentrated to afford a crude product (90 mg). Purification by reverse phase HPLC (acetonitrile/water) afforded 5-(2,4-dioxoimidazolidin-1-yl)-3-[1-(pyrrol-2-yl)ethylidene]indolin-2-one; (8 mg); $^1$H NMR (400 MHz, DMSO-d$_6$) δ 2.72 (s, 3H), 4.02 (s, 2H), 6.36 (m, 1H), 6.96 (d, 1H), 7.04 (m, 2H), 7.36 (d, 1H), 7.60 (m, 1H), 8.22 (s, 1H), 11.14 (s, 1H) ppm.

B. In a similar manner as described above, other compounds of formula (Ii) and formula (Ik) are prepared.

EXAMPLE 8

Compounds of Formula (IIa)

A. 4-Acetylimidazole (0.7 g, 3.1 mmol) and 5-nitroindolin-2-one (0.56 g, 3.1 mmol) in sealed tube were heated in the presence of piperidine at 135° C. After 30 minutes, the reaction mixture was cooled to ambient temperature and concentrated. Recrystallization from ethanol afforded 0.66 g of 5-nitro-3-[1-(imidazol-4-yl)ethylidene]indolin-2-one.

B. 5-nitro-3-[1-(imidazol-4-yl)ethylidene]indolin-2-one (0.55 g, 2 mmol) was suspended in ethyl acetate (50 mL) and tin chloride (4.6 g, 20 mmol) was added. The resulting reaction mixture was heated overnight to 70° C. The reaction mixture was then cooled to ambient temperature and sodium bicarbonate solution was added. Extraction with ethyl acetate afforded 0.4 g of 5-amino-3-[1-(imidazol-4-yl)ethylidene]indolin-2-one.

C. 5-amino-3-[(imidazol-4-yl)methylene]indolin-2-one (0.3 g, 1.3 mmol) was suspended in tetrahydrofuran (100 mL) and trimethylsilylisocyanate (0.5 mL, 3.75 mmol) was added. The reaction mixture was stirred at ambient temperature for three days. The reaction mixture was concentrated and dissolved in acetonitrile/water/TFA. Soluble solids were collected by filtration, dissolved in DMSO and purified with HPLC to afford 80 mg of 5-ureido-3-[1-(imidazol-4-yl)ethylidene]indolin-2-one; as an orange solid, $^1$H NMR (400 MHz, DMSO-d$_6$) δ 2.6 (s, 3H), 5.8 (s, 2H), 6.8 (d, 1H), 7.3 (m, 1H), 7.9 (s, 1H), 8.3 (s, 1H), 8.5 (s, 1H), 8.9 (s, 1H), 11.1 (s, 1H) ppm.

D. In a similar manner as described above in Paragraphs A–C, but using the appropriately substituted starting material, the following compounds of formula (IIa) were prepared:

5-hydroxy-3-[(imidazol-4-yl)methylene]indolin-2-one; $^1$H NMR (400 MHz, DMSO-d$_6$) δ 6.70 (s, 2H), 7.06 (s, 1H), 7.72 (s, 1H), 8.22 (s, 1H), 9.10 (s, 1H), 11.02 (s, 1H) ppm;

5-hydroxy-3-[(imidazol-2-yl)methylene]indolin-2-one; $^1$H NMR (400 MHz, DMSO-d$_6$) δ 6.76 (m, 2H), 7.10 (s, 1H), 7.60 (s, 1H), 7.88 (s, 2H), 11.22 (s, 1H) ppm;

3-[(imidazol-4-yl)methylene]indolin-2-one; $^1$H NMR (400 MHz, DMSO-d$_6$) δ 7.30 (d, 1H), 7.45 (t, 1H), 7.70 (t, 1H), 8.05 (d, 1H), 8.20 (s, 1H), 8.65 (s, 1H), 9.50 (s, 1H), 11.7 (s, 1H) ppm;

3-[(imidazol-2-yl)methylene]indolin-2-one; $^1$H NMR (400 MHz, DMSO-d$_6$) δ 7.00 (d, 1H), 7.10 (t, 1H), 7.40 (t, 1H), 7.80 (m, 2H), 7.90 (s, 2H), 11.6 (s, 1H) ppm;

6-fluoro-3-[(pyridin-2-yl)methylene]indolin-2-one; $^1$H NMR (500 MHz, DMSO-$d_6$) δ 6.68 (d, 1H), 6.79 (m, 1H), 7.47 (m, 1H), 7.55 (s, 1H), 7.86 (d, 1H), 7.95 (m, 1H), 8.88 (d, 1H), 9.11 (dd, 1H), 10.78 (s, 1H) ppm;

6-fluoro-3-[(pyridin-4-yl)methylene]indolin-2-one; $^1$H NMR (500 MHz, DMSO-$d_6$) δ 6.63–6.71 (m, 2H), 7.38 (m, 1H), 7.54 (s, 1H), 7.62 (d, 2H), 8.72 (d, 2H), 10.84 (s, 1H) ppm;

3-[(pyridin-4-yl)methylene]indolin-2-one; $^1$H NMR (500 MHz, DMSO-$d_6$) δ 6.81–6.90 (m, 2H), 7.25 (dd, 1H), 7.38 (d, 1H), 7.56 (s, 1H), 7.63 (d, 2H), 8.73 (d, 2H), 10.66 (s, 1H) ppm;

5-bromo-3-[(pyridin-4-yl)methylene]indolin-2-one; $^1$H NMR (500 MHz, DMSO-$d_6$) δ 6.78–6.88 (d, 2H), 7.38 (m, 1H), 7.43 (m, 1H), 7.62 (d, 2H), 8.75 (d, 2H), 10.82 (s, 1H) ppm;

3-[(pyridin-3-yl)methylene]indolin-2-one; $^1$H NMR (500 MHz, DMSO-$d_6$) δ 6.82–6.91 (m, 2H), 7.26 (dd, 1H), 7.38 (d, 1H), 7.57 (d, 1H), 7.62 (s, 1H), 8.11 (m, 1H), 8.67 (m, 1H), 8.88 (d, 1H), 10.63 (m, 1H) ppm;

6-fluoro-3-[(furan-2-yl)methylene]indolin-2-one; $^1$H NMR (500 MHz, DMSO-$d_6$) δ 6.69 (d, 1H), 6.78 (d, 1H), 6.82 (m, 1H), 7.27 (d, 1H), 7.32 (s, 1H), 8.14 (s, 1H), 8.38 (dd, 1H), 10.70 (m, 1H) ppm;

3-[(5-methylfuran-2-yl)methylene]indolin-2-one; $^1$H NMR (500 MHz, DMSO-$d_6$) δ 2.52 (s, 3H), 6.46 (d, 1H), 6.86 (d, 1H), 7.03 (dd, 1H), 7.18 (d, 1H), 7.20–7.27 (m, 2H), 8.30 (m, 1H), 10.47 (m, 1H) ppm;

3-[(5-(acetoxymethyl)furan-2-yl)methylene]indolin-2-one; $^1$H NMR (500 MHz, DMSO-$d_6$) δ 2.12 (s, 3H), 5.28 (s, 2H), 6.81 (d, 1H), 6.86 (dd, 1H), 7.00 (dd, 1H), 7.16–7.28 (m, 2H), 7.30 (s, 1H), 8.33 (m, 1H), 10.53 (m, 1H) ppm;

3-[(5-ethylfuran-2-yl)methylene]indolin-2-one; $^1$H NMR (400 MHz, $CDCL_3$) δ 8.45 (d, 1H), 8.05 (br, 1H), 7.4 (s, 1H), 7.25 (m, 1H), 7.05 (t, 1H), 6.85 (m, 2H), 6.25 (s, 1H), 2.85 (q, 2H), 1.4 (t, 3H) ppm;

3-[(3-methylthien-2-yl)methylene]indolin-2-one; $^1$H NMR (500 MHz, DMSO-$d_6$) δ 2.41 (s, 3H), 6.89 (d, 1H), 7.00 (dd, 1H), 7.18 (d, 1H), 7.27 (dd, 1H), 7.74 (s, 1H), 7.88 (d, 2H), 8.15 (d, 1H), 10.60 (m, 1H) ppm;

3-[(5-methylthien-2-yl)methylene]indolin-2-one; $^1$H NMR (500 MHz, DMSO-$d_6$) δ 2.55 (s, 3H), 6.83 (d, 1H), 6.93–7.00 (m, 2H), 7.18 (d, 1H), 7.64 (d, 1H), 7.72 (d, 1H), 7.98 (s, 1H), 10.52 (m, 1H) ppm;

3-[(4-bromothien-2-yl)methylene]indolin-2-one; $^1$H NMR (500 MHz, DMSO-$d_6$) δ 6.88 (d, 1H), 7.01 (dd, 1H), 7.23 (dd, 1H), 7.67 (d, 1H), 7.95 (m, 2H), 8.03 (s, 1H), 10.67 (m, 1H) ppm;

3-[(naphth-1-yl)methylene]indolin-2-one; $^1$H NMR (500 MHz, DMSO-$d_6$) δ 6.69 (dd, 1H), 6.88 (m, 2H), 7.17 (dd, 1H), 7.57–7.64 (m, 2H), 7.65 (d, 1H), 7.84 (d, 1H), 7.94 (d, 1H), 8.05 (m, 2H), 8.09 (s, 1H), 10.65 (m, 1H) ppm;

3-[(naphth-2-yl)methylene]indolin-2-one; $^1$H NMR (500 MHz, DMSO-$d_6$) δ 6.88 (m, 2H), 7.22 (m, 2H), 7.57–7.63 (m, 3H), 7.79 (s, 1H), 7.92–8.02 (m, 2H), 8.05 (d, 1H), 8.28 (s, 1H), 10.62 (m, 1H) ppm;

6-fluoro-3-[(indol-3-yl)methylene]indolin-2-one; $^1$H NMR (500 MHz, DMSO-$d_6$) δ 6.81 (m, 1H), 6.93 (m, 1H), 7.19–7.28 (m, 2H), 7.53 (m, 1H), 7.57 (d, 1H), 7.82 (m, 1H), 8.21 (m, 1H), 9.48 (s, 1H), 10.48 (m, 1H), 12.05 (m, 1H) ppm;

3-[(quinolin-4-yl)methylene]indolin-2-one; $^1$H NMR (500 MHz, DMSO-$d_6$) δ 6.65–6.72 (m, 2H), 6.88 (d, 1H), 7.21 (dd, 1H), 7.64 (dd, 1H), 7.73 (m, 1H), 7.84 (dd, 1H), 7.95 (d, 1H), 8.00 (s, 1H), 8.14 (d, 1H), 9.03 (m, 1H), 10.72 (m, 1H) ppm;

3-[(5-methylimidazol-4-yl)methylene]indolin-2-one; $^1$H NMR (400 MHz, DMSO-$d_6$) δ 2.50 (s, 3H), 6.90 (d, 1H), 7.00 (t, 1H), 7.20 (t, 1H), 7.80 (s, 1H), 7.95 (d, 1H), 8.00 (s, 1H), 11.0 (s, 1H) ppm;

3-[(1,3-dimethyl-5-chloropyrazol-4-yl)methylene]indolin-2-one; $^1$H NMR (400 MHz, DMSO-$d_6$) δ 2.10 (s, 3H), 3.80 (s, 3H), 6.90 (m, 2H), 7.00 (d, 1H), 7.40 (m, 2H), 10.6 (s, 1H) ppm; and 3-[(3-phenylpyrazol-4-yl)methylene]indolin-2-one; $^1$H NMR (400 MHz, DMSO-$d_6$) δ 6.80 (d, 1H), 6.95 (t, 1H), 7.20 (t, 1H), 7.40 (s, 1H), 7.50 (m, 1H), 7.55 (m, 2H), 7.60 (m, 2H), 7.80 (d, 1H), 8.40 (s, 1H), 10.5 (s, 1H) ppm.

EXAMPLE 9

This example illustrates the preparation of representative pharmaceutical compositions for oral administration containing a compound of the invention, or a pharmaceutically acceptable salt thereof:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 10

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 11

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 12

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 13

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 14

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 15

Cell-Based Assays

A. Materials

Prostate cancer cells (PC-3) and breast cancer cells (MDA468) were obtained from the ATCC (Manassas, Va.). Mammalian protein extraction reagent (MPER), Halt protease inhibitor cocktail, BCA protein reagent, and Supersignal Western Chemiluminescent reagent were obtained from Pierce Chemical Co. (Rockford, Ill.). 10% Tris-Glycine gels (1.0 mm, 15-well) and nitrocellulose (0.2 micron) were obtained from Invitrogen Life Technologies (Carlsbad, Calif.). Agar agar was purchased from EM Science. Polyclonal antibodies raised against phospho-AKT (Thr308, #9275), phospho-S6-kinase (Thr389, #9205), and anti-rabbit IgG-HRP conjugate were obtained from Cell Signaling Technologies (Beverly, Mass.). Nitroblue tetrazolium reagent and staurosporine were purchased from Sigma Chemical Co. (St. Louis, Mo.). LY294002 was purchased from Cayman Chemicals (Ann Arbor, Mich.). All other materials were of reagent-grade quality.

B. Cell Growth Conditions

PC-3 cells were grown in F12K medium, supplemented with 7% (v/v) fetal calf serum (fcs) and 2 mM glutamine. MDA-468 cells were grown in MEM-alpha, supplemented with 10% (v/v) fcs, 2 mM glutamine, 1 mM sodium pyruvate, 0.1 mM non-essential amino acids, 10 mM Hepes, and 1ug/ml insulin. All cell lines were incubated in a 37° C. humidified incubator, with a 5% $CO_2$ atmosphere.

C. Cell-Based Assays Using Western Blot Analysis

Treatment of cells with compounds blocked the activation of AKT and/or s6-kinase as reflected by the level of the phosphorylated active form of AKT (detected with the phospho-Thr-308-AKT antibody) or S6 kinase (detected by the phospho-Thr-389-S6-kinase antibody). To perform the assays, PC-3 cells were seeded into 24-well plates (Corning Costar) at 100–120,000 cells per well and allowed to grow overnight to 90% confluence. On the next day, the cells were washed once with 1.5 mL PBS, and the medium replaced with low serum (0.1% fcs) containing growth medium (starvation medium). After a second overnight incubation, the medium was replaced with 0.5 mL/well of starvation medium. Some assays were also conducted in normal growth medium (7% fcs, PC-3, or 10% fcs, MDA-468). Cells were treated with vehicle control (DMSO) or compound of the invention at a final DMSO concentration of 1% v/v (a 5 µl addition per 0.5 mL medium), and cells were allowed to incubate for the stated times. The incubations were terminated by aspiration of the medium, washing the wells with 1.0 mL PBS, and lysis in 0.1 mL MPER reagent, supplemented with protease inhibitors (Halt reagent) and phosphatase inhibitors (1 mM NaF, 1 mM sodium vanadate). Cell lysates were briefly centrifuged to remove insoluble debris, and aliquots were taken for protein (BCA) and Western blot analysis. For Western analysis, lysates were combined with Laemmli SDS sample buffer, boiled, and loaded onto 10% Tris-Glylcine gels, normalizing for the amount of protein loaded in each lane. Electrophoresed gels were transferred onto nitrocellulose paper, blocked with 5% milk in Tris-buffered saline containing 0.1% Tween-20, and incubated overnight with the primary antibody (phospho-AKT-Thr308 @ 1:667, phospho-S6 kinase @ 1:1000). Blots were washed three times with blocking buffer and incubated one hour with anti-rabbit IgG-HRP @ 1:2000. Washed blots were developed using the Supersignal Western Chemiluminescent detection system. Films were scanned using a Bio Rad CCD camera, and phospho-protein bands were quantitated using Bio Rad Quantity-One software.

D. Soft Agar Efficacy Assays

Treatment of PC-3 and MDA-468 cells plated in soft agar with compounds of the invention showed dose dependent inhibition in the growth of colonies (measured either as colony size and number). The duration of compound treatment of PC-3 and MDA-468 cells growing in soft agar was about 2 weeks. To perform the assay, culture plates (Corning 35 mm×10 mm) were prepared with a bottom layer of 0.5% agar in growth medium, 2 mlLwell. Cells were trypsinized, dispersed into single cells with a 21-gauge needle, and seeded in a top layer of 0.3% agar/growth medium, 1.5 mL/plate, containing 4500 cells per plate. On the following day, the first vehicle or compound treatment was added, in a volume of 1.0 mL of 0.3% agar/growth medium, containing 1% DMSO. Compound concentrations were adjusted to reflect the total volume of agar in the plates. The cells were allowed to grow for seven days and treated a second time (adding an additional 1 mL of 0.3% agar). Colonies were visually inspected for growth and viability every few days. On day 12–14, nitroblue tetrazolium (0.5 mg/mL PBS) was added, 0.3 mL per plate, and the viable colonies were allowed to develop color for 1–2 days. Plates were scanned using a Bio Rad CCD camera, and the colonies were quantitated for ony number, and for total stained area, using ImagePro software.

E. AKT2 and PDK-1 Expression and Purification pHisAKT2 was constructed by cloning AKT2 into pBlueBacHis2A (Invitrogen Corp.) through the BamH1 and Bgl2 restriction sites, forming a fusion protein behind a 38 amino acid N-terminal His tag sequence derived from the vector. The new N-terminal sequence+first 10 residues of AKT2 is as follows: MPRGSHHHHHHGMASMTG-GQQMGRDLYDDDDKDRWTGS<u>MNEVSVIKEG</u>(AKT2 is underlined and is in bold His-6). Similarly, pHisPDK-1 was constructed by cloning PDK1 into pBlueBacHis2A (Invitrogen Corp.) at EcoR1 cloning site, forming a fusion protein behind an N-terminal His-tag (preceding sequence of ... ICSWYHGIL<u>MARTTSQLYD</u> ... (PDK1 sequence underlined). The new N-terminal sequence+first 10 residues of PDK-1 is as follows: MPRGSHHHHHHGMASMTG-GQQMGRDLYDDDDKDRWGSELEICSWYHGILD <u>MARTTSQLYD</u> ... (PDK1 is underlined and His-6 is in bold).

Recombinant baculovirus containing either His-tagged AKT2 or His-tagged PDK-1 cDNAs were prepared by the following method. pHisAKT2 or pH is PDK-1 were cotransfected with Bac-N-Blue (Invitrogen) viral DNA info SF-21 cells and after 3–4 days, viral supernatant were isolated and recombinant viruses were plaque purified. His-tagged AKT2 (HisAKT-V) or His-tagged PDK-1 (H is PDK-1-V) cDNA expressing clones were selected and expanded as a stock for use in the expression of recombinant proteins described below.

To express His-tagged AKT2 and PDK-1, a 10 liter suspensions of SF-21 insect cells were infected with recombinant viruses (i.e., either H is PDK-1-V or HisAKT2-V) and cells were harvested 3–4 days post infection and frozen. To purify recombinant His-tagged AKT2 and PDK-1, cell pellets were thawed, homogenized (in phosphate buffered saline (PBS), supplemented with 10% Triton X-100, 0.5 M NaCl, 2 g/l NaF, 2.5 µg/mL aprotinin, 5 µg/mL leupeptin, 1.25 µg/mL pepstatin, 0.1% beta-mecaptoethanol, and 1 mM vanidate, 10 mM imidizole and adjusted to pH 7.6) and were purified using two sequential rounds of Ni2+ affinity chromatography followed by gel filtration. Enzymes were frozen in small aliquots and stored at −80° C. in 50 mM Tris-HCl, pH 7.5, 150 mM NaCl, pH 7.5, 0.1 mM EGTA, 0.1 mM EDTA, 0.2 µM benzamidine, 0.1% beta-mercaptoethanol and 0.25 M sucrose. Recombinant enzymes suitable for compound assays can also be purchased from Upstate Biotechnology (PDK-1, catalog #14-280; AKT2, catalog #14-422).

EXAMPLE 16

Enzyme Assays

A. PDK-1-Dependent Activation and Subsequent Enzymatic Activity of AKT2

Compounds were profiled an assay measuring PDK-1-dependent activation of AKT by modification of published procedures (e.g., Alessi, D. R., et al. "Characterization of a 3-phosphoinositide-dependent protein kinase which phosphorylates and activates protein kinase B," *Current Biology* (1997), Vol. 7, pp. 261–269).

Purified human AKT2 activity was routinely measured in an assay in which the enzyme was first activated by PDK-1 in the presence of phosphatidylinositol-4,5-bisphosphate (PIP$_2$). Once activated, AKT2-dependent phosphorylation of a peptide substrate was measured by scintillation proximity assay (SPA).

Phospholipid vesicles were prepared as follows: 2.2 mg each of phosphatidylcholine (Sigma Cat #P-1287) and phosphatidylserine (Sigma Cat #P-6641) were transferred to a borosilicate glass test tube and dried down under nitrogen.

1 mg of PIP$_2$ (Biomol Cat #PH-106) was suspended in 9.5 mL of 10 mM HEPES, pH 7.5 and transferred to the dried lipids. The tube was vortexed until a milky suspension was produced. Then the tube was placed in a ice water-jacketed cup horn sonicator (Branson Instruments) and subjected to sonication for 20 min at medium power until a translucent phospholipid vesicle preparation was obtained. Aliquots of the vesicle suspension were frozen at −80° C. until needed.

Assays were performed in 96-well polypropylene V-bottom plates. Incubations were carried out for 2 hr at room temperature. The assay mixture contained in a volume of 60 μL: 15 mM MOPS, pH 7.2, 1 mg/mL bovine serum albumin, 18 mM betaglycerolphosphate, 0.7 mM dithiothreitol, 3 mM EGTA, 10 mM MgOAc, 7.5 μM ATP, 0.2 μCi of [γ-$^{33}$P]ATP, 7.5 μM biotinylated peptide substrate (biotin-ARRRDGG-GAQPFRPRAATF), 0.5 μL of PIP$_2$-containing phospholipid vesicles, 60 μg of purified recombinant human PDK-1, and 172 ng of purified recombinant human AKT2. Test compounds were added from stock solutions in DMSO. The final DMSO concentration was 2.5%. Following incubation, 10 μL of the assay mixture was transferred to a 96-well clear-bottom polystyrene plate (Wallac Isoplate) containing 0.33 mg of streptavidin-coated SPA beads (Amersham Cat. #RPNQ0007) suspended in 200 μL of phosphate-buffered saline, pH 7.4, containing 50 mM EDTA and 0.1% Triton X-100. After brief shaking, the SPA beads were allowed to settle to the bottom of the plate overnight at room temperature. Product formation, measured in a Wallac MicroBeta scintillation counter, was proportional to the time of incubation and to the amount of PDK-1 and inactive AKT2 added. PDK-1 was added at sub-optimal levels so that the assay could sensitively detect inhibitors of AKT2 activation as well as direct AKT2 kinase inhibitors. The z'-factor for the assay was greater than 0.7.

Phosphorylation of the peptide substrate on the threonine residue was shown to be dependent upon activated AKT2 produced during the incubation. No phosphorylation was observed in the absence of ATP, Mg$^{2+}$, PDK-1, AKT2, or PIP$_2$-containing vesicles. Phosphorylation was readily observed, however, upon addition of purified activated human AKT1 (purchased from Upstate Biotechnology), independent of the presence or absence of added PDK-1 or PIP$_2$-containing vesicles.

B. Direct Assay of PDK-1 Activity

Recombinant human PDK-1 activity was directly measured using a filter binding protocol. Incubations were performed at room temperature for 4 hr in a final volume of 60 μL containing: 50 mM Tris-HCl, pH 7.5, 0.1 mM EGTA, 0.1 mM EDTA, 0.1% beta-mercaptoethanol, 1 mg/mL bovine serum albumin, 10 mM MgOAc, 10 μM ATP, 0.2 μCi of [γ-$^{33}$P]ATP, 7.5 μM of substrate peptide (H$_2$N-AR-RRGVTTKTFCGT) and 60 ng of purified human PDK-1. The enzymatic reaction was stopped by addition of 25 mM EDTA. A portion of the reaction mixture was spotted on Whatman P81 phosphocellulose paper. The filter paper was washed 3 times with 0.75% phosphoric acid to remove unreacted [γ-$^{33}$P]ATP, and once with acetone. After drying, the filter-bound labeled peptide was quantitated using a Fuji Phosphoimager.

Compounds of the invention can also be tested for their PDK-1 inhibitory activity by revising the methods disclosed in Biondi, R. M. et al., "Identification of a pocket in the PDK1 kinase domain that interacts with PIF and the C-terminal residues of PKA," *EMBO J.* (2000) Vol. 19(5), pp. 979–88, as needed.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of formula (I):

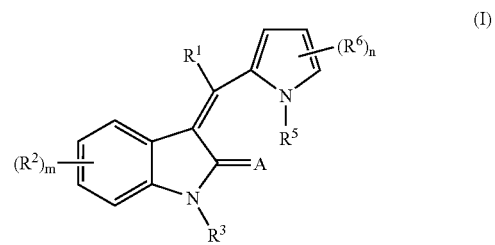

wherein:

m is 0 to 4;

n is 1 to 3;

A is oxygen;

R$^1$ is hydrogen, alkyl, —C(O)OR$^7$, or —C(O)N(R$^7$)$_2$; or

R$^1$ is aryl (optionally substituted by one or more substituents selected from the group consisting of alkyl, aryl, aralkyl, halo, haloalkyl, cyano, nitro, —R$^8$—OR$^7$, —R$^8$—N(R$^7$)$_2$, —R$^8$—C(O)OR$^7$, —R$^8$—C(O)N(R$^7$)$_2$, —R$^8$—N(R$^7$)C(O)N(R$^7$)$_2$, —R$^8$—N(R$^7$)C(O)—R$^9$—N(R$^7$)$_2$ and —R$^8$—N(R$^7$)C(O)OR$^7$); or R$^1$ is aralkyl (optionally substituted by one or more substituents selected from the group consisting of alkyl, aryl, aralkyl, halo, haloalkyl, cyano, nitro, —R$^8$—OR$^7$, —R$^8$—N(R$^7$)$_2$, —R$^8$—C(O)OR$^7$, —R$^8$—C(O)N(R$^7$)$_2$, —R$^8$—N(R$^7$)C(O)N(R$^7$)$_2$, —R$^8$—N(R$^7$)C(O)—R$^9$—N(R$^7$)$_2$ and —R$^8$—N(R$^7$)C(O)OR$^7$);

each R$^2$ is independently selected from the group consisting of alkyl, alkenyl, alkynyl, halo, haloalkyl, haloalkenyl, cyano, —R$^8$—OR$^7$, —R$^8$—N(R$^7$)$_2$, —R$^8$—C(O)OR$^7$, —R$^8$—C(O)N(R$^7$)$_2$, —R$^8$—N(R$^7$)S(O)$_t$R$^7$ (where t is 1 or 2), —R$^8$—N(R$^7$)S(O)$_t$N(R$^7$)$_2$ (where t is 1 or 2), —R$^8$—N(R$^7$)S(O)$_t$N(R$^7$)C(O)OR$^7$ (where t is 1 or 2), —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)—R$^9$—C(O)N(R$^7$)$_2$, —R$^8$—N(R$^7$)C(O)—R$^8$—N(R$^7$)—R$^8$—C(O)OR$^7$, —R$^8$—N(R$^7$)C(O)—R$^8$—N(R$^7$)—R$^8$—C(O)—R$^8$—N(R$^7$)$_2$, —N(R$^7$)C(=NR$^7$)N(R$^7$)$_2$, —C(=NR$^7$)—N(R$^7$)$_2$, —R$^8$—N=C(R$^7$)$_2$, heterocyclyl (optionally substituted by one or more substituents selected from the group consisting of alkyl, aryl, aralkyl, halo, haloalkyl, cyano, nitro, —R$^8$—OR$^7$, —R$^8$—C(O)OR$^7$, —R$^8$—C(O)N(R$^7$)$_2$, —R$^8$—N(R$^7$)$_2$, —R$^8$—N(R$^7$)C(O)—R$^8$—N(R$^7$)$_2$ and —R$^8$—N(R$^7$)C(O)OR$^7$), and optionally substituted cyclic ureido groups;

R$^3$ is hydrogen, alkyl or aralkyl;

R$^5$ is hydrogen, alkyl, aryl, aralkyl, —C(O)R$^{11}$ or —S(O)$_2$R$^{11}$;

each R$^6$ is optionally substituted phenyl;

each R$^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain;

each $R^9$ is a straight or branched alkylene chain; and each $R^{11}$ is optionally substituted alkyl, haloalkyl, optionally substituted aryl, optionally substituted aralkyl, optionally substituted heterocyclyl, or optionally substituted heterocyclylalkyl;

as a single stereoisomer, a mixture of stereoisomers, a solvate or a polymorph; or a pharmaceutically acceptable salt thereof;

with the following provisos:

(1) when m is 2, n is 1, A is oxygen, $R^1$, $R^3$ and $R^5$ are each hydrogen, $R^6$ is 3-methoxy, and one $R^2$ is 4-amino, the other $R^2$ can not be 5-amino; and (2) when m is 2, n is 1, A is oxygen, $R^1$, $R^3$ and $R^5$ are each hydrogen, and $R^6$ is 3-methoxy, and one $R^2$ is 5-nitro, the other $R^2$ can not be 4-fluoro or 4-azido.

2. The compound of claim 1 wherein:

m is 1 to 4;

n is 1 to 3;

A is oxygen;

$R^1$ is hydrogen or alkyl; or $R^1$ is aryl (optionally substituted by one or more substituents selected from the group consisting of —$R^8$—$OR^7$, —$R^8$—$N(R^7)_2$, —$R^8$—$C(O)N(R^7)_2$, —$R^8$—$N(R^7)C(O)N(R^7)_2$, —$R^8$—$N(R^7)C(O)$—$R^9$—$N(R^7)_2$ and —$R^8$—$N(R^7)C(O)OR^7$);

each $R^2$ is independently selected from the group consisting of heterocyclyl, —$R^8$—$N(R^7)_2$, —$R^8$—$N(R^7)S(O)_tN(R^7)_2$ (where t is 1 or 2), —$R^8$—$N(R^7)S(O)_tN(R^7)C(O)OR^7$ (where t is 1 or 2), —$R^8$—$N(R^7)C(O)R^7$, —$R^8$—$N(R^7)$—$R^8$—$C(O)OR^7$, —$R^8$—$N(R^7)C(O)N(R^7)_2$, —$R^8$—$N(R^7)C(O)$—$R^9$—$N(R^7)_2$, —$R^8$—$N(R^7)$—$R^9$—$C(O)N(R^7)_2$, —$R^8$—$N(R^7)C(O)$—$R^8$—$N(R^7)$—$R^8$—$C(O)OR^7$, —$R^8$—$N(R^7)C(O)$—$R^8$—$N(R^7)$—$R^8$—$C(O)$—$R^8$—$N(R^7)_2$, —$N(R^7)C(=NR^7)N(R^7)_2$, and —$R^8$—$N=C(R^7)_2$;

$R^3$ is hydrogen;

$R^5$ is hydrogen or alkyl;

each $R^6$ is phenyl (optionally substituted by one or more substituents selected from the group consisting of alkyl, —$R^8$—$OR^7$, —$R^8$—$O$—$R^8$—$C(O)R^7$, —$R^8$—$C(O)R^7$, —$R^8$—$C(O)OR^7$, —$R^8$—$C(O)N(R^7)_2$, —$R^8$—$N(R^7)C(O)R^7$, —$R^8$—$N(R^7)C(O)OR^7$, —$R^8$—$N(R^7)_2$, —$R^8$—$N(R^7)C(O)$—$R^8$—$N(R^7)$—$R^8$—$C(O)OR^7$, and —$R^8$—$S(O)_tR^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

3. The compound of claim 2 wherein:

m is 1;

n is 1 to 3;

A is oxygen;

$R^1$ is hydrogen or alkyl;

$R^2$ is —$R^8$—$N(R^7)C(O)R^7$, —$R^8$—$N(R^7)$—$R^8$—$C(O)OR^7$, —$R^8$—$N(R^7)C(O)N(R^7)_2$, —$R^8$—$N(R^7)$—$R^9$—$C(O)N(R^7)_2$, or —$R^8$—$N(R^7)C(O)$—$R^9$—$N(R^7)_2$;

$R^3$ is hydrogen;

$R^5$ is hydrogen or alkyl;

$R^6$ is phenyl (optionally substituted by one or more substituents selected from the group consisting of —$R^8$—$OR^7$, —$R^8$—$O$—$R^8$—$C(O)R^7$, —$R^8$—$C(O)R^7$, —$R^8$—$C(O)OR^7$, —$R^8$—$C(O)N(R^7)_2$, —$R^8$—$N(R^7)C(O)R^7$, —$R^8$—$N(R^7)C(O)OR^7$, —$R^8$—$N(R^7)_2$, —$R^8$—$N(R^7)C(O)$—$R^8$—$N(R^7)$—$R^8$—$C(O)OR^7$, and —$R^8$—$S(O)_tR^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

4. The compound of claim 2 wherein:

m is 1;

n is 1;

A is oxygen;

$R^1$ is hydrogen or alkyl;

$R^2$ is —$R^8$—$N(R^7)C(O)R^7$, —$R^8$—$N(R^7)$—$R^8$—$C(O)OR^7$, —$R^8$—$N(R^7)C(O)N(R^7)_2$, —$R^8$—$N(R^7)$—$R^9$—$C(O)N(R^7)_2$, or —$R^8$—$N(R^7)C(O)$—$R^9$—$N(R^7)_2$;

$R^3$ is hydrogen;

$R^5$ is hydrogen or alkyl;

$R^6$ is phenyl (optionally substituted by one or more substituents selected from the group consisting of —$R^8$—$OR^7$, —$R^8$—$O$—$R^8$—$C(O)R^7$, —$R^8$—$C(O)R^7$, —$R^8$—$C(O)OR^7$, —$R^8$—$C(O)N(R^7)_2$, —$R^8$—$N(R^7)C(O)R^7$, —$R^8$—$N(R^7)C(O)OR^7$, —$R^8$—$N(R^7)_2$, —$R^8$—$N(R^7)C(O)$—$R^8$—$N(R^7)$—$R^8$—$C(O)OR^7$, and —$R^8$—$S(O)_tR^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

5. The compound of claim 4 selected from the group consisting of:

5-ureido-3-[(4-(3-methoxyphenyl)pyrrol-2-yl)methylene]indolin-2-one;

5-ureido-3-[(4-(4-methoxyphenyl)pyrrol-2-yl)methylene]indolin-2-one;

5-ureido-3-[(4-(3-hydroxyphenyl)pyrrol-2-yl)methylene]indolin-2-one;

5-ureido-3-[(4-(3-acetylaminophenyl)pyrrol-2-yl)methylene]indolin-2-one;

5-ureido-3-[(4-(3-carboxyphenyl)pyrrol-2-yl)methylene]indolin-2-one;

5-ureido-3-[(4-(pyridin-3-yl)pyrrol-2-yl)methylene]indolin-2-one;

5-ureido-3-[(4-(3-(2-morpholin-4-ylethoxy)phenyl)pyrrol-2-yl)methylene]indolin-2-one;

5-ureido-3-[(4-(3-methoxycarbonylmethoxyphenyl)pyrrol-2-yl)methylene]indolin-2-one;

5-ureido-3-[(4-(4-methoxycarbonylphenyl)pyrrol-2-yl)methylene]indolin-2-one;

5-ureido-3-[(4-(3-aminocarbonylphenyl)pyrrol-2-yl)methylene]indolin-2-one;

5-ureido-3-[(4-(3,4-dimethoxyphenyl)pyrrol-2-yl)methylene]indolin-2-one;

5-ureido-3-[(4-(4-carboxyphenyl)pyrrol-2-yl)methylene]indolin-2-one;

5-ureido-3-[(4-(3,4-dihydroxyphenyl)pyrrol-2-yl)methylene]indolin-2-one;

5-ureido-3-[(4-(4-(1,1-dimethylethoxycarbonylamino)methylphenyl)pyrrol-2-yl)methylene]indolin-2-one;

5-ureido-3-[(4-(3-aminomethylphenyl)pyrrol-2-yl)methylene]indolin-2-one;

5-ureido-3-[(4-(3-acetamidomethylphenyl)pyrrol-2-yl)methylene]indolin-2-one;
5-ureido-3-[(4-(3-(2-piperidin-1-ylethyl)aminocarbonylphenyl)pyrrol-2-yl)methylene]indolin-2-one;
5-ureido-3-[(4-(3-(1,1-dimethylethoxycarbonyl)aminoacetamidomethylphenyl)pyrrol-2-yl)methylene]indolin-2-one;
5-ureido-3-[(4-(4-methylsulfonylphenyl)pyrrol-2-yl)methylene]indolin-2-one;
5-ureido-3-[(4-(4-(2-piperidin-1-ylethyl)aminocarbonylphenyl)pyrrol-2-yl)methylene]indolin-2-one;
5-ureido-3-[(4-(4-(2-dimethylaminoethyl)aminocarbonylphenyl)pyrrol-2-yl)methylene]indolin-2-one;
5-ureido-3-[(4-(4-(4-methylpiperazin-1-yl)carbonylphenyl)pyrrol-2-yl)methylene]indolin-2-one;
5-ureido-3-[(4-(3-(2-dimethylaminoethyl)aminocarbonylphenyl)pyrrol-2-yl)methylene]indolin-2-one;
5-ureido-3-[(4-(3-(4-methylpiperazin-1-yl)carbonylphenyl)pyrrol-2-yl)methylene]indolin-2-one;
5-ureido-3-[(4-(4-(3-hydroxypyrrolidin-1-yl)carbonylphenyl)pyrrol-2-yl)methylene]indolin-2-one;
5-ureido-3-[(4-(3-(3-hydroxypyrrolidin-1-yl)carbonylphenyl)pyrrol-2-yl)methylene]indolin-2-one;
5-ureido-3-[(4-(pyrimidin-5-yl)pyrrol-2-yl)methylene]indolin-2-one; and
5-ureido-3-[(4-(5-methoxypyridin-3-yl)pyrrol-2-yl)methylene]indolin-2-one.

6. A pharmaceutical composition comprising a pharmaceutically acceptable excipient and a compound of formula (I):

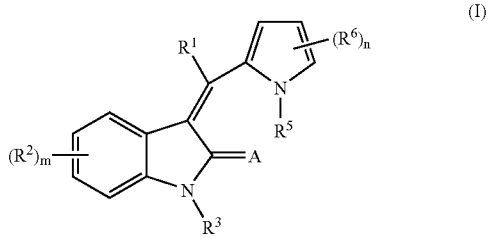

wherein:
m is 0 to 4;
n is 1 to 3;
A is oxygen;
$R^1$ is hydrogen, alkyl, —C(O)OR$^7$, or —C(O)N(R$^7$)$_2$; or
$R^1$ is aryl (optionally substituted by one or more substituents selected from the group consisting of alkyl, aryl, aralkyl, halo, haloalkyl, cyano, nitro, —R$^8$—OR$^7$, —R$^8$—N(R$^7$)$_2$, —R$^8$—C(O)OR$^7$, —R$^8$—C(O)N(R$^7$)$_2$, —R$^8$—N(R$^7$)C(O)N(R$^7$)$_2$, —R$^8$—N(R$^7$)C(O)—R$^9$—N(R$^7$)$_2$ and —R$^8$—N(R$^7$)C(O)OR$^7$); or
$R^1$ is aralkyl (optionally substituted by one or more substituents selected from the group consisting of alkyl, aryl, aralkyl, halo, haloalkyl, cyano, nitro, —R$^8$—OR$^7$, —R$^8$—N(R$^7$)$_2$, —R$^8$—C(O)OR$^7$, —R$^8$—C(O)N(R$^7$)$_2$, —R$^8$—N(R$^7$)C(O)N(R$^7$)$_2$, —R$^8$—N(R$^7$)C(O)—R$^9$—N(R$^7$)$_2$ and —R$^8$—N(R$^7$)C(O)OR$^7$);
each $R^2$ is independently selected from the group consisting of alkyl, alkenyl, alkynyl, halo, haloalkyl, haloalkenyl, cyano, —R$^8$—OR$^7$, —R$^8$—N(R$^7$)$_2$, —R$^8$—C(O)OR$^7$, —R$^8$—C(O)N(R$^7$)$_2$, —R$^8$—N(R$^7$)S(O)$_t$R$^7$ (where t is 1 or 2), —R$^8$—N(R$^7$)S(O)$_t$N(R$^7$)$_2$ (where t is 1 or 2), —R$^8$—N(R$^7$)S(O)$_t$N(R$^7$)C(O)OR$^7$ (where t is 1 or 2), —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)—R$^9$—C(O)N(R$^7$)$_2$, —R$^8$—N(R$^7$)C(O)—R$^8$—N(R$^7$)—R$^8$—C(O)OR$^7$, —R$^8$—N(R$^7$)C(O)—R$^8$—N(R$^7$)—R$^8$—C(O)—R$^8$—N(R$^7$)$_2$, —N(R$^7$)C(=NR$^7$)N(R$^7$)$_2$, —C(=NR$^7$)—N(R$^7$)$_2$, —R$^8$—N=C(R$^7$)$_2$, heterocyclyl (optionally substituted by one or more substituents selected from the group consisting of alkyl, aryl, aralkyl, halo, haloalkyl, cyano, nitro, —R$^8$—OR$^7$, —R$^8$—C(O)OR$^7$, —R$^8$—C(O)N(R$^7$)$_2$, —R$^8$—N(R$^7$)$_2$, —R$^8$—N(R$^7$)C(O)—R$^8$—N(R$^7$)$_2$ and —R$^8$—N(R$^7$)C(O)OR$^7$), and optionally substituted cyclic ureido groups;
$R^3$ is hydrogen, alkyl or aralkyl;
$R^5$ is hydrogen, alkyl, aryl, aralkyl, —C(O)R$^{11}$ or —S(O)$_2$R$^{11}$;
each $R^6$ is optionally substituted phenyl;
each $R^7$ is independently hydrogen, optionally substituted alkyl, haloalkyl, optionally substituted aryl, optionally substituted aralkyl, optionally substituted heterocyclyl, or optionally substituted heterocyclylalkyl;
each $R^8$ is a bond or a straight or branched alkylene chain;
each $R^9$ is a straight or branched alkylene chain;
each $R^{11}$ is optionally substituted alkyl, haloalkyl, optionally substituted aryl, optionally substituted aralkyl, optionally substituted heterocyclyl, or optionally substituted heterocyclylalkyl;
as a single stereoisomer, a mixture of stereoisomers, a solvate or a pharmaceutically acceptable salt thereof;
with the following provisos:
(1) when m is 2, n is 1, A is oxygen, $R^1$, $R^3$ and $R^5$ are each hydrogen, $R^6$ is 3-methoxy, and one $R^2$ is 4-amino, the other $R^2$ can not be 5-amino; and
(2) when m is 2, n is 1, A is oxygen, $R^1$, $R^3$ and $R^5$ are each hydrogen, $R^8$ is 3-methoxy, and one $R^2$ is 5-nitro, the other $R^2$ can be 4-fluoro or 4-azido.

7. A compound of formula (Ia) as a single stereoisomer, a mixture of stereoisomers, a solvate or a pharmaceutically acceptable salt thereof:

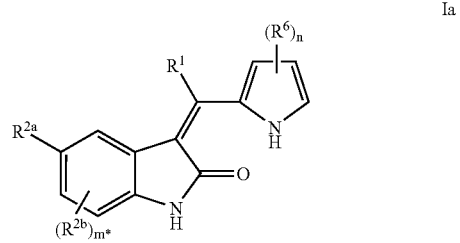

wherein
$R^1$ is hydrogen or alkyl;
$R^{2a}$ is —R$^8$—N(R$^7$)$_2$, —R$^8$—N(R$^7$)S(O)$_t$N(R$^7$)$_2$ (where t is 1 or 2), —R$^8$—N(R$^7$)S(O)$_t$N(R$^7$)C(O)OR$^7$ (where t is 1 or 2), —R$^8$—N(R$^7$)C(O)R$^7$, —R$^8$—N(R$^7$)—R$^8$—C(O)OR$^7$, —R$^8$—N(R$^7$)C(O)N(R$^7$)$_2$, —R$^8$—N(R$^7$)C(O)—R$^9$—N(R$^7$)$_2$, —R$^8$—N(R$^7$)—R$^9$—C(O)N(R$^7$)$_2$, —R$^8$—N(R$^7$)C(O)—R$^8$—N(R$^7$)—R$^8$—C(O)OR$^7$, —R$^8$—N(R$^7$)C(O)—R$^8$—N(R$^7$)—R$^8$—C(O)—R$^8$—N(R$^7$)$_2$, —N(R$^7$)C(=NR$^7$)N(R$^7$)$_2$, or —R$^8$—N=C(R$^7$)$_2$;
each $R^{2b}$ is independently selected from the group consisting of alkyl, alkenyl, alkynyl, halo, haloalkyl, haloalkenyl, cyano, —R$^8$—OR$^7$, —R$^8$—N(R$^7$)$_2$, —R$^8$—C(O)OR$^7$, —R$^8$—C(O)N(R$^7$)$_2$, —R$^8$—S(O)$_t$N (R⁷)₂ (where t is 1 or 2), —R⁸—N(R⁷)S(O)ₜR⁷ (where t is 1 or 2), —R⁸—N(R⁷)S(O)ₜN(R⁷)₂ (where t is 1 or 2), —R⁸—N(R⁷)S(O)ₜN(R⁷)C(O)OR⁷ (where t is 1 or 2), —R⁸—N(R⁷)C(O)R⁷, —R⁸—N(R⁷)—R⁸—C(O)OR⁷, —R⁸—N(R⁷)C(O)N(R⁷)₂, —R⁸—N(R⁷)C(O)—R⁹—N(R⁷)₂, —R⁸—N(R⁷)—R⁹—C(O)N(R⁷)₂, —R⁸—N(R⁷)C(O)—R⁸—N(R⁷)—R⁸—C(O)OR⁷, —R⁸—N(R⁷)C(O)—R⁸—N(R⁷)—R⁸—C(O)—R⁸—N(R⁷)₂, —N(R⁷)C(=NR⁷)N(R⁷)₂, —C(=NR⁷)—N(R⁷)₂, —R⁸—N=C(R⁷)₂, heterocyclyl (optionally substituted by one or more substituents selected from the group consisting of alkyl, aryl, aralkyl, halo, haloalkyl, cyano, nitro, —R⁸—OR⁷, —R⁸—C(O)OR⁷, —R⁸—C(O)N(R⁷)₂, —R⁸—N(R⁷)₂, —R⁸—N(R⁷)C(O)—R⁸—N(R⁷)₂ and —R⁸—N(R⁷)C(O)OR⁷); and optionally substituted cyclic ureido groups;

m* is 0 to 3;

n is 1 to 3;

each R⁸ is phenyl (optionally substituted by one or more substituents selected from the group consisting of alkyl, —R⁸—OR⁷, —R⁸—O—R⁸—C(O)OR⁷, —R⁸—C(O)R⁷, —R⁸—C(O)OR⁷, —R⁸—C(O)N(R⁷)₂, —R⁸—N(R⁷)C(O)R⁷, —R⁸—N(R⁷)C(O)OR⁷, —R⁸—N(R⁷)₂, —R⁸—N(R⁷)C(O)—R⁸—N(R⁷)—R⁸—C(O)OR⁷, and —R⁸—S(O)ₜR⁷ (where t is 0 to 2));

each R⁷ is independently hydrogen, optionally substituted alkyl, haloalkyl, optionally substituted aryl, optionally substituted aralkyl, optionally substituted heterocyclyl, or optionally substituted heterocyclylalkyl;

each R⁸ is a bond or a straight or branched alkylene chain; and each R⁹ is a straight or branched alkylene chain.

8. A compound of claim 7 wherein

R¹ is hydrogen;

R²ᵃ is —R⁸—N(R⁷)₂, —R⁸—N(R⁷)S(O)ₜN(R⁷)C(O)OR⁷ (where t is 1 or 2), —R⁸—N(R⁷)C(O)R⁷, —R⁸—N(R⁷)—R⁸—C(O)OR⁷, —R⁸—N(R⁷)C(O)N(R⁷)₂, —R⁸—N(R⁷)C(O)—R⁹—N(R⁷)₂, —R⁸—N(R⁷)—R⁹—C(O)N(R⁷)₂, —R⁸—N(R⁷)C(O)—R⁸—N(R⁷)—R⁸—C(O)OR⁷, —R⁸—N(R⁷)C(O)—R⁸—N(R⁷)—R⁸—C(O)—R⁸—N(R⁷)₂, —N(R⁷)C(=NR⁷)N(R⁷)₂, or —R⁸—N=C(R⁷)₂; and m* is 0.

9. A compound of claim 8 wherein

R²ᵃ is —R⁸—N(R⁷)S(O)ₜN(R⁷)C(O)OR⁷ (where t is 1 or 2), —R⁸—N(R⁷)C(O)R⁷, —R⁸—N(R⁷)—R⁸—C(O)OR⁷, —R⁸—N(R⁷)C(O)N(R⁷)₂, —R⁸—N(R⁷)C(O)—R⁹—N(R⁷)₂, —R⁸—N(R⁷)—R⁹—C(O)N(R⁷)₂, —R⁸—N(R⁷)C(O)—R⁸—N(R⁷)—R⁸—C(O)OR⁷, or —R⁸—N(R⁷)C(O)—R⁸—N(R⁷)—R⁸—C(O)—R⁸—N(R⁷)₂; and m* is 0.

10. A compound of claim 9 wherein

R²ᵃ is —R⁸—N(R⁷)C(O)R⁷, —R⁸—N(R⁷)—R⁸—C(O)OR⁷, —R⁸—N(R⁷)C(O)N(R⁷)₂, —R⁸—N(R⁷)—R⁹—C(O)N(R⁷)₂, or —R⁸—N(R⁷)C(O)—R⁹—N(R⁷)₂; and each R⁶ is phenyl (optionally substituted by one or more substituents selected from the group consisting of alkyl, —R⁸—OR⁷, —R⁸—O—R⁸—C(O)OR⁷, —R⁸—C(O)R⁷, —R⁸—C(O)OR⁷, —R⁸—C(O)N(R⁷)₂, —R⁸—N(R⁷)C(O)R⁷, —R⁸—N(R⁷)C(O)OR⁷, —R⁸—N(R⁷)₂, —R⁸—N(R⁷)C(O)—R⁸—N(R⁷)—R⁸—C(O)OR⁷, and —R⁸—S(O)ₜR⁷ (where t is 0 to 2).

11. The compound of claim 10 selected from the group consisting of the following:

5-ureido-3-[(4-(3-methoxyphenyl)pyrrol-2-yl)methylene]indolin-2-one;

5-ureido-3-[(4-(4-methoxyphenyl)pyrrol-2-yl)methylene]indolin-2-one;

5-ureido-3-[(4-(3-hydroxyphenyl)pyrrol-2-yl)methylene]indolin-2-one;

5-ureido-3-[(4-(3-acetylaminophenyl)pyrrol-2-yl)methylene]indolin-2-one;

5-ureido-3-[(4-(3-carboxyphenyl)pyrrol-2-yl)methylene]indolin-2-one;

5-ureido-3-[(4-(3-methoxycarbonylmethoxyphenyl)pyrrol-2-yl)methylene]indolin-2-one:

5-ureido-3-[(4-(4-methoxycarbonylphenyl)pyrrol-2-yl)methylene]indolin-2-one;

5-ureido-3-[(4-(3-aminocarbonylphenyl)pyrrol-2-yl)methylene]indolin-2-one;

5-ureido-3-[(4-(3,4-dimethoxyphenyl)pyrrol-2-yl)methylene]indolin-2-one;

5-ureido-3-[(4-(4-carboxyphenyl)pyrrol-2-yl)methylene]indolin-2-one;

5-ureido-3-[(4-(3,4-dihydroxyphenyl)pyrrol-2-yl)methylene]indolin-2-one;

5-ureido-3-[(4-(4-(1,1-dimethylethoxycarbonylamino)methylphenyl)pyrrol-2-yl)methylene]indolin-2-one;

5-ureido-3-[(4-(3-aminomethylphenyl)pyrrol-2-yl)methylene]indolin-2-one;

5-ureido-3-[(4-(3-acetamidomsthylphenyl)pyrrol-2-yl)methylene]indolin-2-one;

5-ureido-3-[(4-(3-(2-piperidin-1-ylethyl)aminocarbonylphenyl)pyrrol-2-yl)methylene]indolin-2-one;

5-ureido-3-[(4-(3-(1,1-dimethylethoxycarbonyl)aminoacetamidomethyl-phenyl)pyrrol-2-yl)methylene]indolin-2-one;

5-ureido-3-[(4-(4-methylsulfonylphenyl)pyrrol-2-yl)methylene]indolin-2-one;

5-ureido-3-[(4-(4-(2-piperidin-1-ylethyl)aminocarbonylphenyl)pyrrol-2-yl)methylene]indolin-2-one:

5-ureido-3-[(4-(4-(2-dimethylaminoethyl)aminocarbonylphenyl)pyrrol-2-yl)methylene]indolin-2-one;

5-ureido-3-[(4-(4-(4-methylpiperazin-1-yl)carbonylphenyl)pyrrol-2-yl)methylene]indolin-2-one;

5-ureido-3-[(4-(3-(2-dimethylaminoethyl)aminocarbonylphenyl)pyrrol-2-yl)methylene]indolin-2-one;

5-ureido-3-[(4-(3-(4-methylpiperazin-1-yl)carbonylphenyl)pyrrol-2-yl)methylene]indolin-2-one;

5-ureido-3-[(4-(4-(3-hydroxypyrrolidin-1-yl)carbonylphenyl)pyrrol-2-yl)methylene]indolin-2-one; and 5-ureido-3-[(4-(3-(3-hydroxypyrrolidin-1-yl)carbonylphenyl)pyrrol-2-yl)methylene]indolin-2-one.

12. The pharmaceutical composition of claim 6 comprising a pharmaceutically acceptable excipient and a compound of formula (I) wherein:

m is 1 to 4;

n is 1 to 3;

A is oxygen;

R¹ is hydrogen or alkyl; or

R¹ is aryl (optionally substituted by one or more substituents selected from the group consisting of —R⁸—OR⁷, —R⁸—N(R⁷)₂, —R⁸—C(O)N(R⁷)₂, —R⁸—N(R⁷)C(O)N(R⁷)₂, —R⁸—N(R⁷)C(O)—R⁹—N(R⁷)₂ and —R⁸—N(R⁷)C(O)OR⁷);

each R² is independently selected from the group consisting of heterocyclyl —R⁸—N(R⁷)₂, —R⁸—N(R⁷)S(O)ₜ(R⁷)C(O)OR⁷ (where t is 1 or 2), —R⁸—N(R⁷)C(O)R⁷, —R⁸—N(R⁷)—R⁸—C(O)OR⁷, —R⁸—N(R⁷)C(O)N $(R^7)_2$, —$R^8$—$N(R^7)C(O)$—$R^9$—$N(R^7$—$R^8$—$N(R^7)$—$R^9$—$C(O)N(R^7)_2$, —$R^6$—$N(R^7)C(O)$—$R^8$—$N(R^7)$—$R^8$—$C(O)OR^7$, —$R^8$—$N(R^7)C(O)$—$R^8$—$N(R^7)$—$R^8$—$C(O)$—$R^8$—$N(R^7)_2$, —$N(R^7)C(=NR^7)N(R^7)_2$, and —$R^8$—$N=C(R^7)_2$;

$R^3$ is hydrogen;

$R^5$ is hydrogen or alkyl;

each $R^6$ is phenyl (optionally substituted by one or more substituents selected from the group consisting of alkyl, —$R^8$—$OR^7$, —$R^8$—$O$—$R^9$—$C(O)OR^7$, —$R^8$—$C(O)R^7$, —$R^8$—$C(O)OR^7$, —$R^8$—$C(O)N(R^7)_2$, —$R^8$—$N(R^7)C(O)R^7$, —$R^8$—$N(R^7)C(O)OR^7$, —$R^8$—$N(R^7)_2$, —$R^8$—$N(R^7)C(O)$—$R^8$—$N(R^7)$—$R^8$—$C(O)OR^7$, and —$R^8$—$S(O)_tR^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

13. The pharmaceutical composition of claim 12 comprising a pharmaceutically acceptable excipient and a compound of formula (I) wherein:

m is 1;

n is 1 to 3;

A is oxygen;

$R^1$ is hydrogen or alkyl;

$R^2$ is —$R^8$—$N(R^7)C(O)R^7$, —$R^8$—$N(R^7)$—$R^8$—$C(O)OR^7$, —$R^8$—$N(R^7)C(O)N(R^7)_2$, —$R^8$—$N(R^7)$—$R^9$—$C(O)N(R^7)_2$, or —$R^8$—$N(R^7)C(O)$—$R^9$—$N(R^7)_2$;

$R^3$ is hydrogen;

$R^5$ is hydrogen or alkyl;

$R^6$ is phenyl (optionally substituted by one or more substituents selected from the group consisting of —$R^8$—$OR^7$, —$R^8$—$O$—$R^9$—$C(O)OR^7$, —$R^8$—$C(O)OR^7$, —$R^8$—$C(O)N(R^7)_2$, —$R^8$—$N(R^7)C(O)R^7$, —$R^8$—$N(R^7)C(O)OR^7$, —$R^8$—$N(R^7)_2$, —$R^8$—$N(R^7)C(O)$—$R^8$—$N(R^7)$—$R^8$—$C(O)OR^7$, and —$R^8$—$S(O)_tR^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl:

each $R^8$ is a bond or a straight or branched alkylene chain; and each $R^9$ is a straight or branched alkylene chain.

14. The pharmaceutical composition of claim 12 comprising a pharmaceutically acceptable excipient and a compound of formula (I) wherein:

m is 1;

n is 1;

A is oxygen;

$R^1$ is hydrogen or alkyl;

$R^2$ is —$R^8$—$N(R^7)C(O)R^7$, —$R^8$—$N(R^7)$—$R^8$—$C(O)OR^7$, —$R^8$—$N(R^7)C(O)N(R^7)_2$, —$R^8$—$N(R^7)$—$R^9$—$C(O)N(R^7)_2$, or —$R^8$—$N(R^7)C(O)$—$R^9$—$N(R^7)_2$;

$R^3$ is hydrogen;

$R^5$ is hydrogen or alkyl;

$R^6$ is phenyl (optionally substituted by one or more substituents selected from the group consisting of —$R^8$—$OR^7$, —$R^8$—$O$—$R^9$—$C(O)OR^7$, —$R^8$—$C(O)R^7$, —$R^8$—$C(O)OR^7$, —$R^8$—$C(O)N(R^7)_2$, —$R^8$—$N(R^7)C(O)R^7$, —$R^8$—$N(R^7)C(O)OR^7$, —$R^8$—$N(R^7)_2$, —$R^8$—$N(R^7)C(O)$—$R^8$—$N(R^7)$—$R^8$—$C(O)OR^7$, and —$R^8$—$S(O)_tR^7$ (where t is 0 to 2));

each $R^7$ is independently hydrogen, optionally substituted alkyl, haloalkyl, optionally substituted aryl, optionally substituted aralkyl, optionally substituted heterocyclyl, or optionally substituted heterocyclylalkyl;

each $R^8$ is a bond or a straight or branched alkylene chain; and each $R^9$ is a straight or branched alkylene chain.

15. The pharmaceutical composition of claim 14 comprising a pharmaceutically acceptable excipient and a compound selected from the group consisting of:

5-ureido-3-[(4-(3-methoxyphenyl)pyrrol-2-yl)methylene]indolin-2-one;

5-ureido-3-[(4-(4-methoxyphenyl)pyrrol-2-yl)methylene]indolin-2-one;

5-ureido-3-[(4-(3-hydroxyphenyl)pyrrol-2-yl)methylene]indolin-2-one;

5-ureido-3-[(4-(3-acetylaminophenyl)pyrrol-2-yl)methylene]indolin-2-one;

5-ureido-3-[(4-(3-carboxyphenyl)pyrrol-2-yl)methylene]indolin-2-one;

5-ureido-3-[(4-(3-methoxycarbonylmethoxyphenyl)pyrrol-2-yl)methylene]indolin-2-one;

5-ureido-3-[(4-(4-methoxycarbonylphenyl)pyrrol-2-yl)methylene]indolin-2-one;

5-ureido-3-[(4-(3-aminocarbonylphenyl)pyrrol-2-yl)methylene]indolin-2-one;

5-ureido-3-[(4-(3,4-dimethoxyphenyl)pyrrol-2-yl)methylene]indolin-2-one;

5-ureido-3-[(4-(4-carboxyphenyl)pyrrol-2-yl)methylene]indolin-2-one;

5-ureido-3-[(4-(3,4-dihydroxyphenyl)pyrrol-2-yl)methylene]indolin-2-one;

5-ureido-3-[(4-(4-(1,1-dimethylethoxycarbonylamino)methylphenyl)pyrrol-2-yl)methylene]indolin-2-one;

5-ureido-3-[(4-(3-aminomethylphenyl)pyrrol-2-yl)methylene]indolin-2-one;

5-ureido-3-[(4-(3-acetamidomethylphenyl)pyrrol-2-yl)methylene]indolin-2-one;

5-ureido-3-[(4-(3-(2-piperidin-1-ylethylaminocarbonylphenyl)pyrrol-2-yl)methylene]indolin-2-one;

5-ureido-3-[(4-(3-(1,1-dimethylethoxycarbonyl)aminoacetamidomethyl-phenyl)pyrrol-2-yl)methylene]indolin-2-one;

5-ureido-3-[(4-(4-methylsulfonylphenyl)pyrrol-2-yl)methylene]indolin-2-one;

5-ureido-3-[(4-(4-(2-piperidin-1-ylethyl)aminocarbonylphenyl)pyrrol-2-yl)methylene]indolin-2-one;

5-ureido-3-[(4-(4-(2-dimethylaminoethyl)aminocarbonylphenyl)pyrrol-2-yl)methylene]indolin-2-one;

5-ureido-3-[(4-(4-(4-methylpiperazin-1-yl)carbonylphenyl)pyrrol-2-yl)methylene]indolin-2-one;

5-ureido-3-[(4-(3-(2-dimethylaminoethyl)aminocarbonylphenyl)pyrrol-2-yl)methylene]indolin-2-one;

5-ureido-3-[(4-(3-(4-methylpiperazin-1-yl)carbonylphenyl)pyrrol-2-yl)methylene]indolin-2-one;

5-ureido-3-[(4-(4-(3-hydroxypyrrolidin-1-yl)carbonylphenyl)pyrrol-2-yl)methylene]indolin-2-one; and 5-ureido-3-[(4-(3-(3-hydroxypyrrolidin-1-yl)carbonylphenyl)pyrrol-2-yl)methylene]indolin-2-one.

* * * * *